United States Patent
Kuehnle et al.

(10) Patent No.: US 10,572,745 B2
(45) Date of Patent: Feb. 25, 2020

(54) SYSTEM AND METHODS OF MONITORING DRIVER BEHAVIOR FOR VEHICULAR FLEET MANAGEMENT IN A FLEET OF VEHICLES USING DRIVER-FACING IMAGING DEVICE

(71) Applicant: Bendix Commercial Vehicle Systems LLC, Elyria, OH (US)

(72) Inventors: Andreas U. Kuehnle, Villa Park, CA (US); Zheng Li, Irvine, CA (US); Hans M. Molin, Mission Viejo, CA (US); Cathy L. Boon, Orange, CA (US)

(73) Assignee: Bendix Commercial Vehicle Systems LLC, Elyria, OH (US)

( * ) Notice: Subject to any disclaimer, the term of this patent is extended or adjusted under 35 U.S.C. 154(b) by 0 days.

(21) Appl. No.: 15/810,030

(22) Filed: Nov. 11, 2017

(65) Prior Publication Data
US 2019/0147263 A1    May 16, 2019

(51) Int. Cl.
*G06K 9/00* (2006.01)
*B60W 40/09* (2012.01)
(Continued)

(52) U.S. Cl.
CPC ......... *G06K 9/00845* (2013.01); *B60W 40/08* (2013.01); *B60W 40/09* (2013.01);
(Continued)

(58) Field of Classification Search
CPC combination set(s) only.
See application file for complete search history.

(56) References Cited

U.S. PATENT DOCUMENTS 9,690,292 B1   6/2017   Chan
2002/0105426 A1*  8/2002   Young ................. G08B 21/06
                                                340/576
(Continued)

FOREIGN PATENT DOCUMENTS

EP    3239011 A1    11/2017

OTHER PUBLICATIONS

Office Action to corresponding U.S. Appl. No. 15/810,029, dated Oct. 12, 2018.
(Continued)

*Primary Examiner* — Nabil H Syed
*Assistant Examiner* — Cal J Eustaquio
(74) *Attorney, Agent, or Firm* — Tucker Ellis LLP; Michael Hudzinski

(57) ABSTRACT

Systems and methods monitor driver behavior for vehicular fleet management in a fleet of vehicles using driver-facing imaging device. The systems and methods herein relate generally to vehicular fleet management for enhancing safety of the fleet and improving the performance of the fleet drivers, and further relate to monitoring the operation of fleet vehicles using one or more driver-facing imaging devices disposed in the fleet vehicles for recording activities of the fleet drivers and their passengers, storing information relating to the monitored activities, selectively generating warnings related to the monitored activities, and reporting the monitored activities to a central fleet management system for use in enhancing the safety of the vehicles of the fleet and for helping to improve the performance of the fleet drivers.

18 Claims, 28 Drawing Sheets

(51) Int. Cl.
  G07C 5/00 (2006.01)
  B60W 40/08 (2012.01)
  G07C 5/08 (2006.01)
  *A61B 5/18* (2006.01)
  *A61B 5/16* (2006.01)
(52) U.S. Cl.
  CPC ........... *G07C 5/008* (2013.01); *G07C 5/0808* (2013.01); *G07C 5/0866* (2013.01); *A61B 5/163* (2017.08); *A61B 5/18* (2013.01); *G06K 9/00248* (2013.01); *G06K 9/00838* (2013.01)

(56) References Cited

U.S. PATENT DOCUMENTS

| | | | |
|---|---|---|---|
| 2002/0184236 A1* | 12/2002 | Donath | B60R 1/00 |
| 2002/0188392 A1* | 12/2002 | Breed | B60C 11/24 |
| | | | 701/45 |
| 2007/0040691 A1* | 2/2007 | Lau | A61B 5/16 |
| | | | 340/573.1 |
| 2007/0151516 A1* | 7/2007 | Law | C23C 16/45565 |
| | | | 118/723 E |
| 2008/0319602 A1 | 12/2008 | McClellan | |
| 2010/0033333 A1* | 2/2010 | Victor | A61B 3/113 |
| | | | 340/576 |
| 2012/0242819 A1 | 9/2012 | Schamp | |
| 2013/0090562 A1* | 4/2013 | Ryan | A61B 3/032 |
| | | | 600/473 |
| 2013/0135109 A1* | 5/2013 | Sharon | G08B 21/02 |
| | | | 340/576 |
| 2014/0139655 A1 | 5/2014 | Mimar | |
| 2015/0054934 A1 | 2/2015 | Haley | |
| 2015/0270983 A1* | 9/2015 | Givental | H04L 12/1831 |
| | | | 382/103 |
| 2016/0001781 A1 | 1/2016 | Fung | |
| 2016/0009175 A1 | 1/2016 | Mcnew | |
| 2016/0046261 A1 | 2/2016 | Gulash | |
| 2016/0078306 A1 | 3/2016 | Allan | |
| 2017/0061222 A1 | 3/2017 | Hoye | |
| 2017/0154513 A1* | 6/2017 | Hariri | B60N 2/002 |
| 2017/0344838 A1 | 11/2017 | Zhou | |
| 2018/0088661 A1 | 3/2018 | Betancourt | |
| 2018/0211123 A1 | 7/2018 | Yasuda | |

OTHER PUBLICATIONS

International Search Report and Written Opinion from correlating International Application No. PCT/US18/60031, dated Apr. 26, 2019, 14 pages.

International Search Report and Written Opinion from correlating International Application No. PCT/US2018/060094, dated Feb. 13, 2019; 14 pages.

Non-Final Office Action issued in related U.S. Appl. No. 16/413,913, dated Dec. 18, 2019.

\* cited by examiner

Passenger
Detection
BCVS-2017-162

Passenger
Detection
BCVS-2017-162

Seat Belt Detector
BCVS-2017-30

Seat Belt Detector
BCVS-2017-30

Seat Belt Detector
BCVS-2017-30

Hands on Steering Wheel
BCVS-2017-31

Hands on Steering
Wheel
BCVS-2017-31

Driver Road
Attention Device
BCVS-2017-53

Impeded Driver-Facing Camera
BCVS-2017-181

Driver's Head Out
of Position
BCVS-2017-80

Driver's Head Out
of Position
BCVS-2017-80

Driver Head Pose
BCVS-2017-163

Driver Head Pose
BCVS-2017-163

Driver Head Pose
BCVS-2017-163

Driver Head Pose
BCVS-2017-163

Driver Head Pose
BCVS-2017-163

Driver Head Pose
BCVS-2017-163

Mirror Usage
Verification
BCVS-2017-11

SYSTEM AND METHODS OF MONITORING DRIVER BEHAVIOR FOR VEHICULAR FLEET MANAGEMENT IN A FLEET OF VEHICLES USING DRIVER-FACING IMAGING DEVICE

TECHNICAL FIELD

The embodiments herein relate generally to vehicular fleet management for enhancing safety of the fleet and improving the performance of the fleet drivers. More specifically, particular embodiments relate to monitoring the operation of fleet vehicles using one or more driver-facing imaging devices disposed in the fleet vehicles for recording activities of the fleet drivers and their passengers, and reporting the monitored activities to a central fleet management system for use in enhancing the safety of the vehicles of the fleet and for helping to improve the performance of the fleet drivers.

CROSS REFERENCE TO RELATED APPLICATIONS

This application is related to U.S. application Ser. No. 14/233,319, filed Jul. 12, 2012, entitled: VEHICULAR FLEET MANAGEMENT SYSTEM AND METHODS OF MONITORING AND IMPROVING DRIVER PERFORMANCE IN A FLEET OF VEHICLES, the contents of which is incorporated herein by reference in its entirety.

This application is also related to U.S. application Ser. No. 15/810,029, filed Nov. 11, 2017, entitled: SYSTEM AND METHODS OF MONITORING DRIVER BEHAVIOR FOR VEHICULAR FLEET MANAGEMENT IN A FLEET OF VEHICLES USING DRIVER-FACING IMAGING DEVICE, the contents of which is incorporated herein by reference in its entirety.

BACKGROUND

Existing systems and methods in the vehicular fleet management field focus on specific features of image capture systems and data transmission of files within the image capture systems. For example, U.S. Pat. No. 7,671,762 to Breslau teaches a system and method of transceiving vehicle data that involves transmission of data from one vehicle to another. Specifically, Breslau involves transmission and reception of vehicle identification data, and vehicular position data, and includes the use of Global Position Sensor (GPS) signals and satellite transmission.

Another existing technology is disclosed in U.S. Pat. No. 6,389,340 to Rayner wherein a circuit is taught that terminates image capture upon occurrence of a triggering event, and in which the system components are housed within a rearview mirror of a vehicle such as a car or truck.

U.S. Pat. No. 7,804,426 to Etcheson teaches a system and method for selective review of event data that comprises computer-assisted cueing of driving data for the selective review in order to save time. Event data is continuously captured and sent to a data buffer. The event data is sent to an event detector when requested by a fleet manager or the like.

In related U.S. application Ser. No. 14/233,319, filed Jul. 12, 2012, entitled: VEHICULAR FLEET MANAGEMENT SYSTEM AND METHODS OF MONITORING AND IMPROVING DRIVER PERFORMANCE IN A FLEET OF VEHICLES, a system and method is described in which vehicles are configured to collect driver and vehicle event data, selectively compress and encode the collected driver and vehicle event data, and communicate the compressed and encoded data wirelessly to one or more telematics service providers. One or more servers may poll this driver event data periodically, process it, and present multiple methods to end users by which they are able to view and analyze it. The system described permits fleet managers to use this driver event data, received through a report or notification, or pulled directly from a web-based portal, to monitor, correct and/or reward driver behavior, and to implement driver education and training programs, or the like.

In addition to the above, systems having both forward-facing cameras as well as driver-facing cameras are known as well. These systems typically continuously capture images of the roadway and of the driver within the interior of the vehicle, and store the images in a large buffer file, such as a first-in-first out (FOFO) buffer, for example. The roadway and driver image data is sent to an event detector when requested by a fleet manager or the like. In that way, the activities of the driver during any selected event can be determined by "winding back" the video of the recorded vehicle operation to the proper time of the occurrence of the selected event.

It is desirable, however, to more intelligently monitor driver behavior by monitoring one or more particular behaviors rather than by using gross imaging and/or by using gross vehicle data collection.

It is further desirable to analyze the one or more particular driver behaviors, preferably before an occurrence of any significant events, so that the driver or others such as fleet managers or the like may be suitably warned beforehand, if possible. It is further desirable that the drivers may further be graded relative to safety and other considerations, as well as ranked relative to other drivers in the fleet of vehicles, for motivating the drivers to behave better thereby enhancing the overall safety of the fleet and improving overall fleet performance.

SUMMARY OF THE EXAMPLE EMBODIMENTS

The embodiments herein provide for new and improved systems and methods of monitoring driver behavior for vehicular fleet management in a fleet of vehicles using a driver-facing imaging device.

In embodiments herein, systems and methods are provided using a driver-facing camera for monitoring driver behavior directly in accordance with a detected head position of the driver within the vehicle being operated by the driver. Systems and methods are provided using the driver-facing camera for monitoring the driver's use of commercial vehicle mirrors, for monitoring the driver's attention to the road, for monitoring the driver's head position relative to a proper head position, for monitoring the driver's head pose metric, for monitoring any impediments to the image collected by the driver-facing camera, and for monitoring the driver's eyes on the road and for making adjustments on adaptive lane departure warning system of the associated vehicle. These driver behaviors may be directly monitored as well as others as may be necessary and/or desired in accordance with the embodiments herein.

In further embodiments herein, systems and methods are provided using a driver-facing camera for monitoring driver behavior indirectly in accordance with detected aspects of components of the interior of the vehicle being operated by the driver. Systems and methods are provided using the driver-facing camera for monitoring the driver's proper use of the vehicle seatbelt, for monitoring the driver's proper hand positions on the steering when, and for monitoring the driver's compliance with fleet policies relative to unauthorized passengers being in the vehicle. These driver behaviors may be directly monitored as well as others as may be necessary and/or desired in accordance with the embodiments herein.

In accordance with embodiments herein, systems, methods and logic are provided including various vehicle sensors and a driver facing camera for determining when a set of one or more predetermined conditions of a vehicle are met or otherwise satisfied, determining a driver's head pose, learning or otherwise training the system on average values of the driver head pose (pitch, yaw, roll, etc.) when the set of one or more predetermined conditions of the vehicle are met or otherwise satisfied, and determining any occurrences of driver head pose deviations from the average values.

In accordance with embodiments herein, systems, methods and logic are provided including various vehicle sensors and a driver facing camera for determining a driver's head pose, learning or otherwise training the system on a head pose distribution and/or a head pose heat map, and determining any occurrences of driver head pose deviations from the a head pose distribution and/or a head pose heat map average values.

In accordance with embodiments herein, systems, methods and logic are provided including various vehicle sensors for determining when a set of one or more predetermined conditions propitious for determining infractions or driver misbehavior are met or otherwise satisfied such as for example a vehicle door status, a speed change, an unusual stopping location, unauthorized passenger visible, or the like, and a driver facing camera for obtaining images of the cabin of the vehicle in response to the set of one or more predetermined conditions of the vehicle are met.

In accordance with embodiments herein, systems, methods and logic are provided including various vehicle sensors and a driver facing camera for learning or otherwise training the system on average values of appearance (template images or descriptions) of vehicle cabin items, such as seat belt buckles, empty seats, steering wheel, door edges, mirror locations, and determining any occurrences of changes or deviations from the average or learned operational set values of the learned template images or descriptions.

In accordance with embodiments herein, systems, methods and logic are provided including various vehicle sensors and a driver facing camera for determining a driver's head pose vector, learning or otherwise training the system on average values of the driver's head pose vector, and selectively adapting other system values as a function of the driver's head pose vector when a persistent deviation from the driver looking at the road or the driver looking at the mirrors occurs.

In accordance with embodiments herein, systems, methods and logic provide multi-factor authentication using multiple sensors and a driver facing camera for driver identity verification using driver image data in combination with and voice print data of the driver, such as for example by imaging the driver using the driver facing camera, verifying a visual identity of the driver in accordance with driver database information and the driver image data obtaining voiceprint data of the driver uttering a standardized pass phrase while in the field of the driver facing camera verifying voiceprint identity of the driver requiring the driver to speak his name, leading to a standardized comparison template, and recording the protocol into a local memory of the system in the vehicle.

The term "processor means" as used herein refers to any microprocessor, discrete logic (e.g., ASIC), analog circuit, digital circuit, programmed logic device, memory device containing instructions, and so on. The term "processor means" also refers to "logic" which may include one or more gates, combinations of gates, other circuit components, hardware, firmware, software in execution on a machine, and/or combinations of each to perform a function(s) or an action(s), and/or to cause a function or action from another logic, method, and/or system, a software controlled microprocessor, a discrete logic (e.g., ASIC), an analog circuit, a digital circuit, a programmed logic device, a memory device containing instructions, and so on. The term "memory means" as used herein refers to any non-transitory media that participates in storing data and/or in providing instructions to the processor means for execution. Such a non-transitory medium may take many forms, including but not limited to volatile and non-volatile media. Non-volatile media includes, for example, optical or magnetic disks. Volatile media includes dynamic memory for example and does not include transitory signals, carrier waves, or the like. Common forms of computer-readable media include, for example, a floppy disk, a flexible disk, hard disk, magnetic tape, or any other magnetic medium, a CD-ROM, any other optical medium, punch cards, papertape, any other physical medium with patterns of holes, a RAM, PROM, and EPROM, a FLASH-EPROM, any other memory chip or cartridge, or any other tangible non-transitory medium from which a computer can read.

Other embodiments, features and advantages of the example embodiments will become apparent from the following description of the embodiments, taken together with the accompanying drawings, which illustrate, by way of example, the principles of the example embodiments.

BRIEF DESCRIPTION OF THE DRAWINGS

In the accompanying drawings which are incorporated in and constitute a part of the specification, embodiments of the invention are illustrated, which, together with a general description of the invention given above, and the detailed description given below, serve to exemplify the embodiments of this invention.

DETAILED DESCRIPTION OF THE EXAMPLE EMBODIMENTS

In the following description of the present invention reference is made to the accompanying figures which form a part thereof, and in which is shown, by way of illustration, exemplary embodiments illustrating the principles of the present invention and how it is practiced. Other embodiments can be utilized to practice the present invention and structural and functional changes can be made thereto without departing from the scope of the present invention.

Figure 1:
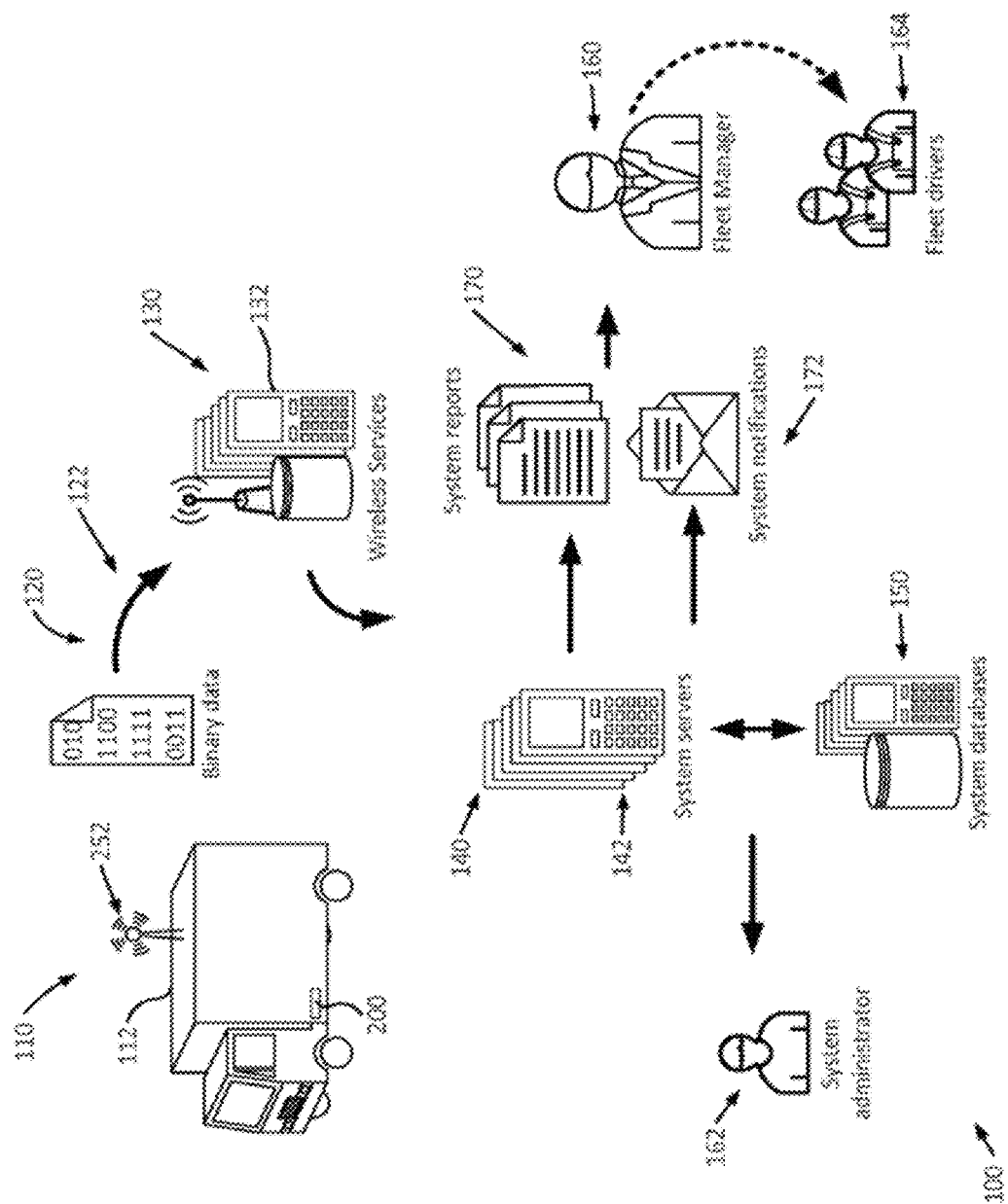
FIG. 1 is a diagram of an overview of the fleet management system and user layout according to the example embodiment.

Referring now to the drawings, wherein the showings are for the purpose of illustrating the example embodiments for monitoring driver behavior directly using a driver-facing camera in accordance with a detected head position of the driver within the vehicle being operated by the vehicle, and for monitoring driver behavior indirectly using a driver-facing camera in accordance with detected aspects of components of the interior of the vehicle being operated by the driver only, and not for purposes of limiting the same, FIG. 1 illustrates an overview of a fleet management and reporting system 100 in accordance with the example embodiment. In the example embodiment of the present invention, vehicles 110, such as trucks and cars, and particularly fleet vehicles 112, are configured with one or more data collection and reporting devices 200 (FIG. 2) that generate event data such as, in the example of a fleet of trucks, truck start, truck stop, and safety event data, wherein one such system includes for example a Lane Departure Warning (LDW) system 322 (FIG. 3) that generates signals indicative of one or more events and driver and vehicle event data regarding in the example of the fleet of trucks, truck lane wandering or crossing. Additionally, secondary systems to be described in greater detail below with reference to FIG. 3 carried by the vehicles or installed in the vehicle systems such as one or more video cameras, radar, transmission, engine, tire pressure monitoring and braking systems for example may generate additional safety event data. Third-party systems that generate proprietary safety events or data representative of detected safety events may also be involved. For example, the embodiments of the present invention may include software code implementing a Bendix® Wingman® ACB system available from Bendix Commercial Vehicle Systems LLC that captures proprietary safety events and other data relating to the proprietary safety events and/or relating to the operation of the vehicle by one or more vehicle operators or drivers.

With continued reference to FIG. 1, these events and event data 120 are, in the example embodiment, selectively sent via one or more wireless networks or wireless links 122 to network servers 132 of one or more service providers 130. Wireless service providers 130 utilize servers 132 (only one shown for ease of illustration) that collect the wireless data 120 provided by the trucks 112. Each also provides a web service by which users can report on or download data.

One or more servers 140 of the fleet management and reporting system 100 are configured to selectively download or otherwise retrieve data from the collection servers 132 which may be third party servers from one or more various telematics suppliers such as for example those available from PeopleNet Communications Corp. or Qualcomm Inc. for example. The one or more servers 140 of the fleet management and reporting system 100 are configured to initiate processing of the vehicular events and vehicular event data in manners to be described in greater detail below. A web application 142 executable on the one or more servers 140 of the fleet management and reporting system 100 includes a dynamic graphical user interface for fleet managers 160 and administrators 162 to view all of the information once it is processed. The subject fleet management and reporting system 100 of the example embodiment also includes one or more databases 150 configured to selectively store all event information provided from the vehicles 112 in the fleet 110 for one or more designated time intervals, including raw and post-processed trip data.

In accordance with the example embodiment, the system administrators 162 are users who are provided with interfaces to configure and manage fleets, monitor platform performance, view alerts issued by the platform, and view raw event data and subsequent processing logs and/or views. Fleet managers 160 may view event information for their respective fleet for internal processing. These events can arrive via user-initiated reports 170 in the web application 142 executable on the one or more servers 140, or via email or other notifications 172. Fleet managers 160 may, depending on internal policies and processes or for other reasons, also interface with individual drivers 164 regarding performance goals, corrections, reports, or coaching.

The subject fleet management and reporting system 100 of the example embodiment therefore offers a long list of functions and features to the end user. All have been designed to be driver centric, so that fleet managers 160 may focus their attention on driver education, training, and performance improvement. One of the primary beneficial and novel uses of the system 100 is the ease of access to driver specific-performance data and the ability to normalize each driver's performance to compare with the drivers of the fleet as a whole in order to pinpoint exemplary drivers for commendation as well as those in need of coaching or other corrective action.

Figure 2:
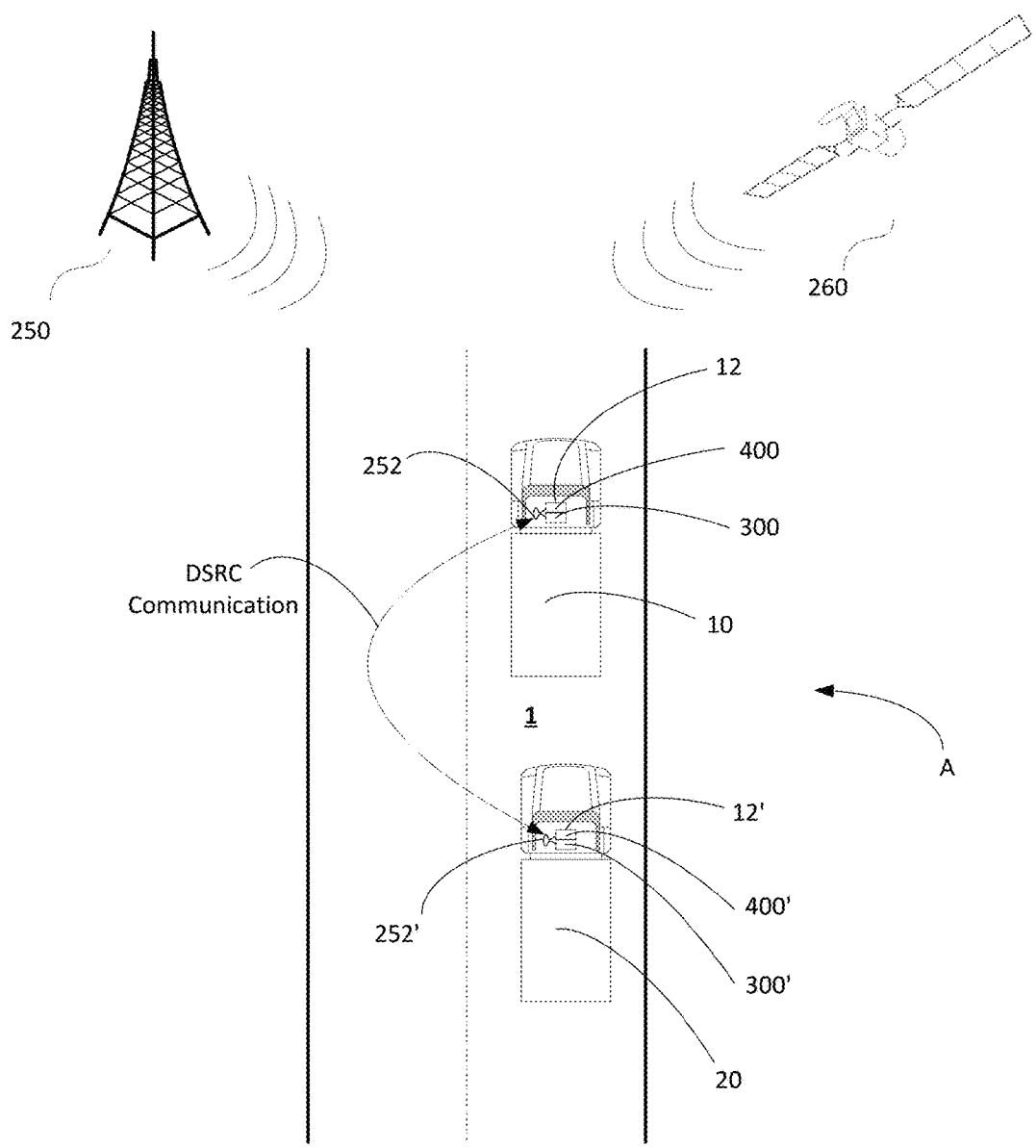
FIG. 2 depicts operation of an exemplary fleet vehicle operating in a platoon and having a driver behavior monitoring system having a driver facing camera in accordance with an embodiment.

FIG. 2 depicts operation of an exemplary fleet vehicle operating in a basic platoon A including a host or leader vehicle 10 in traffic with a second or follower vehicle 20 in accordance with the present disclosure. As shown, the follower vehicle 20 is traveling proximate to the leader vehicle 10 in an ordered platoon A along a roadway 1. The follower vehicle 20 is provided with an electronic control system 12' which includes a data collection and communication module portion 300' and a monitoring control portion 400' to be described in greater detail below. Similarly, the leader vehicle 10 is also provided with an equivalent electronic control system 12 which includes an equivalent data collection and communication module portion 300 and an equivalent monitoring control portion 400. In the example embodiments to be described herein, although each of the two or more vehicles comprising the various platoons that will be described include the same or equivalent electronic control system 12, 12' the same or equivalent data collection and communication module portion 300, 300' and the same or equivalent monitoring control portion 400,400' other disparate control systems having the functionality to be described herein may equivalently be used as necessary or desired.

In the example embodiment illustrated, the electronic control systems 12, 12' of the respective vehicles 20, 10 are configured for mutually communicating signals and exchanging data between each other, and also for communicating signals and exchanging data with various other communication systems including for example a remote wireless communication system 250 and a remote satellite system 260. These remote systems 250, 260 can provide, for example, global position system (GPS) data to the vehicles 10, 20 as desired. Other information may be provided or exchanged between the vehicles and the remote systems as well such as, for example, fleet management and control data from a remote fleet management facility, or the like (not shown). Although this functionality is provided, the embodiments herein find this remote communication, though useful, not necessarily essential wherein the embodiments herein are directed to monitoring driver behavior directly in accordance with a detected head position of the driver within the vehicle being operated by the driver and for monitoring driver behavior indirectly in accordance with detected aspects of components of the interior of the vehicle being operated by the driver without the need to consult with or act under the direction of or in concert with the remote wireless communication system 250, the remote satellite system 260, the remote fleet management facility, Central Command Center (CCC), a Network Operations Center (NOC), or the like.

In addition to the above, the electronic control systems 12, 12' of each vehicle 10, 20 operates to perform various vehicle-to-(single)vehicle (V2V Unicast) communication (communication between a broadcasting vehicle and a single responding vehicle), as well as various vehicle-to-(multiple) vehicle (V2V Broadcast) communication (communication between a broadcasting vehicle and two or more responding vehicles), and further as well as various vehicle-to-infrastructure (V2I) communication. Preferably, the local V2V Unicast and V2V Broadcast communication follows the J2945 DSRC communications specification. In this regard, the vehicles forming the basic platoon A can communicate with each other locally for self-ordering and spacing into a platoon without the need for input from the CCC in accordance with the embodiments herein. The vehicles forming the basic platoon A can also communicate with one or more other vehicles locally without the need for input from the CCC for negotiating the one or more other vehicles into the platoon in accordance with the embodiments herein. The vehicles forming the basic platoon A can further communicate with a fleet management facility remotely as may be necessary and/or desired for monitoring driver behavior directly in accordance with a detected head position of the driver within the vehicle being operated by the driver and for monitoring driver behavior indirectly in accordance with detected aspects of components of the interior of the vehicle being operated by the driver in accordance with further example embodiments herein.

As noted above, preferably, the local V2V Unicast and V2V Broadcast communication between vehicles as will be described herein follows the J2945 DSRC communications specification. This specification at present, does not define one-to-one vehicle communications. Rather, operationally, each communication-capable vehicle sends the needed information by a broadcast to every other communication-capable vehicle within range, and the receiving vehicle(s) decide if they want to process the received message. For example only vehicles who are Platoon capable and for which the driver has indicated, via a switch or user interface, that joining a platoon is desired, that vehicle will start broadcasting and listening for the Platoon protocol messages. All other vehicles in the area may ignore the platoon information. Accordingly, as will be used herein and for purposes of describing the example embodiments, "V2V Unicast" communication will refer to communication between a broadcasting vehicle and a single responding vehicle, and "V2V Broadcast communication" will refer to communication between a broadcasting vehicle and two or more responding vehicles. It is to be appreciated that "V2V Unicast" communication also refers to one-to-one direct vehicle communications as the J2945 DSRC communications specification is further developed or by use of any one or more other standards, specifications, or technologies now known or hereinafter developed.

Figure 3:
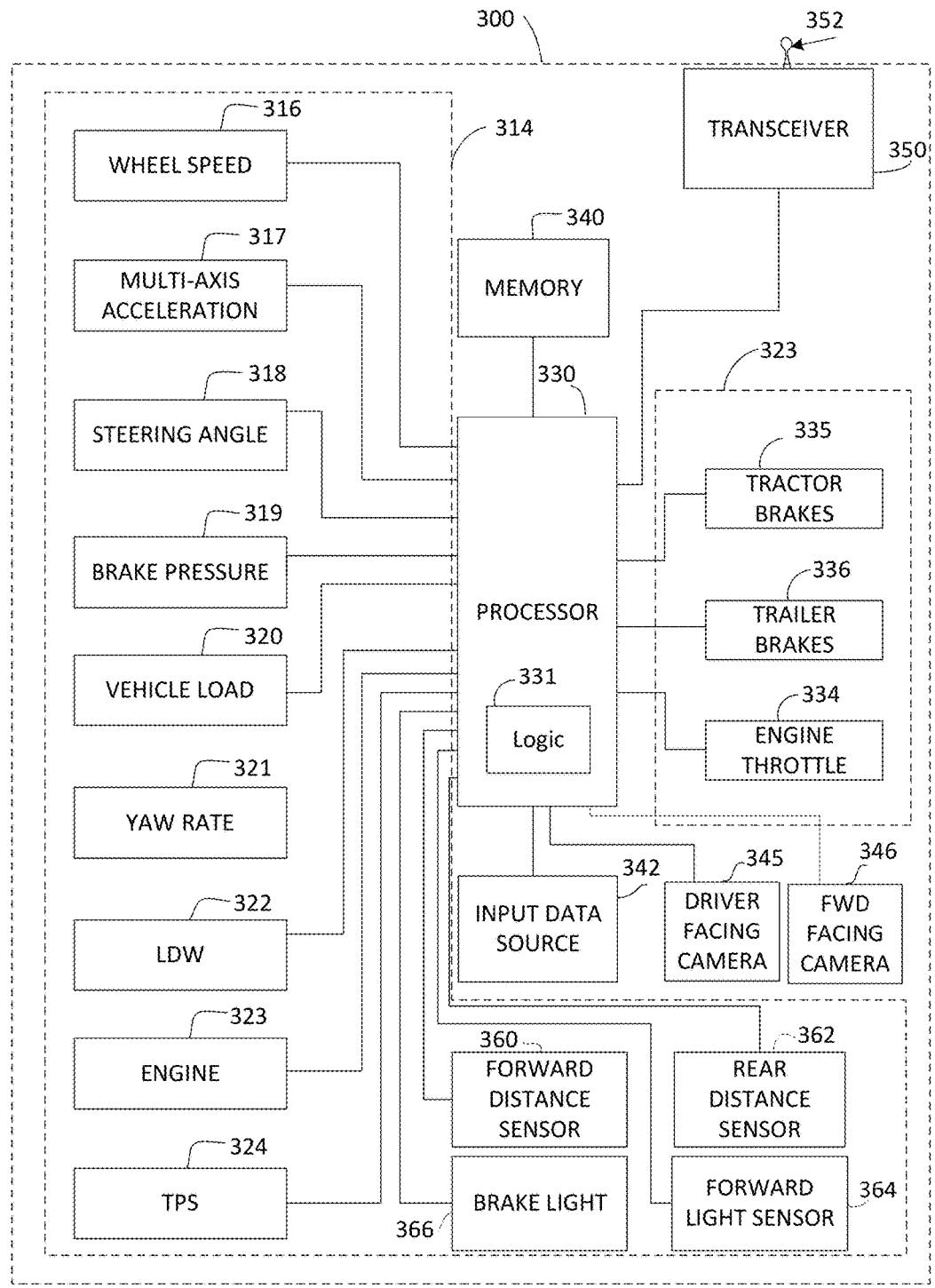
FIG. 3 is a schematic illustration of an exemplary embodiment of a data collection module portion of a driver behavior monitoring system having a driver facing camera according to the example embodiment.

FIG. 3 is a schematic block diagram depiction that illustrates details of the towing vehicle data collection and communication module portion 300 of FIG. 2 in accordance with an example embodiment. According to principles of the example embodiment as illustrated, the towing vehicle data collection and communication module portion 300 may be adapted to detect, monitor, and report a variety of operational parameters and conditions of the commercial vehicle and the driver's interaction therewith, and to selectively intervene and take corrective action as may be needed or desired such as, for example, to maintain vehicle stability or to maintain the vehicle following distance relative to other vehicles within a platoon. In the exemplary embodiment of FIG. 3, the data collection and communication module portion 300 may include one or more devices or systems 314 for providing input data indicative of one or more operating parameters or one or more conditions of a commercial vehicle. For example, the devices 314 may be one or more sensors, such as but not limited to, one or more wheel speed sensors 316, one or more acceleration sensors such as multi-axis acceleration sensors 317, a steering angle sensor 318, a brake pressure sensor 319, one or more vehicle load sensors 320, a yaw rate sensor 321, a lane departure warning (LDW) sensor or system 322, one or more engine speed or condition sensors 323, and a tire pressure (TPMS) monitoring system 324. The towing vehicle data collection and communication module portion 300 may also utilize additional devices or sensors in the exemplary embodiment including for example a forward distance sensor 360, and a rear distance sensor 362. Other sensors and/or actuators or power generation devices or combinations thereof may be used of otherwise provided as well, and one or more devices or sensors may be combined into a single unit as may be necessary and/or desired.

The towing vehicle data collection and communication module portion 300 may also include a logic applying arrangement such as a controller or processor 330 and control logic 331, in communication with the one or more devices or systems 314. The processor 330 may include one or more inputs for receiving input data from the devices or systems 314. The processor 330 may be adapted to process the input data and compare the raw or processed input data to one or more stored threshold values, or to process the input data and compare the raw or processed input data to one or more circumstance-dependent desired value. The processor 330 may also include one or more outputs for delivering a control signal to one or more vehicle systems 323 based on the comparison. The control signal may instruct the systems 323 to intervene in the operation of the vehicle to initiate corrective action, and then report this corrective action to a wireless service (not shown) or simply store the data locally to be used for determining a driver quality. For example, the processor 330 may generate and send the control signal to an engine electronic control unit or an actuating device to reduce the engine throttle 334 and slowing the vehicle down. Further, the processor 330 may send the control signal to one or more vehicle brake systems 335, 336 to selectively engage the brakes. In the tractor-trailer arrangement of the example embodiment, the processor 330 may engage the brakes 336 on one or more wheels of a trailer portion of the vehicle via a trailer pressure control device (not shown), and the brakes 335 on one or more wheels of a tractor portion of the vehicle 12, and then report this corrective action to the wireless service or simply store the data locally to be used for determining a driver quality. A variety of corrective actions may be possible and multiple corrective actions may be initiated at the same time.

The controller 300 may also include a memory portion 340 for storing and accessing system information, such as for example the system control logic 331 and control tuning. The memory portion 340, however, may be separate from the processor 330. The sensors 314 and processor 330 may be part of a preexisting system or use components of a preexisting system. For example, the Bendix® ABS-6™ Advanced Antilock Brake Controller with ESP® Stability System available from Bendix Commercial Vehicle Systems LLC may be installed on the vehicle. The Bendix® ESP® system may utilize some or all of the sensors described in FIG. 3. The logic component of the Bendix® ESP® system resides on the vehicle's antilock brake system electronic control unit, which may be used for the processor 330 of the present invention. Therefore, many of the components to support the towing vehicle controller 330 of the present invention may be present in a vehicle equipped with the Bendix® ESP® system, thus, not requiring the installation of additional components. The towing vehicle controller 330, however, may utilize independently installed components if desired. Further, an IMX.6 processor separate from the ESP system may execute the functions described herein.

The data collection and communication module portion 300 of the towing vehicle controller 12 may also include a source of input data 342 indicative of a configuration/condition of a commercial vehicle. The processor 330 may sense or estimate the configuration/condition of the vehicle based on the input data, and may select a control tuning mode or sensitivity based on the vehicle configuration/condition. The processor 330 may compare the operational data received from the sensors or systems 314 to the information provided by the tuning. The tuning of the system may include, but is not be limited to: the nominal center of gravity height of the vehicle, look-up maps and/or tables for lateral acceleration level for rollover intervention, look-up maps and/or tables for yaw rate differential from expected yaw rate for yaw control interventions, steering wheel angle allowance, tire variation allowance, and brake pressure rates, magnitudes and maximums to be applied during corrective action.

A vehicle configuration/condition may refer to a set of characteristics of the vehicle which may influence the vehicle's stability (roll and/or yaw). For example, in a vehicle with a towed portion, the source of input data 342 may communicate the type of towed portion. In tractor-trailer arrangements, the type of trailer being towed by the tractor may influence the vehicle stability. This is evident, for example, when multiple trailer combinations (doubles and triples) are towed. Vehicles with multiple trailer combinations may exhibit an exaggerated response of the rearward units when maneuvering (i.e. rearward amplification). To compensate for rearward amplification, the towing vehicle controller 330 may select a tuning that makes the system more sensitive (i.e. intervene earlier than would occur for a single trailer condition). The control tuning may be, for example, specifically defined to optimize the performance of the data collection and communication module for a particular type of trailer being hauled by a particular type of tractor. Thus, the control tuning may be different for the same tractor hauling a single trailer, a double trailer combination, or a triple trailer combination.

The type of load the commercial vehicle is carrying and the location of the center of gravity of the load may also influence vehicle stability. For example, moving loads such as liquid tankers with partially filled compartments and livestock may potentially affect the turning and rollover performance of the vehicle. Thus, a more sensitive control tuning mode may be selected to account for a moving load. Furthermore, a separate control tuning mode may be selectable when the vehicle is transferring a load whose center of gravity is particularly low or particularly high, such as for example with certain types of big machinery or low flat steel bars.

In addition, the controller 300 is operatively coupled with one or more driver facing imaging devices shown in the example embodiment for simplicity and ease of illustration as a single driver facing camera 345 representation of one or more physical video cameras disposed on the vehicle such as, for example, a video camera on each corner of the vehicle, one or more cameras mounted remotely and in operative communication with the controller 330 such as a forward facing camera (FFC) disposed on the vehicle in a manner to record images of the roadway ahead of the vehicle, or, as in the example embodiment, in the cab of a commercial vehicle trained on the driver and/or trained on the interior of the cab of the commercial vehicle. In the example embodiments, driver behavior is monitored directly using the driver facing camera 345 in accordance with a detected head position of the driver within the vehicle being operated by the vehicle, the details of which will be elaborated below. In further example embodiments, the driver behavior is monitored directly using the driver facing camera 345 in accordance with a detected head pose of the driver. For purposes of this description of the example embodiments and for ease of reference, "head pose" is that set of angles describing the orientation of the driver's head, that is, pitch (driver looking down or up), yaw (driver looking left or right), and roll (driver tilting his/her head to the left or right). In still further embodiments, driver behavior is monitored indirectly using the driver facing camera 345 in accordance with detected aspects of components of the interior of the vehicle being operated by the vehicle, the details of which will be elaborated below. The driver facing camera 345 may include an imager available from Ominivision™ as part/model number 10635, although any other suitable equivalent imager may be used as necessary or desired.

Still yet further, the controller 300 may also include a transmitter/receiver (transceiver) module 350 such as, for example, a radio frequency (RF) transmitter including one or more antennas 352 for wireless communication of the automated deceleration requests, GPS data, one or more various vehicle configuration and/or condition data, or the like between the vehicles and one or more destinations such as, for example, to one or more wireless services (not shown) having a corresponding receiver and antenna. The transmitter/receiver (transceiver) module 350 may include various functional parts of sub portions operatively coupled with the platoon control unit including for example a communication receiver portion, a global position sensor (GPS) receiver portion, and a communication transmitter. For communication of specific information and/or data, the communication receiver and transmitter portions may include one or more functional and/or operational communication interface portions as well.

The processor 330 is operative to communicate the acquired data to the one or more receivers in a raw data form, that is without processing the data, in a processed form such as in a compressed form, in an encrypted form or both as may be necessary or desired. In this regard, the processor 330 may combine selected ones of the vehicle parameter data values into processed data representative of higher level vehicle condition data such as, for example, data from the multi-axis acceleration sensors 317 may be combined with the data from the steering angle sensor 318 to determine excessive curve speed event data. Other hybrid event data relatable to the vehicle and driver of the vehicle and obtainable from combining one or more selected raw data items form the sensors includes, for example and without limitation, excessive braking event data, excessive curve speed event data, lane departure warning event data, excessive lane departure event data, lane change without turn signal event data, loss of video tracking event data, LDW system disabled event data, distance alert event data, forward collision warning event data, haptic warning event data, collision mitigation braking event data, ATC event data, ESC event data, RSC event data, ABS event data, TPMS event data, engine system event data, average following distance event data, average fuel consumption event data, and average ACC usage event data. Importantly, however, and in accordance with the example embodiments described herein, the controller 300 is operative to store the acquired image data of the driver and/or of the interior of the vehicle in the memory 340, and to selectively communicate the acquired driver and vehicle interior image data to the one or more receivers via the transceiver 350.

In the example embodiment illustrated, the towing vehicle controllers 12, 12' (FIG. 2) of the respective vehicles of the platoon are configured for mutually communicating signals and exchanging data between each other and between their respective one or more towed vehicles, and also for communicating signals and exchanging data with various other communication systems including for example a remote wireless communication system and a remote satellite system. These remote systems can provide, for example, global position system (GPS) data to the vehicles as desired. Other information may be provided or exchanged between the vehicles and the remote systems as well such as, for example, fleet management and control data may be received from a remote fleet management facility, or the like (not shown), and driver behavior data may be sent to the remote fleet management facility, a remote satellite system, a Network Operations Center (NOC), a Central Command Center (CCC), or the like.

The towing vehicle controller 300 of FIG. 3 is suitable for executing embodiments of one or more software systems or modules that perform trailer brake strategies and trailer braking control methods according to the subject application. The example towing vehicle controller 22 may include a bus or other communication mechanism for communicating information, and a processor 330 coupled with the bus for processing information. The computer system includes a main memory 340, such as random access memory (RAM) or other dynamic storage device for storing information and instructions to be executed by the processor 330, and read only memory (ROM) or other static storage device for storing static information and instructions for the processor 330. Other storage devices may also suitably be provided for storing information and instructions as necessary or desired.

Instructions may be read into the main memory 340 from another computer-readable medium, such as another storage device of via the transceiver 350. Execution of the sequences of instructions contained in main memory 340 causes the processor 330 to perform the process steps described herein. In an alternative implementation, hard-wired circuitry may be used in place of or in combination with software instructions to implement the invention. Thus implementations of the example embodiments are not limited to any specific combination of hardware circuitry and software.

In accordance with the descriptions herein, the term "computer-readable medium" as used herein refers to any non-transitory media that participates in providing instructions to the processor 330 for execution. Such a non-transitory medium may take many forms, including but not limited to volatile and non-volatile media. Non-volatile media includes, for example, optical or magnetic disks. Volatile media includes dynamic memory for example and does not include transitory signals, carrier waves, or the like. Common forms of computer-readable media include, for example, a floppy disk, a flexible disk, hard disk, magnetic tape, or any other magnetic medium, a CD-ROM, any other optical medium, punch cards, papertape, any other physical medium with patterns of holes, a RAM, PROM, and EPROM, a FLASH-EPROM, any other memory chip or cartridge, or any other tangible non-transitory medium from which a computer can read.

In addition and further in accordance with the descriptions herein, the term "logic", as used herein with respect to the Figures, includes hardware, firmware, software in execution on a machine, and/or combinations of each to perform a function(s) or an action(s), and/or to cause a function or action from another logic, method, and/or system. Logic may include a software controlled microprocessor, a discrete logic (e.g., ASIC), an analog circuit, a digital circuit, a programmed logic device, a memory device containing instructions, and so on. Logic may include one or more gates, combinations of gates, or other circuit components.

Figure 4:
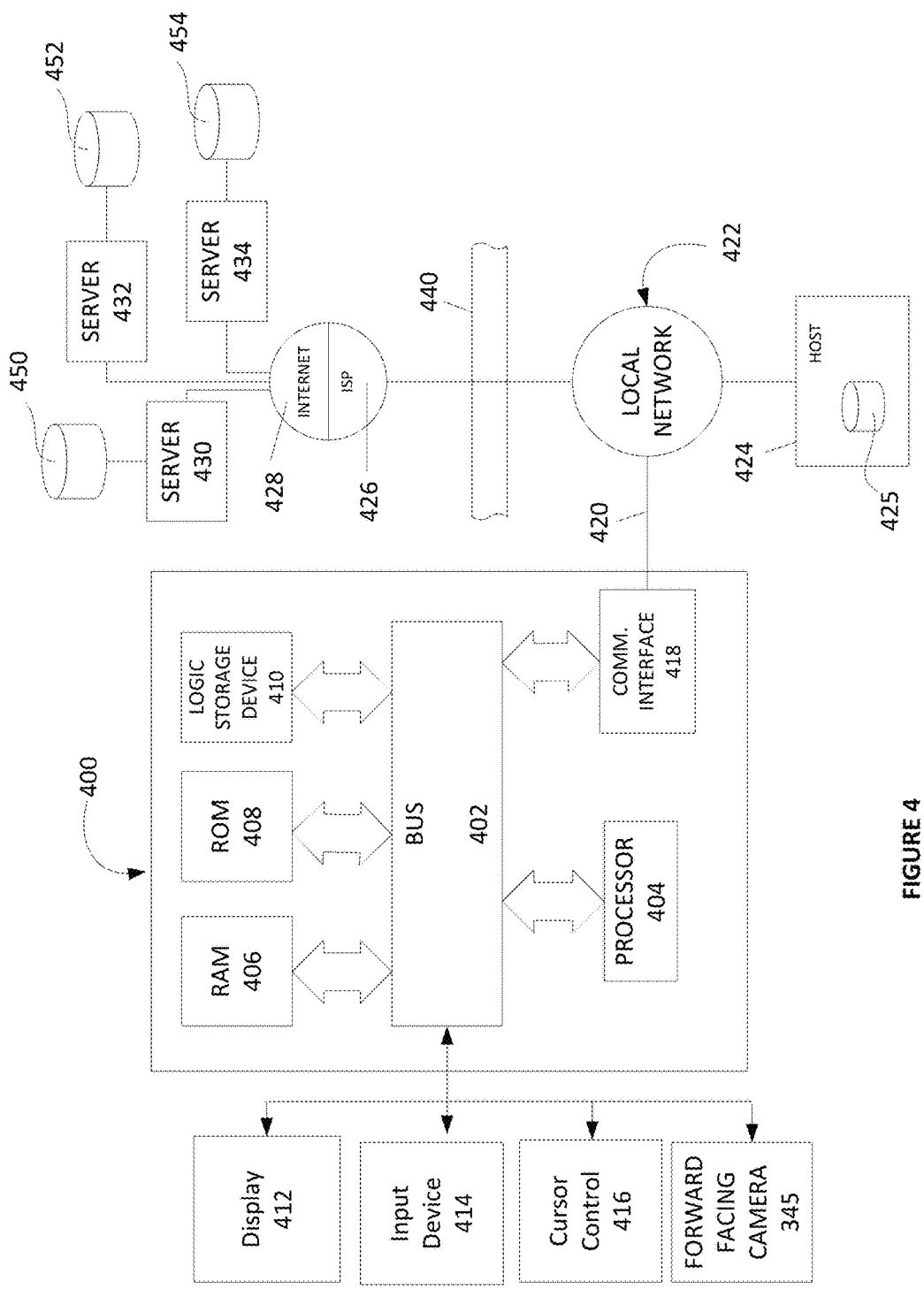
FIG. 4 is a block diagram that illustrates a computer system suitable for monitoring driver behavior directly in accordance with a detected head position of the driver within the vehicle being operated by the driver and for monitoring driver behavior indirectly in accordance with detected aspects of components of the interior of the vehicle being operated by the driver in accordance with an example embodiment.

FIG. 4 is a block diagram that illustrates a driver behavior monitoring computer system 400 suitable for executing embodiments of one or more software systems or modules that perform the driver behavior monitoring and reporting analyses according to the subject application. The example system includes a bus 402 or other communication mechanism for communicating information, and a processor 404 coupled with the bus for processing information. The computer system 400 includes a main memory, such as random access memory (RAM) 406 or other dynamic storage device for storing information and instructions to be executed by the processor 404, and read only memory (ROM) 408 or other static storage device for storing static information and instructions for the processor 404. A logic storage device 410 is also suitably provided for storing instructions for execution by the processor, and other information including for example one or more calibration values of directly monitored parameters of the driver, such as proper driver head position, for example, and/or one or more calibration values of indirectly monitored parameters of the driver, such as proper seat belt usage, for example. In addition, operator interfaces are provided in the form of an input device 414 such as a keyboard or a voice recognition input including a microphone and logic transforming human voice sounds into computer commands, a human readable display 412 for presenting visible information to the driver, and a cursor control 416 such as a joystick or mouse or the like.

The example embodiments described herein are related to the use of the computer system 400 for accessing, aggregating, manipulating and displaying information from one or more resources such as, for example, from the driver facing camera 345.

According to one implementation, information from the driver facing camera 345 is provided by computer system 400 in response to the processor 404 executing one or more sequences of one or more instructions contained in main memory 406. Such instructions may be read into main memory 406 from another computer-readable medium, such as logic storage device 410. The logic storage device 410 may store one or more subsystems or modules to perform the direct driver behavior monitoring as set forth herein and/or one or more subsystems or modules to perform the indirect driver behavior monitoring as set forth herein. Execution of the sequences of instructions contained in main memory 406 causes the processor 404 to perform the process steps described herein. In an alternative implementation, hard-wired circuitry may be used in place of or in combination with software instructions to implement the invention. Thus implementations of the example embodiments are not limited to any specific combination of hardware circuitry and software.

In accordance with the descriptions herein, the term "computer readable medium" as used herein refers to any non-transitory media that participates in providing instructions to the processor 404 for execution. Such a non-transitory medium may take many forms, including but not limited to volatile and non-volatile media. Nonvolatile media includes, for example, optical or magnetic disks. Volatile media includes dynamic memory for example and does not include transitory signals, carrier waves, or the like. Common forms of computer-readable media include, for example, a floppy disk, a flexible disk, hard disk, magnetic tape, or any other magnetic medium, a CDROM, any other optical medium, punch cards, papertape, any other physical medium with patterns of holes, a RAM, PROM, and EPROM, a FLASH-EPROM, any other memory chip or cartridge, or any other tangible non-transitory medium from which a computer can read.

In addition and further in accordance with the descriptions herein, the term "logic", as used herein with respect to the Figures, includes hardware, firmware, software in execution on a machine, and/or combinations of each to perform a function(s) or an action(s), and/or to cause a function or action from another logic, method, and/or system. Logic may include a software controlled microprocessor, a discrete logic (e.g., ASIC), an analog circuit, a digital circuit, a programmed logic device, a memory device containing instructions, and so on. Logic may include one or more gates, combinations of gates, or other circuit components.

The driver behavior monitoring computer system 400 includes a communication interface 418 coupled to the bus 402 which provides a two-way data communication coupling to a network link 420 that is connected to local network 422. For example, communication interface 418 may be an integrated services digital network (ISDN) card or a modem to provide a data communication connection to a corresponding type of telephone line. As another example, communication interface 418 may be a local area network (LAN) card to provide a data communication connection to a compatible LAN. Wireless links may also be implemented. In any such implementation, communication interface 418 sends and receives electrical, electromagnetic or optical signals that carry digital data streams representing various types of information.

Network link 420 typically provides data communication through one or more networks to other data devices. For example, network link 420 may provide a connection through local network 422 to a host computer 424 supporting a database 425 storing internal proprietary data and/or to data equipment operated by an Internet Service Provider (ISP) 426. ISP 426 in turn provides data communication services through the Internet 428. Local network 422 and Internet 428 both use electric, electromagnetic or optical signals that carry digital data streams. The signals through the various networks and the signals on network link 420 and through communication interface 418, which carry the digital data to and from the driver behavior monitoring computer system 400, are exemplary forms of carrier waves transporting the information.

The driver behavior monitoring computer system 400 can send messages and receive data, including program code, through the network(s), network link 420 and communication interface 418. In the Internet-connected example embodiment, the driver behavior monitoring computer system 400 is operatively connected with a plurality of external public, private, governmental or commercial servers (not shown) as one or more wireless services (not shown) configured to execute a web application in accordance with the example embodiment to be described below in greater detail. In the example embodiment shown, the first server 430 is coupled with a database 450 storing selected data received by a first wireless service such as for example data from a first telematics supplier, the second first server 432 is coupled with a database 452 storing selected data received by a second wireless service such as for example data from a second telematics supplier, and the third server 434 is coupled with a database 454 storing selected proprietary data and executable code for performing the web application. The driver behavior monitoring computer system 400 is operative to selectively transmit data to the respective databases 450, 452, 454 through Internet 428, ISP 426, local network 422 and communication interface 418, and/or to receive selected data pushed from the databases 450, 452, 454, or by both means in accordance with the example embodiments. The received data is processed executed by the processor 404 as it is received, and/or stored in storage device 410, or other non-volatile storage for later processing or data manipulation.

Although the driver behavior monitoring computer system 400 is shown in FIG. 4 as being connectable to a set of three (3) servers, 430, 432, and 434, those skilled in the art will recognize that the driver behavior monitoring computer system 400 may establish connections to multiple additional servers on Internet 428. Each such server in the example embodiments includes HTTP-based Internet applications, which may provide information to the driver behavior monitoring computer system 400 upon request in a manner consistent with the present embodiments.

Selectively locating the proprietary commercial data in database 425 within the firewall 440 is advantageous for numerous reasons including enabling rapid comprehensive local queries without substantial network overhead. However, it is important to maintain the accuracy of the data by performing update or refresh operations on a schedule based on the characteristics of the desired data or on the data requirements of a particular query.

Figure 4A:
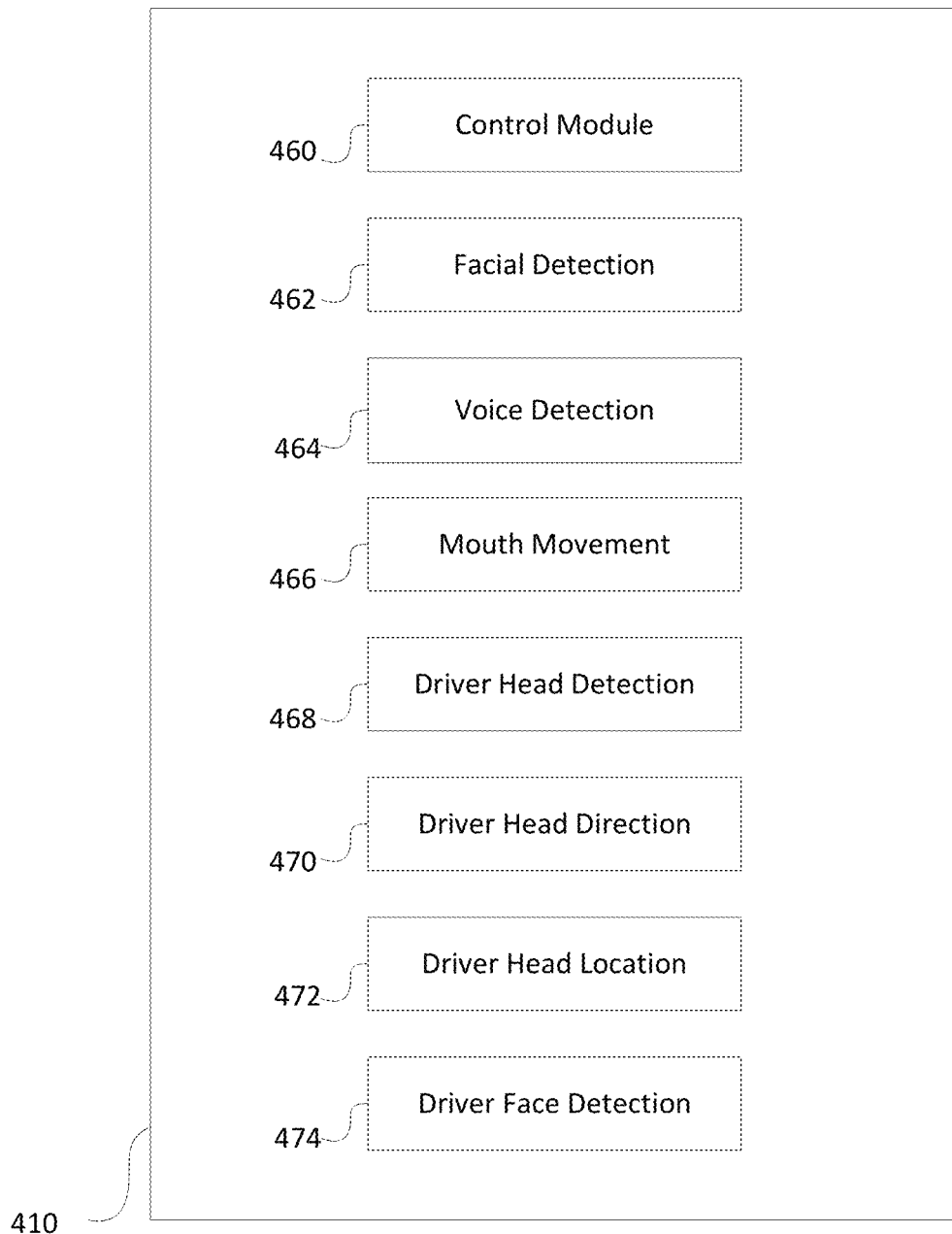
FIG. 4a is a block diagram that illustrates executable logic components of the driver behavior monitoring system having a driver facing camera according to the example embodiment.

The driver behavior monitoring computer system 400 suitably includes several subsystems or modules to perform the direct and/or indirect driver behavior monitoring as set forth herein. A primary purpose of the subject application is to provide improved monitoring of driver behavior which allows fleet managers or the like to better manage their driver operators. In this regard, FIG. 4a is a block diagram that illustrates executable logic components of the driver behavior monitoring system having a driver facing camera according to the example embodiment. With reference now to that Figure, logic stored in the storage device 410 (FIG. 4) is executable by the processor to perform the driver behavior monitoring and reporting in accordance with the embodiments herein. The logic stored in the storage device 410 includes control logic 460 control logic stored in the non-transient memory device. The control logic is executable by the processor to process image data to determine an operational value of a parameter of a monitored condition of the associated vehicle, perform a comparison between a recommended value range of the parameter of the monitored condition of the associated vehicle and the operational value of the parameter of the monitored condition of the associated vehicle, and determine a state of vehicle operation compliance in accordance with a result of the comparison between the recommended value range and the operational value of the parameter of the monitored condition of the associated vehicle. The processor of the system may selectively generate result data in accordance with the result.

The logic stored in the storage device 410 further includes facial detection logic 462 stored in the non-transient memory device. The facial detection logic is executable by the processor to process image data to locate one or more face candidate areas of an image captured by the imaging device 345 likely above a predetermined threshold stored in the non-transient memory device of the system to be representative of a corresponding one or more human faces in the associated vehicle, and generate a set of face descriptors for each of the one or more face candidate areas. The facial detection logic is further operable to process the image data to determine an identify of a human person associated with the set of face descriptors for each of the one or more face candidate areas.

The logic stored in the storage device 410 further includes voice detection logic 464. The voice detection logic 464 is executable by the processor to identify of a human person associated with a set of face descriptors for each of one or more face candidate areas in accordance with received voice data representative of a recorded voice of one or more human passengers corresponding to the one or more face candidate areas.

The logic stored in the storage device 410 further includes mouth movement logic 466. The mouth movement logic 466 is executable by the processor to identify of a human person associated with a set of face descriptors for each of one or more face candidate areas in accordance with voice data in combination with received mouth movement data representative of recorded mouth movement images of one or more human passengers corresponding to the one or more face candidate areas.

The logic stored in the storage device 410 further includes driver head detection logic 468. The driver head detection logic 468 is executable by the processor to process image data to locate/determine a head candidate area of an image captured by the imaging device 345 likely above a predetermined threshold stored in the non-transient memory device to be representative of a head of an associated driver disposed in the associated vehicle, and tag a portion of the image data corresponding to the head candidate area located/determined by the driver head detection logic as driver head image data.

The logic stored in the storage device 410 further includes driver head direction logic 470. The driver head direction logic is executable by the processor to process driver head image data to determine a facing direction of a head of an associated driver, and generate driver head facing direction data, the driver head facing direction data being representative of the determined facing direction of the head of the associated driver.

The logic stored in the storage device 410 further includes driver head location logic 472. The driver head location logic is executable by the processor to process driver head image data together with vehicle geometry data and imaging device position data to determine a location of a driver's head relative to one or more controls structures of an associated vehicle, and generate driver's head location data, the driver's head location data being representative of the determined location of the head of the associated driver relative to the one or more controls structures of the associated vehicle.

The logic stored in the storage device 410 further includes driver face detection logic 474. The driver face detection logic is executable by the processor to process image data together with vehicle geometry data and imaging device position data to determine one or more foreground objects in the image data and one or more background objects in the image data. The determined one or more foreground objects in the image data are disposed in the associated vehicle between the imaging device and the one or more background objects in the image data. The driver face detection logic is executable by the processor to process a portion of the image data corresponding to the determined one or more foreground objects in the image data to selectively determine, from the image data, a face of the driver of the associated vehicle, and generate a one of: driver's facial characteristic data representative of the selectively determined face of the associated driver, or impeded image data representative of an inability of the driver face detection location logic to selectively determine the face of the driver of the associated vehicle from the image data. The driver face detection logic is further executable by the processor to process the driver's head location data and a facial normal vector to selectively determine, from the image data, a face of the driver of the associated vehicle, and generate a one of: driver's facial characteristic data representative of the selectively determined face of the associated driver, or impeded image data representative of an inability of the driver face detection location logic to selectively determine the face of the driver of the associated vehicle from the image data.

Figure 5A:
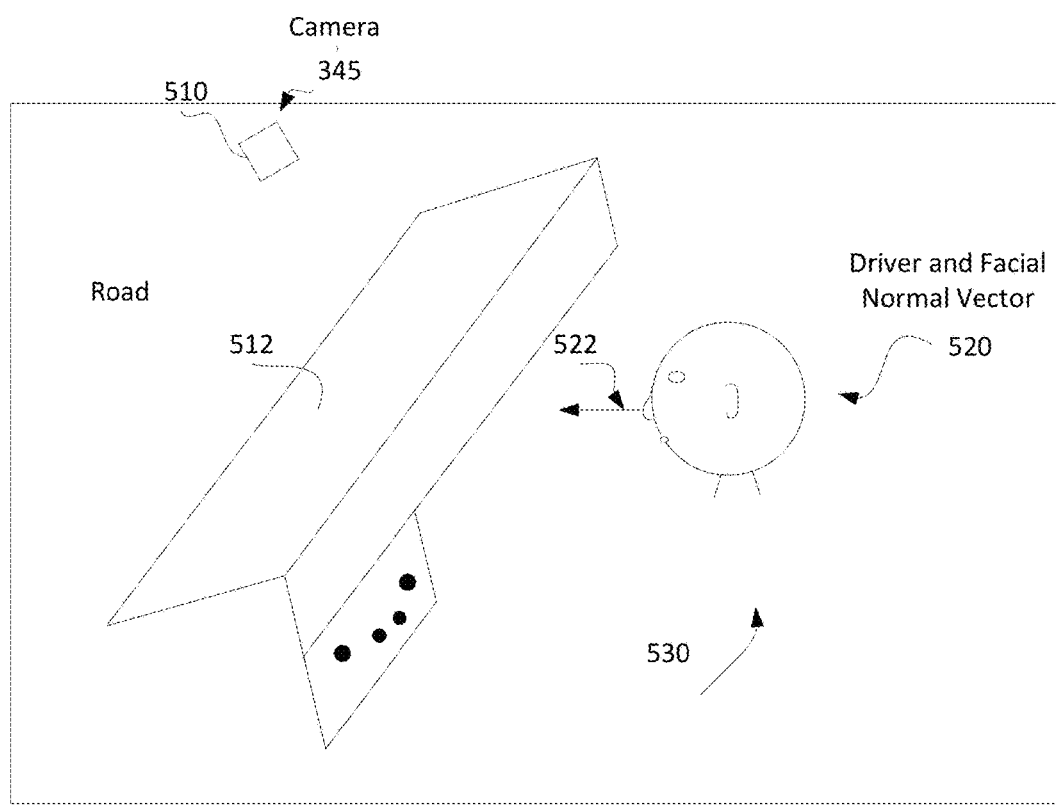
FIG. 5a is a schematic diagram showing a driver facing imager in accordance with an example embodiment disposed in the cab of an associated vehicle in a fixed location at the upper top of a windshield of the associated vehicle.

The driver facing camera 345 of the example embodiment is, preferably, a driver facing video camera 510 disposed as shown in FIG. 5a at the upper top of the windshield 512 of the associated vehicle. In that position, the driver facing video camera (DFC) 510 is best able to image the head 520 of the driver, and the area 530 surrounding the driver while also simultaneously giving an advantageous view of the road ahead for the forward facing camera. An alternative embodiment with separate driver-facing 345 and forward-facing 346 cameras is possible, in which case the forward facing camera (FFC) 346 is best placed high on the windshield as shown, and the driver facing camera 345 may be disposed in a separate housing and placed ahead on the dashboard or to the side of the driver, either low on the dashboard or high on the windshield as shown. Applicable unimpeded view requirements for vehicles are typically fulfilled by these locations. A central point of view is best for obtaining a full cabin image. In accordance with embodiments herein, one or more still and/or video images of the driver's head are used to directly monitor the driver behavior in ways to be described in greater detail below and, correspondingly, in accordance with embodiments herein, one or more still and/or video images of the area 530 surrounding the driver are used to directly monitor the driver behavior in ways to be described in greater detail below.

Figure 5B:
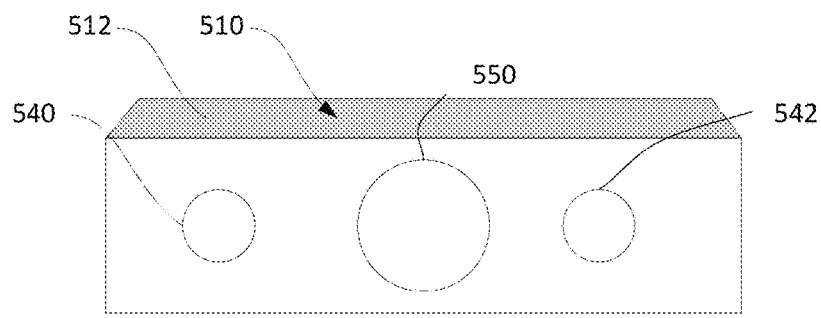
FIG. 5b is a diagram of an embodiment of the driver facing imager of FIG. 5a formed as a driver facing camera in accordance with an example embodiment.

FIG. 5b is a diagram showing the driver facing video camera 510 in accordance with an example embodiment herein. As shown, the driver facing video camera 510 includes a housing member 512 supporting a pair of first 540 and second 542 lights disposed on opposite sides of a centrally located camera device 550. The pair of first and second lights 540, 542 are, preferably infrared (IR) lights, such as IR LEDs, so that the driver and the area in the vehicle surrounding the driver may be illuminated for purposes of recording images of the drier and the areas surrounding the driver by the camera device 550 without impeding the driver during operation of the vehicle such as by distracting or blinding the driver, or the like. The camera 550 is preferably angled somewhat toward the driver in order that the beneficial optical characteristics, such as higher resolution, near the central axis of the lens are favored. In the embodiment, the lens horizontal field of view is wide enough to see both the driver and passenger. The lens horizontal field of view further is wide enough to see the driver, any passenger(s), and the inside of the cab of the vehicle to a large extent including for example the vehicle side view mirrors as will be described in detail below.

Figure 6A:
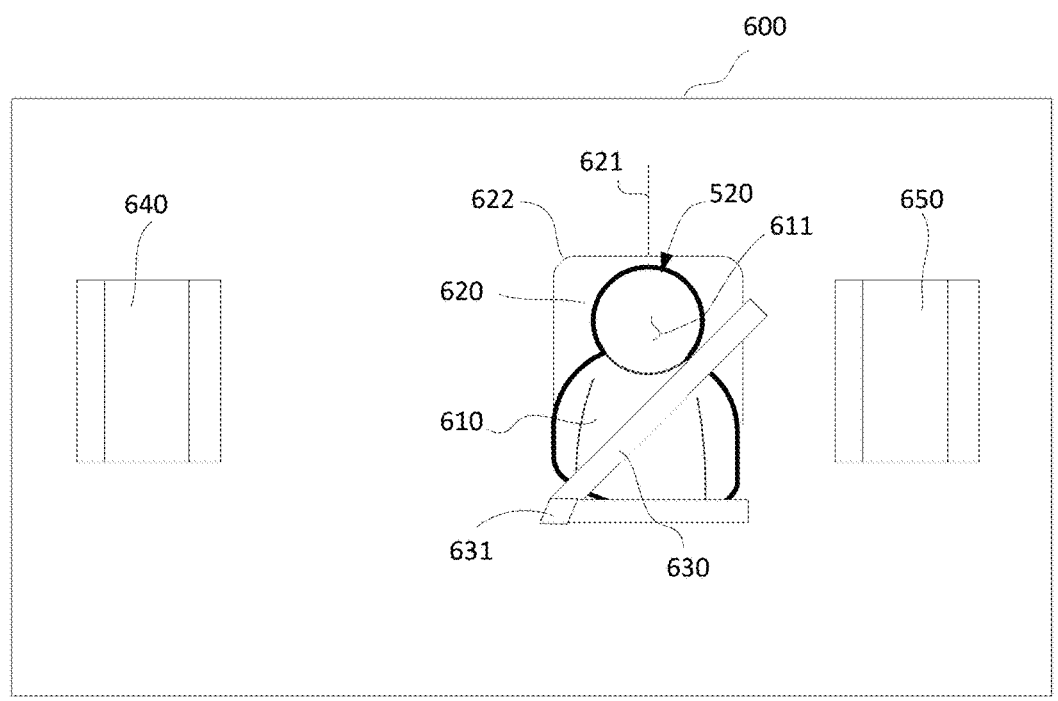
FIG. 6a is a first example of a calibration image generated by the driver facing camera of FIG. 5b and obtained during a first calibration operation of the driver behavior monitoring system.

FIG. 6a is a calibration image 600 obtained from the driver facing camera 345 showing an image of a driver 610, an image of a driver's seat 620 with the driver disposed thereon, an image of a properly worn seatbelt 630, an image of a passenger side mirror 640, and an image of a driver's side view mirror 650. The calibration image 600 may be obtained by imaging a human driver properly located in the seat, with the seatbelt being properly worn and with the driver's head being disposed in a direction to look directly at the road ahead. In the embodiments herein, one or more portions of the calibration image 600 may be used for monitoring the driver's behavior directly using the driver facing camera 345 in accordance with a detected head position of the driver within the vehicle being operated by the vehicle, and for monitoring the driver's behavior indirectly using the driver facing camera 345 in accordance with detected aspects of components of the interior of the vehicle being operated by the vehicle such as, for example, detected aspects of the driver's seat 620, the seatbelt 630, the left and right side view mirrors 640, 650 and other things including the absence of any passengers in the calibration image 600. In accordance with the embodiments, the calibration image 600 may be obtained by imaging a human driver properly located in the seat while the vehicle is moving at higher speeds such as, for example, over 40 mph, during which driver head pose data may be collected, thereby determining the driver's head "straight ahead" disposition. It may be assumed in the embodiment that the average or most common (mode) of driver's head angles correspond to the 'looking straight ahead, at the road' values for this driver. It is to be noted that a yaw angle of zero may be taken as either looking directly at the camera, so a frontal view of the driver, or may be taken as when looking straight ahead, that is, (typically) in line with the longitudinal axis of the driver's seat, so facing forward, and the road.

Figure 6B:
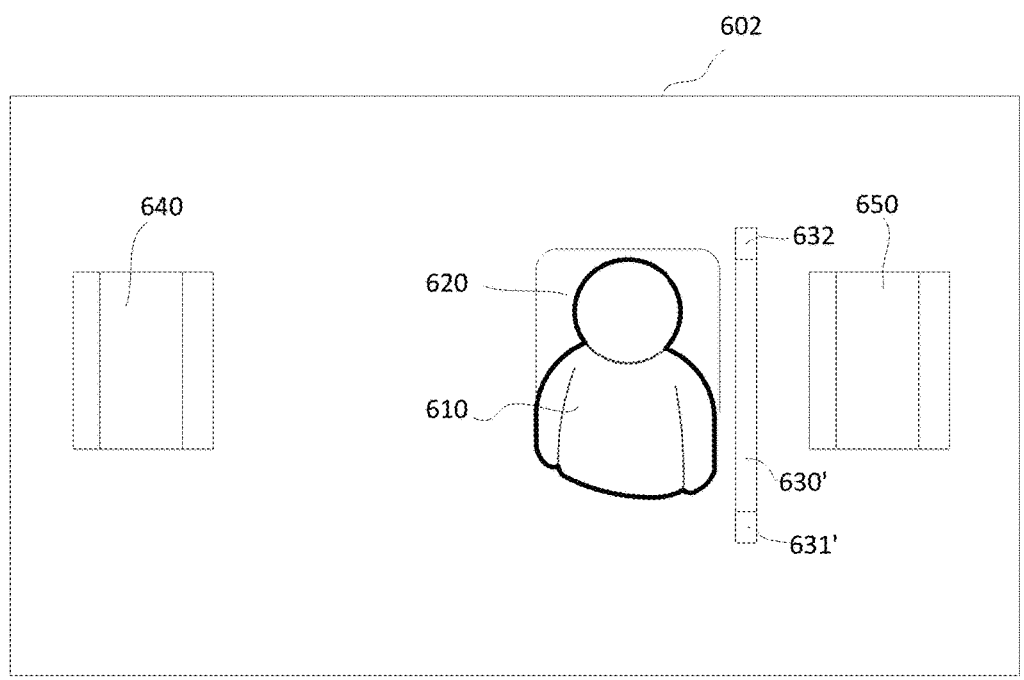
FIG. 6b is an example of a second calibration image generated by the driver facing camera of FIG. 5b and obtained during a second calibration operation of the driver behavior monitoring system.

FIG. 6b is a calibration image 602 obtained from the driver facing camera 345 showing an image of the driver 610, an image of a driver's seat 620 with the driver disposed thereon, an image of an improperly worn seatbelt 630', an image of a passenger side mirror 640, and an image of a driver's side view mirror 650. The calibration image 602 may be obtained by positioning the human driver in the seat, with the seatbelt improperly (not) worn and with the driver's head being disposed in a direction to look directly at the road ahead. In the embodiments herein, one or more portions of the calibration image 602 may be used for monitoring the driver's behavior directly using the driver facing camera 345 in accordance with a detected head position of the driver within the vehicle being operated by the vehicle, and for monitoring the driver's behavior indirectly using the driver facing camera 345 in accordance with detected aspects of components of the interior of the vehicle being operated by the vehicle such as, for example, detected aspects of the driver's seat 620, the improperly worn seatbelt, the seatbelt buckle 632, the left and right side view mirrors 640, 650 and other things including the absence of any passengers in the calibration image 602.

Figure 7:
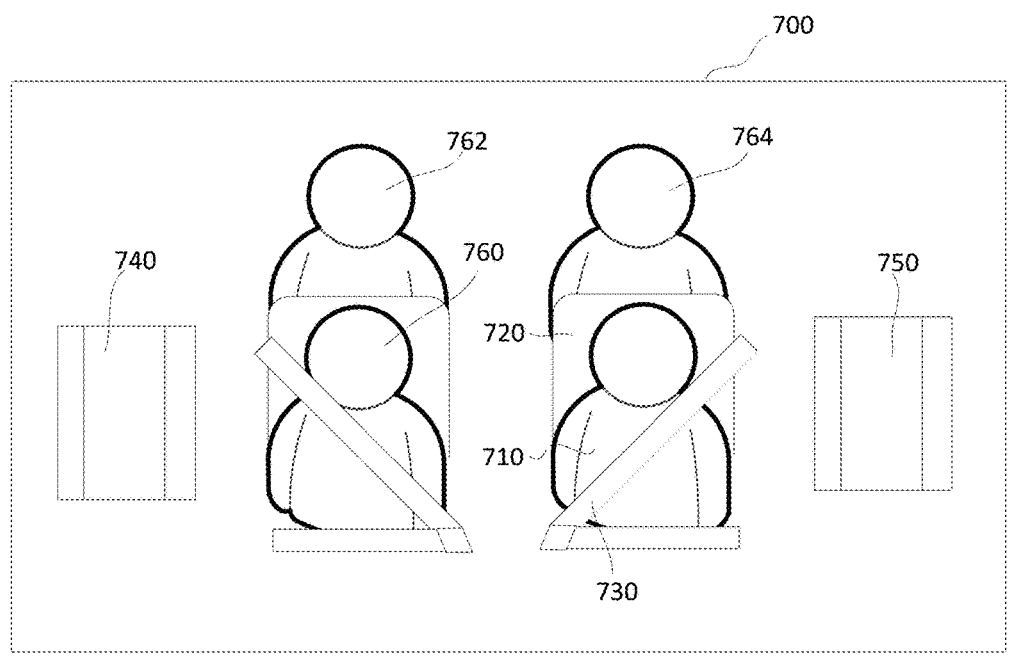
FIG. 7 is an example of an image generated by the driver facing camera of FIG. 5b and obtained by the driver behavior monitoring system during operation of the associated vehicle.

FIG. 7 is an example of an image 700 obtained from the driver facing camera 345 during operation of the vehicle such as, for example, while the vehicle is being driven, showing an image of the driver 710, an image of the driver's seat 720 with the driver disposed thereon, an image of the seatbelt 730, an image of the passenger side mirror 740, and an image of the driver's side view mirror 750. The image 700 is in accordance with an embodiment herein, obtained continuously as a video while the associated vehicle is being driven by the driver and stored into the memory device as video data. The image 700 may also be obtained continuously as a sequence of photo images taken over time and at predetermined intervals selected for example based on the speed or other operational characteristics of the vehicle while it is being driven by the driver, and stored into the memory device 340 as sequenced photo image data. In the embodiments herein, one or more portions of the image 700 may be used for monitoring the driver's behavior directly using the driver facing camera 345 in accordance with a detected head position of the driver within the vehicle being operated by the vehicle, and for monitoring the driver's behavior indirectly using the driver facing camera 345 in accordance with detected aspects of components of the interior of the vehicle being operated by the vehicle such as, for example, detected aspects of the driver's seat 720, the improperly worn seatbelt, the seatbelt buckle 732, the left and right side view mirrors 740, 750 and other things including the presence of any passengers 760, 762, and 764 in the image 700.

As noted above, in embodiments herein, systems and methods are provided using the driver facing camera 345 for monitoring driver behavior directly in accordance with a detected head position of the driver within the vehicle being operated by the driver. The driver behavior being monitored includes, in the various embodiments, one or more of:
1) a verification of a proper usage by the driver of the driver's side view mirror 750 and/or of the passenger's side view mirror 740;
2) a verification of proper attention being paid by the driver to the road ahead;
3) a verification of the driver not excessively reaching for items beyond his considered to be safe grasp space, preferably an extent of a reach maneuver capable of being performed by the driver without excessive body movement; and
4) a verification of a driver's head pose distribution metric.

The verification of the proper usage by the driver of the driver's side view mirror 750 and/or of the passenger's side view mirror 740, of the proper attention being paid by the driver to the road ahead, of the driver not excessively reaching for items beyond his considered to be safe wingspan, and of the driver's head pose distribution metric may be singularly and/or collectively reported to an associated fleet management network, stored locally, or any combination of remote singular/collective reporting and/or local storing. The verification of the proper attention being paid by the driver to the road ahead is used in an embodiment to adapt a Lane Departure Warning (LDW) system to a determined driver road attention value.

In further embodiments herein and as noted above, systems and methods are provided using the driver facing camera 345 for monitoring driver behavior indirectly in accordance with detected aspects of components of the interior of the vehicle being operated by the driver. The driver behavior being monitored includes in the various embodiments one or more of:
1) a verification of a proper usage by the driver of a seatbelt;
2) a verification of the driver having proper hand placement on the steering wheel; and
3) a verification that the driver has either no passengers, a proper limit of passengers, and/or a verification that the detected passengers are authorized passengers.

Using Forward Facing Camera (DFC) to Monitor and Report Driver Behavior

As noted above, the example embodiments herein are provided for monitoring and reporting driver behavior directly using a driver-facing camera in accordance with a detected head position of the driver within the vehicle being operated by the driver, and for monitoring and reporting driver behavior indirectly using a driver-facing camera in accordance with detected aspects of components of the interior of the vehicle being operated by the driver. In the direct driver behavior monitoring, the driver and/or the driver's head is located in the image obtained of the vehicle interior, and parameters of various driver behavior metrics are determined in accordance with the located driver head in the image. In the indirect driver behavior monitoring, one or more components of the vehicle such as for example a seat belt or a steering wheel are located in the image obtained of the vehicle interior, and parameters of various driver behavior metrics are determined by inference in accordance with the located one or more components of the vehicle in the image.

Figure 8:
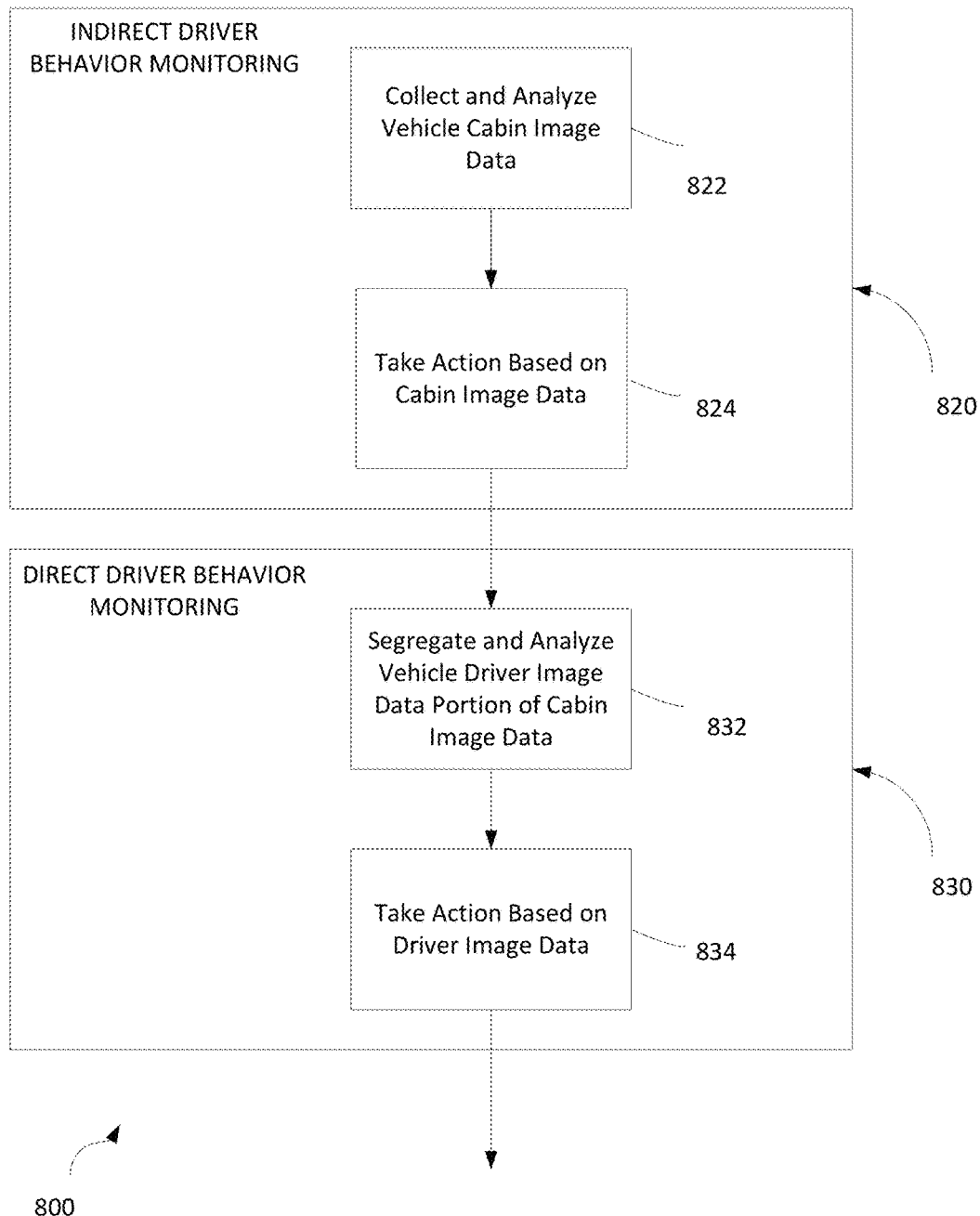
FIG. 8 is a flow diagram showing a method of operating a driver behavior monitoring system having a driver facing camera for implementing a driver behavior monitoring and reporting strategy in accordance with an example embodiment.

FIG. 8 is a flow diagram showing a method 800 of implementing a driver behavior monitoring and reporting strategy in accordance with an example embodiment including a first set of steps 820 for monitoring driver behavior indirectly using a driver-facing camera in accordance with detected aspects of components of the interior of the vehicle being operated by the vehicle, and further including a second set of steps 830 for monitoring driver behavior directly using the driver-facing camera in accordance with a detected head position of the driver within the vehicle being operated by the vehicle. In the first set of steps 820 indirectly monitoring the driver behavior, vehicle cabin image data is collected and then analyzed at step 822. In the embodiment, the vehicle cabin image data is representative of the image 700 (FIG. 7) obtained from the driver facing camera 345 during operation of the vehicle. Thereafter, one or more action(s) are taken in step 824 based on the collected and analyzed cabin image data. In the embodiments described, the indirect driver behavior monitoring does not rely on finding the location, position or pose of the driver's head in the image, but rather infers the driver's behavior from portions the image relating to components of the vehicle being used by the driver, preferably being used in accordance with a good driver behavior such as for example a proper wearing of seatbelts.

Somewhat similarly in the second set of steps 830 directly monitoring the driver behavior, a portion of the vehicle cabin image data relating to the vehicle driver image is segregated at step 832 from the vehicle cabin image data collected at step 822. The segregated portion may be related to the driver's head, the driver's seat, the seatbelt, the seatbelt buckle, the one or more passengers, or any other items selected for monitoring as may be necessary and/or desired. Thereafter, one or more action(s) are taken in step 834 based on the vehicle driver image portion of the cabin image data.

I. Using DFC to Indirectly Monitor and Report Driver Behavior

Driver behavior may be monitored, in accordance with embodiments described herein by using a driver-facing camera to detect and monitor aspects of components of the interior of the vehicle being operated by the vehicle, then inferring driver behavior in accordance with the monitored aspects of components of the interior of the vehicle. The indirectly monitored driver behavior is collected and stored locally in the vehicle and, in embodiments, may be reported to a central fleet management system.

Passenger Detection and Counting

Commercial vehicle drivers may have one or more unauthorized passengers accompanying the driver in the vehicle. Commercial vehicle fleet policy often forbids or limits the passengers allowed to be present in their vehicles. It would therefore be desirable to detect if any unauthorized passengers are present in the vehicle. It would also be desirable to detect how many passengers are present in the vehicle. It would further be desirable to identify the detected passengers present in the vehicle.

Figure 9:
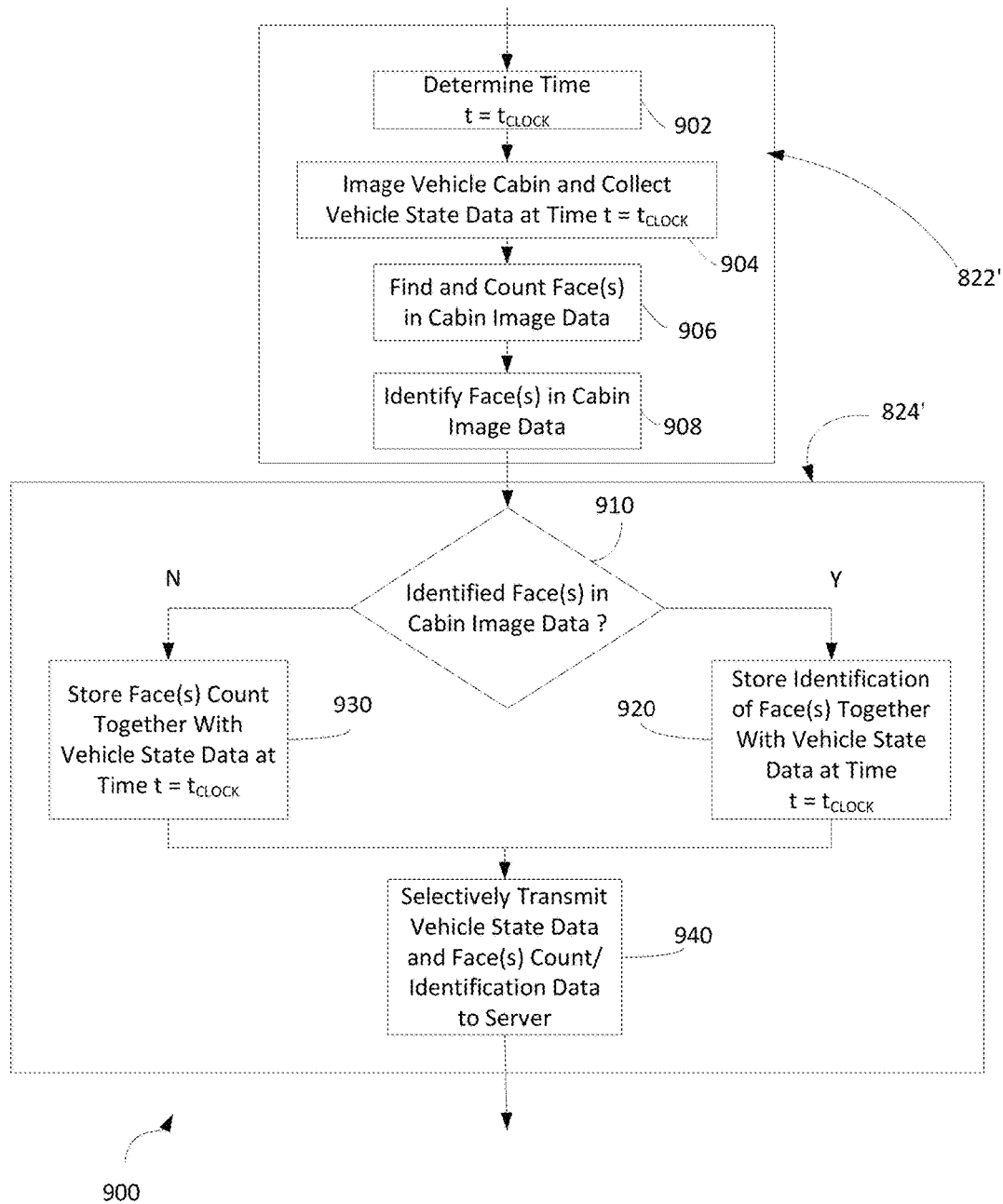
FIG. 9 is a flow diagram showing a method of operating a driver behavior monitoring system having a driver facing camera for implementing a passenger detecting, counting, monitoring, and reporting strategy in accordance with an example embodiment.

The example embodiment as shown for example in FIG. 9 provides a system and method for detecting, counting, and identifying such passengers. An advantage of the example embodiment is an ability to enforce fleet policy by ensuring that the driver adheres to fleet policy, and that any fleet policy violations are appropriately logged and reported.

In the embodiment of the method 900 shown in FIG. 9, the cabin image data collection portion 822' includes a step 902 determining a time of the image of the cabin, and a step 904 collecting vehicle operational data such as, for example, vehicle speed data or the like. In step 906 the logic of the system finds one or more faces in the cabin image data, and further, counts the number of faces found. In step 908 of the cabin image data collection portion 822', the logic of the system is executed to attempt to identify the one or more faces found in the cabin image data.

Next in the method 900 shown in FIG. 9, the action taking portion 824' includes a step 910 of determining whether any of the faces located in the cabin image data can be or have been identified. If one or more of the faces are identified, the method 900 in step 920 stores an identification of the faces together with the vehicle status data collected in step 904. On the other hand, If any of the faces are not identified, the method 900 in step 930 stores the determined face count together with the vehicle status data collected in step 904.

Further in the method 900 of the embodiment, one or more of the identification of the faces, the determined face count, and/or the vehicle status data is stored locally in the memory of the system at the vehicle or is transmitted in step 940 to a central fleet management system.

In accordance with the example embodiment, the driver facing camera 345 uses wide angle camera views to obtain an image 700 of the cabin of the commercial vehicle. This wide angle image is preferably then undistorted to remove wide angle lens effects. The undistorted cabin image data is inspected by the logic 330 to first locate faces in the image, and then to count the located faces. Face detection algorithms, such as that of Viola-Jones, may be used to locate candidate camera image areas that may be faces. Face descriptors are generated for these located face candidate camera image areas. The number of detected face areas, overlapping and not, and the corresponding face descriptors are generated. A threshold for facial similarity is set, below which the faces are declared to be the same (via similar face descriptor vectors). Similarly, the detected faces may be compared with previously stored face descriptor vector data for drivers and passengers allowed to be in the vehicle. The face descriptor vector data of authorized drivers and permitted passengers may be stored locally in the driver behavior monitoring system or remotely such in one or more databases associated with the servers 142 (FIG. 1), of the central fleet management system.

Tracking logic executed by the processor may be used to associate facial measurements with previous locations, thereby allowing person identification logic executed by the processor with a focus on multiple areas. The identified (or not) persons are transmitted to the one or more Fleet Management servers 142 (FIG. 1), together with vehicle state data preferably sampled coincidently with person(s) identification. This may occur either while the vehicle is moving or while it is stationary or standing still.

The identified faces are compared with either an in-vehicle database, or transmitted to a central management system 142 with a similar database 150 (FIG. 1). Should a person not registered as allowed in the vehicle be identified, a first pass is made at identifying said person(s). If the identified one or more person(s) is/are known to the database, a first type of event processing is performed by the driver behavior monitoring computer system. However, if the identified one or more person(s) is/are unknown to the database, a second type of event processing is performed by the driver behavior monitoring computer system.

The information is selectively transmitted to the fleet management system for analysis by a fleet manager 160 (FIG. 1) or the like. The information collected, analyzed, and transmitted may include any one or more or others of: how many passenger(s) (i.e. not driving) are present in a vehicle, whether these passengers are known or not, facial descriptors may be sent to an associated fleet management system if the identified passengers are not known, the gender of the passengers, a time of day of image collection, a location of the vehicle at the time the cabin image was collected, passenger snapshot(s), and vehicle interior/cabin snapshot(s) as may be deemed necessary and/or desired. Unknown passengers may also be recorded by a microphone of the input device 414 (FIG. 4) which may be present in the system when it is determined that the passengers are speaking.

Figure 9A:
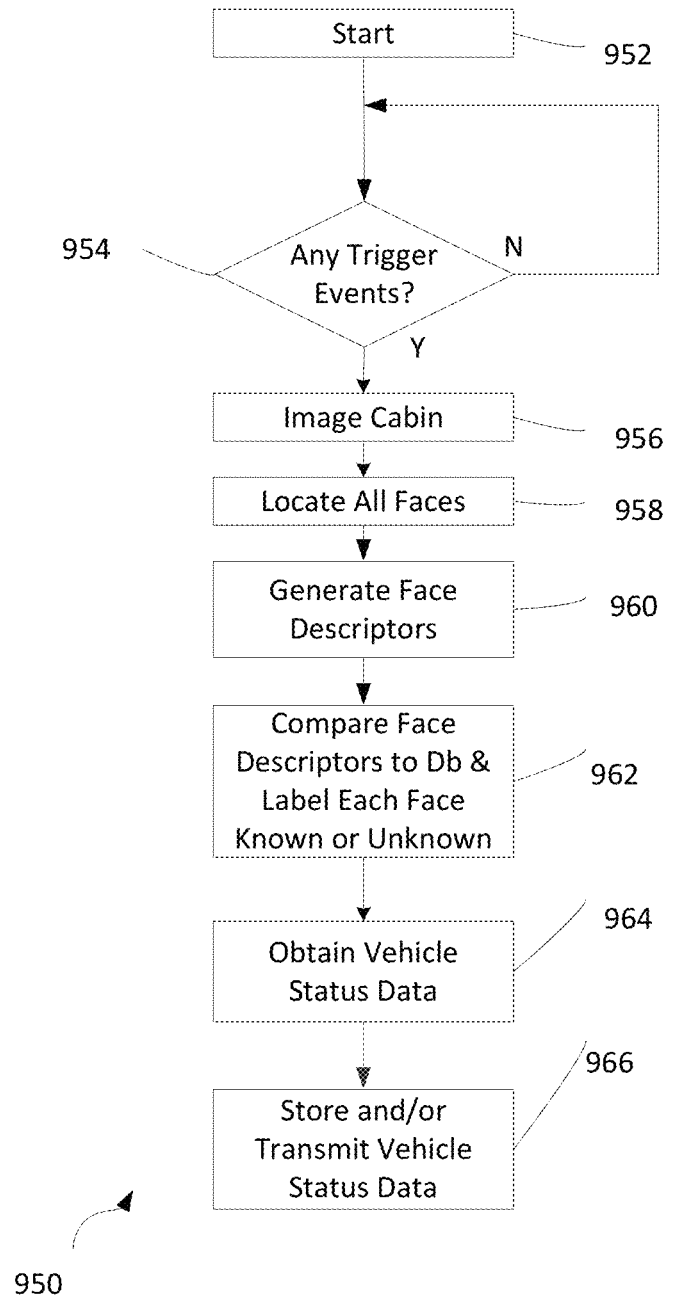
FIG. 9a is a flow diagram showing a further method of operating a driver behavior monitoring system having a driver facing camera for implementing a passenger detecting, counting, monitoring, and reporting strategy in accordance with an example embodiment.

FIG. 9a shows a further method 950 for detecting if any unauthorized passengers are present in the vehicle, how many passengers are present in the vehicle, and the identities of any detected passengers present in the vehicle. In the embodiment, the method 950 includes a series of steps that determine when passenger detection is performed, and what is detected and sent. Passenger visibility may be typically associated with the use of the passenger door opening and closing. In the example, passenger detection is performed only in response to selectable triggering events and is otherwise not performed. In the embodiment, a template image of the passenger door in opened, closed, opening, closing, and ajar conditions is used to detect the status of the passenger door as being opened, closed, uncertain, or the like. FIGS. 6a, 6b, and 7 for example show the driver door (similar appearance to the passenger door) beyond the driver, and it is the edges of this, at a fixed location, which is used by the system in accordance with the method 950 to determine whether it is open or closed.

The method 950 is initiated at step 952 by the system of an example the embodiment wherein a number of circumstances or trigger events are determined at step 954 for moving forward with the method 950 for determining whether any passengers are in the vehicle. If none of the triggering events are detected at step 954, the passenger detection module is not executed. However, the occurrence of any one or more of the trigger events being detected at step 754 will lead to the passenger detection module execution. In the example embodiment, the trigger events may include any one or more of the door being just (recently) opened, and the vehicle has recently stopped; the door being just (recently) closed (at which point an image is stored) and the vehicle begins moving thereafter; when the vehicle has just started moving forward; when a predetermined time for execution arrives, such as a monitoring interval; when a stop has occurred at an unusual location, such as on a highway, and the passenger door is open. Other trigger events may be used and are contemplated in the embodiment. A black box type data storage scheme may be used to retrieve suitable passenger images prior to the door being opened or just after it is closed. Suitability may be determined by the finding of a face oriented forward toward the windshield in the location where a passenger would appear.

When such circumstances occur, an image of the cabin is made in step 956 using the driver facing camera 345 of the embodiment described above. All faces in this image are located at step 958 by the logic of the system. Facial descriptors are generated in step 960 for these faces. The descriptors are compared in step 962 with one or more of an on-vehicle database 340 (FIG. 3) and/or off-vehicle database 450, 452, 454 (FIG. 4), and each face is labeled in accordance with the comparison(s) as "known" or "unknown" or, alternatively, labeled as being "allowed" or "not allowed." Any other suitable labels may be used as necessary or desired.

Vehicle status information is collected and stored at step 964 and a passenger detection status report is then in step 966 stored and/or sent to a central database. This report contains one or more of how many people are present in the vehicle, their identities (with the unknown John or Jane Doe state also possible), the cabin image, the vehicle location, the vehicle speed, the door status(plural possibly), the forward view, an audio recording if speech is detected from the microphone or lip motion signals.

A system is provided for monitoring a permitted occupant condition of an associated vehicle during operation of the associated vehicle by an associated driver. The system includes an imaging device disposed in the associated vehicle, a control device, facial detection logic, and control logic. The imaging device captures an image of the associated driver disposed in the associated vehicle. The imaging device also captures an image of an interior of the associated vehicle, and generating image data representative of the captured image of the associated driver disposed in the associated vehicle and of the interior of the associated vehicle. The control device includes a processor, an image data input operatively coupled with the processor, and a non-transient memory device operatively coupled with the processor. The image data input is configured to receive the image data from the imaging device. The facial detection logic is stored in the non-transient memory device, and is executable by the processor to process the image data to locate one or more face candidate areas of the image captured by the imaging device likely above a predetermined threshold stored in the non-transient memory device to be representative of a corresponding one or more human faces in the associated vehicle. The facial detection logic is further executable by the processor to generate a set of face descriptors for each of the one or more face candidate areas. The control logic stored is also stored in the non-transient memory device and is executable by the processor to determine, based on the set of face descriptors generated for each of the one or more face candidate areas, a vehicle occupant count as an operational value of an occupant quantity parameter of the monitored permitted occupant condition of the associated vehicle. The vehicle occupant count may be stored locally in the memory of the vehicle and/or transmitted to the central fleet management system.

Calibrated Seat Belt Usage Detection System

Too many drivers fail to regularly wear their seat belt thereby compromising their own personal safety. For commercial vehicle drivers, however, not wearing a seat belt may also violate fleet policy.

It is therefore desirable to detect whether or not a driver is properly wearing her/his seat belt during vehicle operation. In this regard, belt usage detection systems, methods, and apparatus are provided as described below.

Cameras are becoming somewhat ubiquitous in commercial vehicles for recording in a digital "loop" a video of the roadway ahead of the vehicles as they travel. The video is useful for accident recreation purposes and for other memorializing of the most recent activities of the vehicle and driver should any mechanical or other issues arise. Driver facing cameras have been used as well for imaging the driver from time to time as necessary such as, for example, whenever the vehicle is started so that the identity of the person in control of the vehicle can be determined at a later time.

Figure 10:
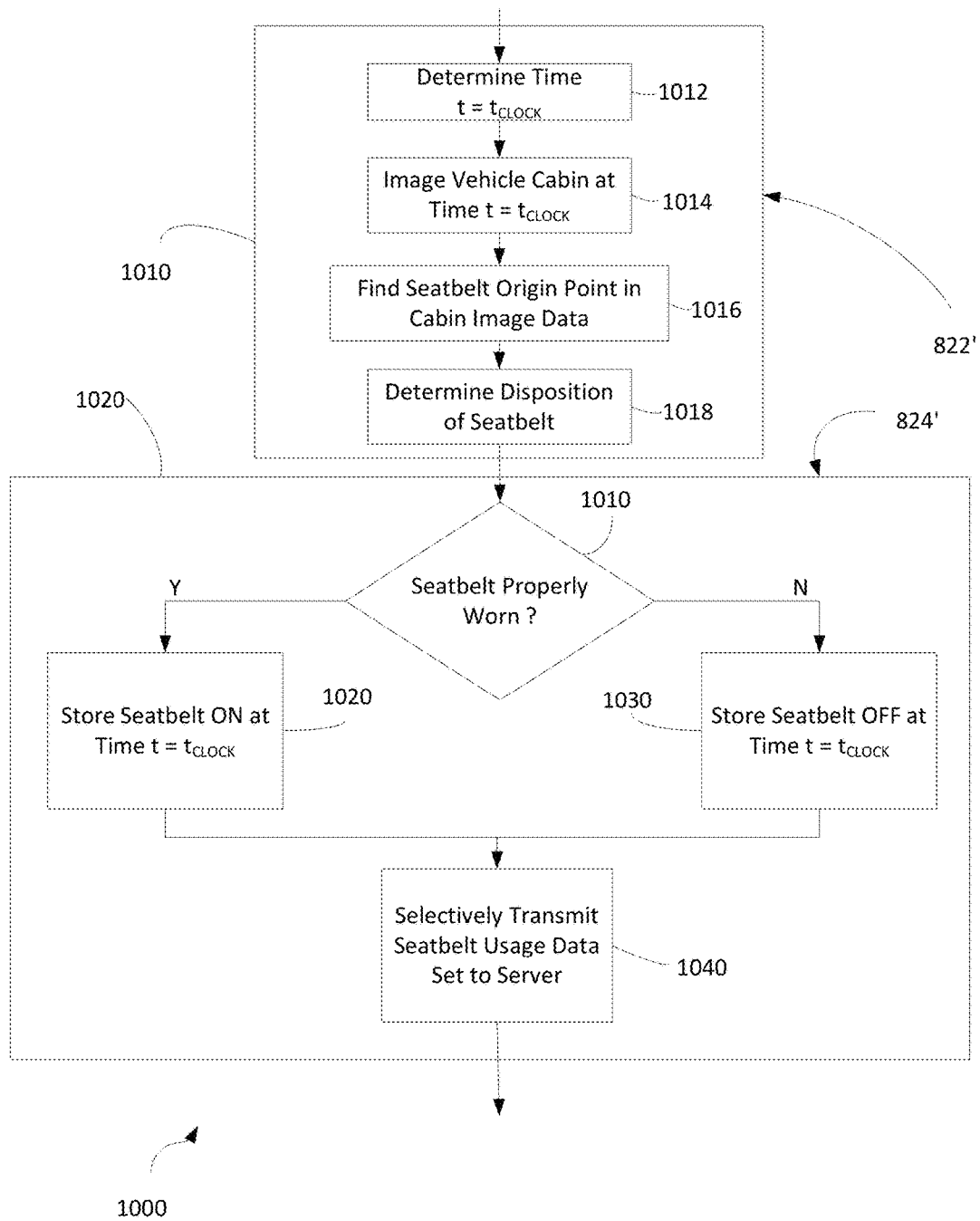
FIG. 10 is a flow diagram showing a method of operating a driver behavior monitoring system having a driver facing camera for implementing a seatbelt usage detection, monitoring, and reporting strategy in accordance with an example embodiment.
Figure 10A:
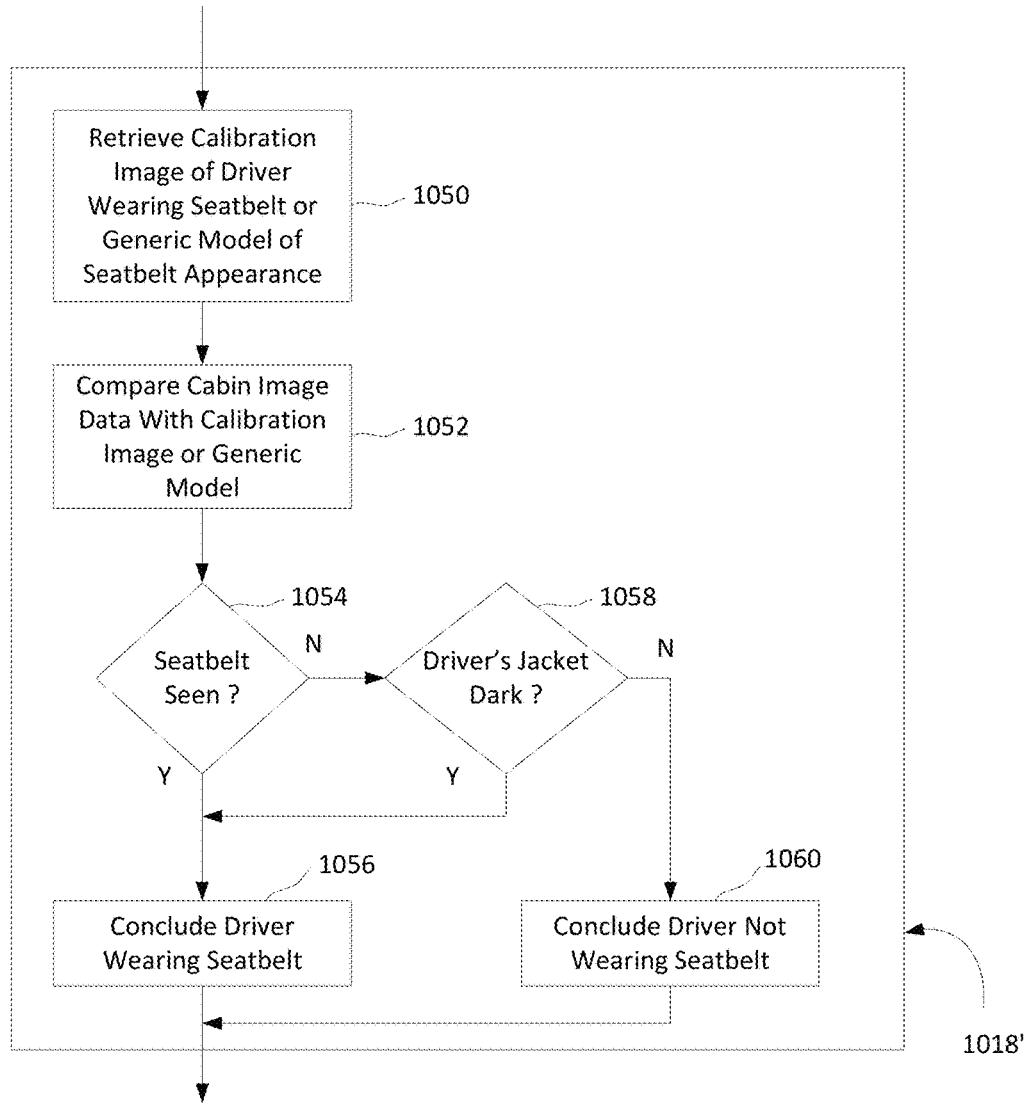
FIG. 10a is a flow diagram showing details of a portion of the method of operating a driver behavior monitoring system having a driver facing camera for implementing the seatbelt usage detection, monitoring, and reporting strategy of FIG. 10, in accordance with an example embodiment.
Figure 10B:
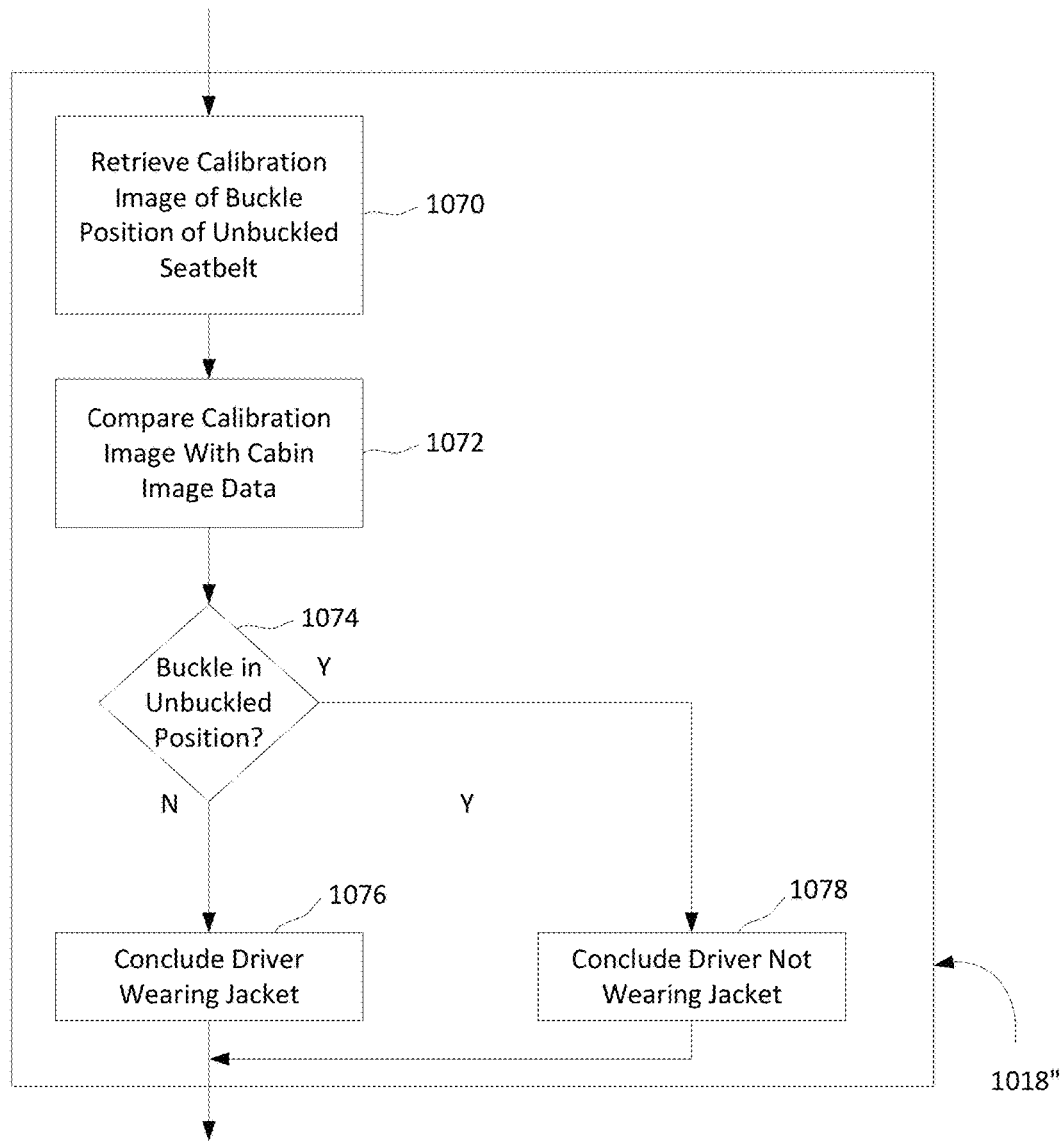
FIG. 10b is a flow diagram showing further details of a portion of the method of operating a driver behavior monitoring system having a driver facing camera for implementing the seatbelt usage detection, monitoring, and reporting strategy of FIG. 10, in accordance with an example embodiment.

In further embodiments herein, camera-based systems, method, and apparatus are provided for detecting whether a seat belt is being worn. An example embodiment of a method for detecting whether a seat belt is being worn is shown in FIGS. 10, 10a, and 10b. Expected features of a worn seat belt are sought in an image 700 (FIG. 7) taken by the driver facing camera 345. These features may include lines emanating from an origin point or region within a predetermined portion of the image 700. Alternatively or in addition, these features may include lines in the image within a range of angles. Alternatively or in addition, these features may including lines in the image with a range of colors between the lines, without discontinuity or if a discontinuity is present, where the line ends near the discontinuity point approximately parallel to and at each other.

FIG. 10 is a flow diagram showing a method of operating a driver behavior monitoring system having a driver facing camera for implementing a seatbelt usage detection, monitoring, and reporting strategy in accordance with an example embodiment. With reference now to that Figure, in the method 1000 of the embodiment, the cabin image data collection portion 822' includes a step 1012 determining a time of the image of the cabin, and a step 1014 collecting vehicle operational data such as, for example, vehicle speed data or the like. In step 1016 the logic of the system finds a seatbelt origin point in the cabin image data, and further, determines a disposition of the seatbelt in step 1018.

Next in the method 1000 shown in FIG. 10, the action taking portion 824' includes a step 1010 of determining whether the driver's seatbelt is properly worn. If the driver's seatbelt is properly worn, the method 1000 in step 1020 stores an "ON" identification or "ON" seatbelt status data. The "ON" identification or "ON" seatbelt status data may be stored together with the image of the cabin collected at step 1014 as maybe necessary and/or desired. On the other hand, if the driver's seatbelt is not properly worn, the method 1000 in step 1030 stores the an "OFF" identification or "OFF" seatbelt status data. Similar to the "ON" identification above, the "OFF" identification or "OFF" seatbelt status data may be stored together with the image of the cabin collected at step 1014 as may be necessary and/or desired.

Further in the method 1000 of the embodiment, one or more of the "ON" identification or "ON" seatbelt status data, the "OFF" identification or "OFF" seatbelt status data, and/or the image of the cabin collected at step 1014 is stored locally in the memory of the system at the vehicle or is transmitted in step 1040 to a central fleet management system.

FIG. 10a is a flow diagram showing details of a portion of the method of operating a driver behavior monitoring system having a driver facing camera for implementing the seatbelt usage detection, monitoring, and reporting strategy of FIG. 10, in accordance with an example embodiment. With reference now to that Figure, a calibration image 600 (FIG. 6a) of the driver 610 properly wearing his seatbelt is retrieved at step 1050 from a local memory of the system. The calibration image may be obtained in an initial step where the driver is requested to first not wear his seatbelt, and then in a second step, to wear his seatbelt. Alternatively, a generic model of a properly worn seatbelt 630 is retrieved at step 1050 from the local memory. The image of the vehicle cabin obtained at step 1014 (FIG. 10) is compared in step 1052 against the calibration image 600 and/or against the generic model of a properly worn seatbelt 630.

In step 1054 the system determines whether a seatbelt is "seen" or otherwise detected in the image of the vehicle cabin obtained at step 1014. If a seatbelt is seen at step 1054, the system concludes at step 1056 that the driver is indeed properly wearing his seatbelt. The method flow returns thereafter to the action taking portion 824' (FIG. 10) of the method of operating a driver behavior monitoring system in accordance with the embodiment. However, if a seatbelt is not seen at step 1054, a second examination at step 1058 is performed for the lightness or darkness of the driver's body covering (below the head). If this area is dark, it is possible that the driver is wearing dark clothing against which the seat belt may not be seen. If the driver is wearing dark clothing, then no judgement may be made regarding whether he is properly using the seat belt and the system concludes at step 1060 that the driver is properly wearing his seatbelt. If light clothing is detected, and no seat belt is seen the system concludes at step 1060 that the driver is not properly wearing his seatbelt. The method flow returns thereafter to the action taking portion 824' (FIG. 10) of the method of operating a driver behavior monitoring system in accordance with the embodiment.

FIG. 10b is a flow diagram showing further details of a portion of the method of operating a driver behavior monitoring system having a driver facing camera for implementing the seatbelt usage detection, monitoring, and reporting strategy of FIG. 10, in accordance with an example embodiment. With reference now to that Figure, a calibration image 602 (FIG. 6b) of the driver 610 improperly wearing his seatbelt is retrieved at step 1070 from a local memory of the system. Alternatively, a generic model of an improperly worn seatbelt 630' is retrieved at step 1070 from the local memory. The image of the vehicle cabin obtained at step 1014 (FIG. 10) is compared in step 1072 against the calibration image 602 and/or against the generic model of a properly worn seatbelt 630'.

In step 1074 the system determines whether a buckle 631' of an unbuckled seatbelt is "seen" or otherwise detected in the image of the vehicle cabin obtained at step 1014. If a buckle 631' of an unbuckled seatbelt is not seen at step 1074, the system concludes at step 1076 that the driver is wearing a jacket or the like. The method flow returns thereafter to the action taking portion 824' (FIG. 10) of the method of operating a driver behavior monitoring system in accordance with the embodiment. However, if the buckle 631' of an unbuckled seatbelt is "seen" or otherwise detected at step 1074 in the image of the vehicle cabin obtained at step 1014, the system concludes at step 1078 that the driver is not wearing a jacket. The method flow returns thereafter to action taking portion 824' (FIG. 10) of the method of operating a driver behavior monitoring system in accordance with the embodiment.

In an embodiment, a calibration image or model of seat belt appearance is taken or established. A matched model of the seat belt buckle may be applied to where the seat belt buckle may be visible. That is, a buckle 632 (FIG. 6b) should not be visible near the origin of the seat belt over the driver's shoulder. A warning or other action or function may be issued or otherwise started upon detection of the seat belt not being worn by the driver.

The driver facing camera 345 obtains an image 700 (FIG. 7) during operation of the vehicle and, in this way, the camera may see or know the origin point/region for the seat belt, which may be used to detect whether the seat belt is worn. FIG. 7 shows a user wearing her seat belt. These cameras see the origin point for the seat belt, and whether the seat belt is worn. The example embodiment advantageously uses knowledge of the origin point of the seatbelt, together with a calibration image 600 (FIG. 6*a*) of a driver 610 wearing the belt 630, or a generic model of seat belt appearance (angle, width, origin location, end location) in the image, to detect parallel lines within the appropriate width range, and originating and ending where expected. If no belt is seen, the method of the example embodiment is configured determine whether the driver's jacket is dark, thus rendering a dark belt invisible, for example. In that case, the method first tries increasing line detection sensitivity, failing which the method declares, by a benefit of the doubt analysis, that the driver is wearing a belt. If a lighter upper garment is worn and no dark (dark relative to the light upper garment) belt is detected, the method of the embodiment generates a signal that a lighter upper garment is worn and no belt is detected for storage in the local memory and/or for transmission to the central fleet management system.

It is to be understood that the seat belt is visible as a differently colored (contrasting) band-shaped area, with contrast to the objects next to or behind it. Where the seat belt is obscured by the person's scarf or face, a front edge line may still be visible and continues upward to reconnect to the 'two-sided' segment. Even when the seat belt is obscured by the full extent of the driver's clothing or the like, the ends would still be visible and would continue and 'point at' each other approximately. It is to further be noted that the seat belt is to the left of (in the image)/in front of the no person present location, were it buckled. The system thus has an expectation of what the image of the belt, properly worn, should looks like: (parallel/single/perhaps partially or fully obscured) lines, running in an approximate direction, between two known points (regions), and within a certain portion of the image. The system has the further expectation of what the visible portion of the belt looks like when worn behind the user. In this regard, the diagonal edges of the seat belt may advantageously be detected in accordance with the embodiments herein using, for example, Kirsch or other equivalent edge filters or the like.

In accordance with the embodiments herein, the system is not fooled or otherwise tricked into a determination of good seatbelt usage behavior by a driver wearing a 'seat belt t-shirt' (a shirt having a diagonal dark stripe graphic that appears to be a seat belt being worn). In this embodiment, the system inspects the cabin image for a set of nearly parallel edges emanating from the seat belt upper anchor point. In another embodiment, the system inspects the cabin image for lines continuing beyond the 'seat belt' (the false printed seat belt) that the driver appears to be wearing. Even if the user buckles the belt behind herself, a discontinuity is observed or otherwise detected by the system between the actual physical belt and the false belt pattern printed in the t-shirt. The system, by looking for this break, is able to detect that the user driver is not properly using the seatbelt.

Using knowledge of the origin point (or range), together with the calibration image 600 (FIG. 6*a*) of a driver 610 wearing the belt 630, or a generic model of seat belt appearance (angle, width, origin, end) in the image, also without a user present, the system is configured to detect parallel lines within the appropriate width range, and originating and ending where expected. If no belt is seen, the system checks if the driver's jacket is dark (thus rendering a dark belt invisible, for example), in which case it first tries increasing line detection sensitivity, failing which the system declares, by a benefit of the doubt analysis, that the driver is wearing a belt. If a lighter upper garment is worn and no belt is detected, the system signals this.

Alternatively, the system may detect the (generally shiny, and therefore probably light and contrasting) possibly visible buckle of the seat belt if the belt is not worn and not buckled. The camera is, either from known geometric installation values, or in a calibration step (simply signal where the belt origin point is), knows/is taught where the buckle would be visible. If the seat belt is perhaps not being worn, the system may switch to this second mode and detect the presence of the (unlatched) buckle 632 at the origin point such as shown, for example, in FIG. 6*b*. The origin point is furthermore typically fixed or conforms to a linear set of locations in the image. In an embodiment, a fixed patch is defined in the calibration image 602 (FIG. 6*b*) of the image where an unworn seat belt buckle 631' must appear, and it is there that the system may search for the buckle. If the seatbelt buckle is found in this fixed patch area, the system concludes that the driver is not wearing the seatbelt. Equivalently, for each driver, there is a fixed patch of the image corresponding to where a properly worn buckle 631 (FIG. 6*a*) appears. A matched template set of such properly buckled and unbuckled images appears may be stored and compared by the system with the actual image. Sufficient correspondence between an image in the stored sets and the DFC image patch corresponding to where the buckle may be leads the system of the embodiment to conclude that the driver is wearing, or not, her seatbelt.

A system is provided for monitoring seatbelt usage by a driver of a vehicle during operation of associated vehicle by the driver. The system includes an imaging device, a non-transient memory device storing safe model data comprising a recommended value range of a seatbelt use parameter of a monitored seatbelt worn by the associated driver condition of the associated vehicle, control logic stored in the non-transient memory device, and an output. The imaging device captures an image of an interior of the associated vehicle together with an image of the associated driver disposed in the associated vehicle, and generates image data representative of the captured images of the associated driver and the interior of the associated vehicle. The control logic is executable by the processor to process the image data to determine an operational value of the seatbelt use parameter of the monitored seatbelt worn condition of the associated vehicle, perform a comparison between the recommended value range of the seatbelt use parameter of the monitored seatbelt worn condition of the associated vehicle and the operational value of the seatbelt use parameter of the monitored seatbelt worn condition of the associated vehicle, and determine a state of vehicle operation compliance as a one of either a seatbelt non-compliance state or a seatbelt compliance state in accordance with the result of the comparison.

In an embodiment, the non-transient memory device stores a calibration image of a driver wearing a seatbelt having an origin point relative to the image of the interior of the associated vehicle as the safe model data comprising the recommended value range of the seatbelt use parameter of the monitored seatbelt worn condition of the associated vehicle. Also in the embodiment, the control logic stored in the non-transient memory device is executable by the processor to process the image data to determine, based on the calibration image having the origin point, a disposition of a seatbelt in the image data as the operational value of the seatbelt use parameter of the monitored seatbelt worn condition of the associated vehicle.

In a further embodiment, the non-transient memory device stores a generic model of a physical appearance of a buckled seatbelt as the safe model data comprising the recommended value range of the seatbelt use parameter of the monitored seatbelt worn condition of the associated vehicle. Also in the embodiment, the control logic stored in the non-transient memory device is executable by the processor to process the image data to determine, based on the generic model of the physical appearance of a buckled seatbelt, a disposition of a seatbelt in the image data as the operational value of the seatbelt use parameter of the monitored seatbelt worn condition of the associated vehicle.

The system of the example embodiment distinguishes between the type of non-usage of the seat belt. These types may include, for example, buckled behind the driver (or passenger), wearing an 'I am wearing a seat belt' upper outer garment, or simply not wearing the belt at all. Data relating to the type of non-wearing is stored locally and/or transmitted to the central fleet management server, along with a photograph of the non-wearing person or persons in the vehicle.

Driver's Hands on the Steering Wheel Detection

Too many vehicle operators fail to regularly properly place their hands on the steering wheel while driving, thereby compromising their own personal safety and risking damage to the vehicle. For commercial vehicle drivers, however, improper, inconsistent, or lax steering wheel hand placement may also violate fleet policy.

It is therefore desirable to detect whether or not a driver has properly placed hands on the steering wheel during vehicle operation. In this regard, driver's hands on the steering wheel detection systems, methods, and apparatus are provided as described below.

Figure 11:
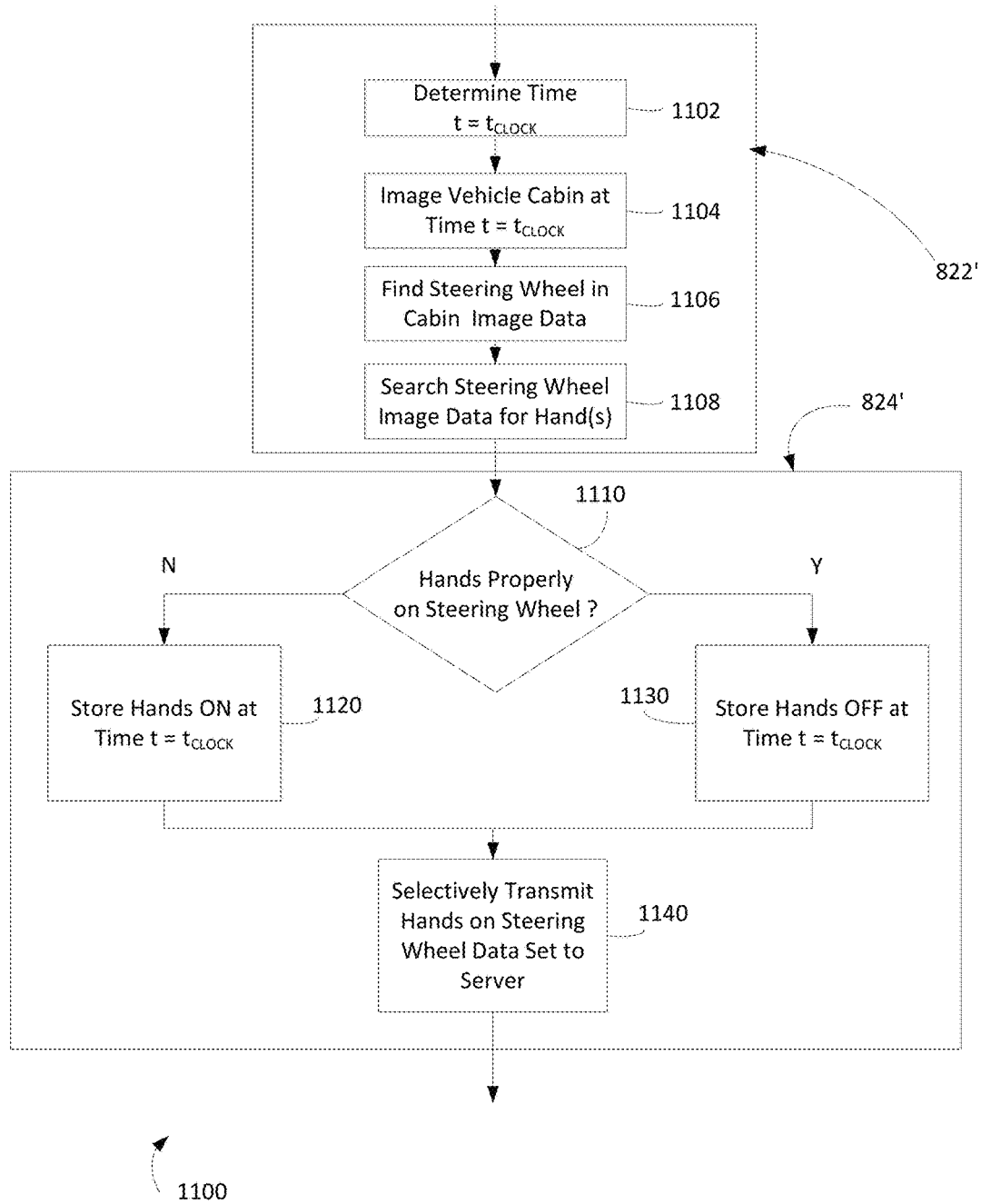
FIG. 11 is a flow diagram showing a method of operating a driver behavior monitoring system having a driver facing camera for implementing a hands on the steering wheel detection, monitoring, and reporting strategy in accordance with an example embodiment.

FIG. 11 is a flow diagram showing a method of operating a driver behavior monitoring system having a driver facing camera for implementing a hands on the steering wheel detection, monitoring, and reporting strategy in accordance with an example embodiment.

With reference now to that Figure, in the method 1100 of the embodiment, the cabin image data collection portion 822' includes a step 1102 determining a time of the image of the cabin, and a step 1104 collecting vehicle operational data such as, for example, vehicle speed data or the like. In step 1106 the logic of the system finds a steering wheel shape in the cabin image data, and further, searches the cabin image data for short (hand width dimension approximately) portions of the steering wheel that are not visible in step 1108.

Next in the method 1100 shown in FIG. 11, the action taking portion 824' includes a step 1110 of determining whether the driver's hands are properly on the wheel at the designated correct positions. If the driver's hands are properly on the wheel at the designated correct positions, the method 1100 in step 1120 stores a "Hands ON" identification or "Hands ON" steering wheel status data. The "ON" identification or "ON" steering wheel status data may be stored together with the image of the cabin collected at step 1104 as maybe necessary and/or desired. On the other hand, if the driver's hands are not properly on the wheel or are on the steering wheel but not on the wheel at the designated correct positions, the method 1100 in step 1130 stores the a "Hands OFF" identification or "OFF" steering wheel status data. Similar to the "Hands ON" identification above, the "Hands OFF" identification or the "Hands OFF" steering wheel status data may be stored together with the image of the cabin collected at step 1104 as may be necessary and/or desired.

Further in the method 1100 of the embodiment, one or more of the "Hands ON" identification or the "Hands ON" steering wheel status data, the "Hands OFF" identification or the "Hands OFF" steering wheel status data, and/or the image of the cabin collected at step 1104 is stored locally in the memory of the system at the vehicle or is transmitted in step 1140 to a central fleet management system.

Figure 12:
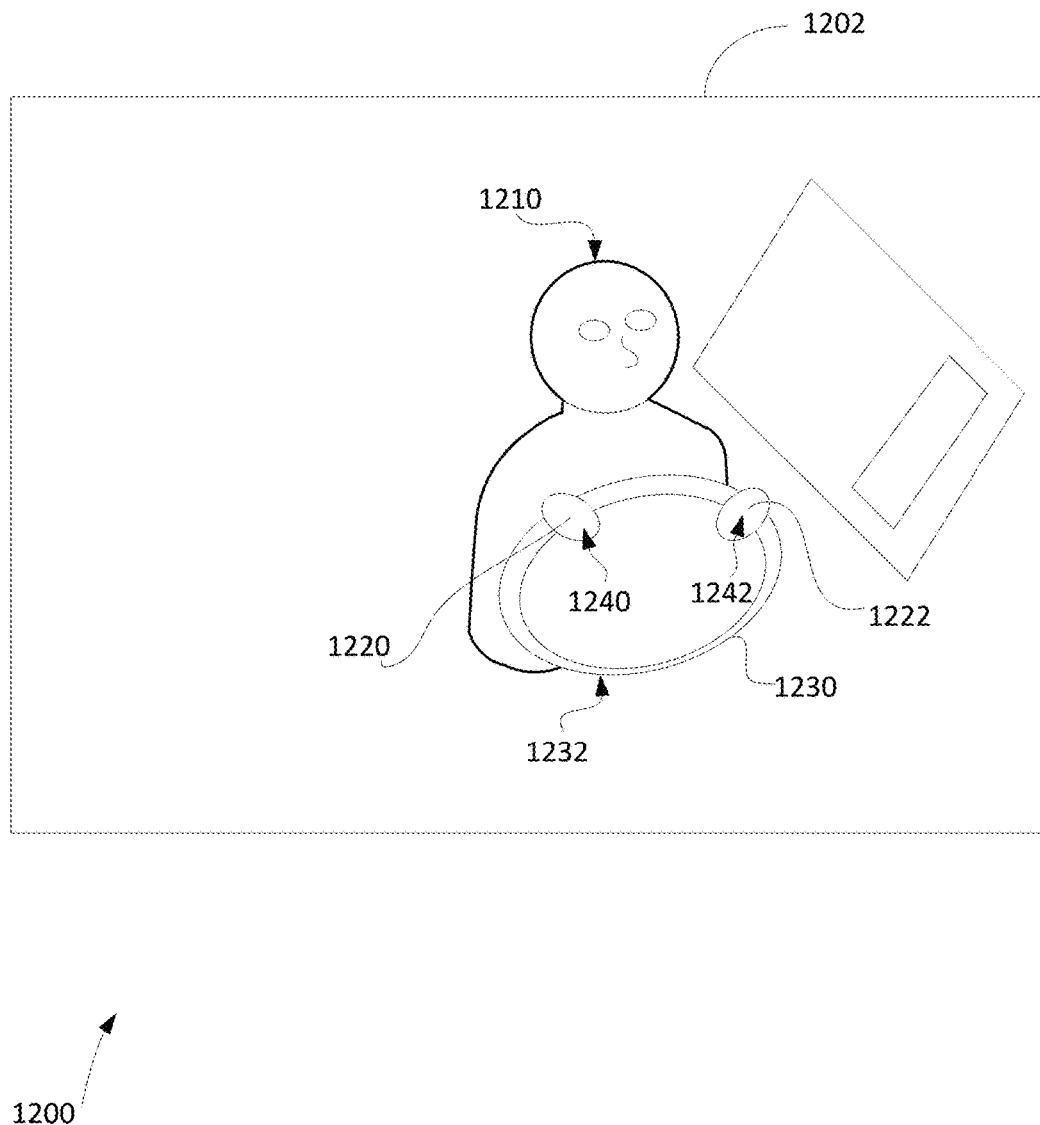
FIG. 12 is an example of an image generated by the driver facing camera of FIG. 5b and obtained by the driver behavior monitoring system during operation of the associated vehicle and showing a typical driver having his hands on the steering wheel.

FIG. 12 is an example of an image generated by the driver facing camera of FIG. 5b and obtained by the driver behavior monitoring system during operation of the associated vehicle and showing a typical driver having his hands on the steering wheel. Official recommendations are to have the driver's 1210 left hand 1222 at between the 9 and 10 o'clock positions on the steering wheel, and the right hand 1220 at between the 2 and 3 o'clock positions on the steering wheel, which is visible in the image 1202 of FIG. 12. The wide spacing is recommended because of the shape of the expanding airbag, should a collision occur. In the embodiment, the system seeks to find the driver's steering wheel hand positions in the image obtained by the driver facing camera 345. Not having one's hands at the recommended positions, or not having both one's hands on the wheel at all or not as frequently as may be required, is flagged by the system as a fleet policy infraction which is stored in the local memory and/or transmitted to the central fleet management system.

The embodiment takes advantage of the physical nature of steering wheels in commercial vehicles, which are nearly always circular. Circular shapes are easily detected in images, even when seen in a skewed view. The driver facing camera 345, typically sees the both the driver and steering wheel (if not the whole wheel, then a significant fraction thereof) which appears as an ellipse. A Hough Transform is used for ellipse detection (after lens distortion is accounted for) on an edge image from the driver facing camera 345. Only the edge points in the original image need to be undistorted, thus saving computation time. The Hough Transform returns where in the image the (elliptically shaped in the undistorted image) steering wheel is located. Those edge pixels are marked in the image that correspond to the wheel. Pixels in the image relating to unseen portions of the wheel may also be marked with indicia representative of information relating to where the wheel would be in the image, were the view of it not blocked. A model for the appearance of the whole steering wheel is thereby provided in the image, even though only a segment of the steering wheel is visible in the image. The driver's hands and arms can obscure portions of this image as may be seen in FIG. 12.

In an embodiment, the area of the image obtained by the driver facing camera 345 that is searched for these edge points may be limited or otherwise reduced, thereby saving processing time and improving accuracy. This image search area reduction may be performed based in substantial part on a knowledge of the optical and mechanical aspects of the camera and of its physical installation geometry, or in an initial calibration step, when the truck cabin's important features are located. For purposes of helping to expedite the search for items in the image, the driver facing camera 345 image edge search is constrained in the embodiment in terms of both the portion of the image to examined and what or which edge directions must be present or are otherwise expected to be there in the reduced portion of the image to be examined (e.g. the system does not expect a vertical edge at the top of the steering wheel 1230, this taken as seen from the driver's viewpoint; in the image the steering wheel edge is in fact approximately vertical).

The Hough Transform is preferably run on the undistorted edge image obtained from the driver facing camera 345 to detect ellipses. A high edge sensitivity may be used as necessary or desired, as the approximate location/appearance of the steering wheel are known, since there is only one ellipse, and it is within a limited size range. An alternative to the Hough Transform is to store template images of the steering wheel and compare these with what is seen by the DFC. The steering wheel portion of these images may be identified by the Hough Transform in an initial calibration step, and then stored, after which template matching is performed to locate the steering wheel in an image, without needing to perform the Hough Transform again The embodiment therefore uses knowledge of the possible steering wheel location(-s, if adjustable), along with Hough Transform ellipse detection, to localize the steering wheel 1230 in a driver facing camera image 1202 of the cabin of the vehicle. The contours of this detected ellipse 1232 are examined for missing sections 1240, 1242, indicating the locations where the driver's hands 1220, 1222 are, respectively, on the wheel. That is, the hands are not directly detected; rather, the unseen portions of the steering wheel are taken as the hand location(s).

It may be seen, for instance, in FIG. 12, that the right driver's hand 1220 interrupts the view of the steering wheel at 1240, but that on both sides thereof the steering wheel 1230 may be seen. The unseen edge pixels of the steering wheel 1230 are tagged, particularly on the right and top sides, and thus the system determines where the driver's right hand 1220 is. The left hand 1222 is where the top steering wheel section is no longer visible at 1242 looking to the left in the view shown. A knowledge of the steering wheel's color can also be used in accordance with the embodiment to help locate the steering wheel 1230 in the image 1202.

In addition, the system of the embodiment may execute logic to track the driver's hand movements relative to the steering wheel. For example, the system may look for active hand movement relative to the wheel (i.e. a changing hand position on the wheel), which may be used as a proxy for an attentive driver and recorded by the system as positive safety related events. Episodes of a non-changing hand position on the wheel may be used to alert the driver or may be recorded by the system as negative safety relevant events.

In an embodiment, one or more stored template images are used for determining where the steering wheel may be located, should it be adjustable, in the image. The one or more stored template images are compared with the image of the steering 1230 when obtained by the driver-facing camera. The best matching template image effectively locates the wheel in the image. Following this, the 'gap in the seen' steering wheel determination as described above is performed for locating the positions of the driver's hands 1220, 1222 on the wheel 1230 at the locations 1240, 1242 of the determined gaps in the steering wheel image 1232.

In addition to the above, the system of the embodiment may selectively perform a remapping of the elliptically appearing steering wheel in the image to a circle. This remapping corresponds to a re-projection of the wheel to a fully circular appearance. The sections of the steering wheel obscured 1240, 1242 by the driver's hands 1220, 1222 are also selectively transformed via this same remapping, and from these remapped hand positions the driver's angular hand spacing may be ascertained. Good driver behavior suggests an angular driver hand spacing of between approximately 180 degrees to approximately 120 degrees. The driver's hand position spacing on the wheel may be used to alert the driver or may be recorded by the system as positive or negative safety relevant events.

Fleet management or other policy violations such as: number of hands on the wheel, hand positions, percentage of time the driver holds the wheel, etc., may be detected, flagged, warned for, reminded about, and/or measured. Variation in hand position may be used as a proxy for driver fatigue.

II. Using Driver Facing Camera to Indirectly Monitor and Report Driver Behavior

Driver behavior may be directly monitored, in accordance with embodiments described herein, by using an imaging device trained on the driver while the vehicle is being operated. The monitored driver behavior is collected and stored locally in the vehicle and, in embodiments, may be reported to a central fleet management system.

Driver's Road Attention Detection

Too many drivers fail to pay proper attention to the road ahead. Drivers' eyes often wander from being directed towards the road owing to various tasks to be performed while driving such as, for example, checking gauges on the instrument panel, checking for other traffic using side view mirrors of the vehicle, operating radios or other gadgets on or in the vehicle cabin, and the like. This implies that the driver's eyes and therefore her attention aren't always where they should be; namely on the road, which has the tendency of adversely affecting the safe operation of the vehicle, particularly when drivers take their eyes off the road for prolonged or extended period of time, or when attention is frequently directed away from the road over time.

It is therefore desirable to detect whether or not a driver is paying proper attention to the road ahead while operating the vehicle. In this regard, driver road attention detection systems, methods, and apparatus are provided as described below.

In accordance with an embodiment, overall, the driver facing camera 345 of the driver behavior monitoring system is used to detect the direction the driver's head is facing, and the system relates this detected direction and the location of the driver-facing camera relative to the vehicle cabin structure to determine whether the driver is oriented such that the road can be properly seen. The relative position between the driver-facing camera and the vehicle cabin structure may be based on one or more calibration images as necessary and/or desired. The systems, methods, and apparatus of the embodiment are operable to transmit a signal to an associated central fleet management system when the driver is not oriented such that the road can be properly seen. Alternatively and/or in addition, the systems, methods, and apparatus of the embodiment are operable to store data representative of driver inattention into a local memory device when the driver is not oriented such that the road can be properly seen. The locally stored driver inattention data may be downloaded when the vehicle is taken off-line from the road, when the vehicle is being serviced, when the driver requests a download, or the like.

The systems, methods, and apparatus of the embodiments monitor the driver's road attention in accordance with a combination of a location of the driver's head and a facial normal vector of the driver's head. The location of the driver's head relative to vehicle cabin structure including for example the front windshield, and the facial normal vector of the driver's head are determined by the systems, methods, and apparatus of the embodiments. This is beneficial, for example, when drivers of different heights operating the same vehicle at different times is considered. For example, a short driver will need to look up more than a tall driver in order to properly see the road ahead.

In the example embodiment, a driver-facing camera 345 mounted on the windshield of a vehicle views the driver 520 (FIG. 5a) in the passenger cabin 530. The image taken by the camera 345 is analyzed to find the driver's head and which way she is facing which is expressed in the example embodiment as a facial normal vector 522. Standard methods of locating faces may be used for initial localization of the driver's head, after which a shape regression is performed by the driver behavior monitoring system to determine where the facial landmarks (e.g. nose, corners of the mouth, tragus points) are. Using these landmarks, a generic head model is fitted, from which the facial normal vector 522 is derived, the details of which will be explained below.

A monocular camera cannot, however, determine how far away an object is without further information. This being the case, the driver behavior monitoring system may determine the driver's head location in several ways, three of which will be described below.

In accordance with a first method, known landmarks on the driver's seat are used to measure the distance to and/or the height of the driver's seat, and from these distance and/or height measurements an approximate driver head location may be inferred. The known landmarks on the driver's seat 620 (FIG. 6*a*) are preferably contained in the calibration image 600 (FIG. 6*a*).

In accordance with a second method, one or more calibration photos are used to determine the driver's head location. For example, the driver may be asked to lean directly back against the fully backed seat, so producing a known position, in the reference snapshot image 600 (FIG. 6*a*).

In accordance with a third method, assuming the driver 610 is sitting centered on the seat 620 in the reference snapshot image 600 (FIG. 6*a*), his nose 611 will be in the vertical half-seat plane 621, making the driver's head 520 easy to locate in the image. Typical truck seats move up and down, front and back, and their backrest is tiltable. The sides of the seat therefore move within a fixed plane to some approximation. A typical truck calibration image 600 is shown in FIG. 6*a*, and a typical truck operational image 700 is shown in FIG. 7.

The driver-facing camera 345 may locate a point 622 of the (typically visible) seat side in the image such as for example at the upper left corner of the seatback over the driver's right shoulder or elsewhere such as the back of the lower seat cushion just under a likely position of a driver's ID badge on his right hip (not shown), and thereby the driver behavior monitoring system of the embodiment establishes a ray in 3-D space, emanating from the camera and going through this seat point 622. In a monocular situation this fact would establish only the ray along which the seat point lies, and not exactly how far away this point 622 is from the camera 345.

In accordance with the embodiments herein, however, the ray intersects a known plane, and thereby defines a single point 622 in the 3-D space of the passenger cabin 530. Following the installation and a calibration of the camera, and if the seat location is known, the driver behavior monitoring system of the example embodiment uses the full 3-D coordinates of the calibration seat point. With this, the driver behavior monitoring system of the embodiment can better establish data used for determining where in the 3-D space of the passenger cabin 530 the driver's head is located.

A similar principle may be applied in accordance with a driver behavior monitoring system of a further embodiment to find the driver's nose tip 611. In this embodiment, the driver behavior monitoring system presumes that the position of the driver's nose in the image is likely near the vertical plane 621 cutting the driver's seat in half. This preamble results again in a line intersecting a plane and the 3-D facial normal vector origin is therefore determinable in three dimensions.

For the subject driver facing camera, the system fits a head model to the driver's appearance, thereby obtaining a facial normal vector 522. The head model, which is generic, is rotated and scaled in 3-D space until it fits the undistorted image of the driver's head as well as possible. The system thereby has the three angles characterizing the head pose, to within generic head model limits, and a scale factor. The driver head pose angles include, for example, a driver's head pitch angle (driver looking down or up), a driver's head yaw angle (driver looking left or right), and a driver's head roll angle (driver tilting his/her head to the left or right).

The system does not, however, have or otherwise know the absolute distance 1640 (FIG. 16) of the driver from the camera, that is, the system does not have or otherwise know 3-D driver head location information (just the angles). For this, the typical pupillary distance limits can give the system a bound, wherein women have a mean pupillary distance of 61.7 mm, and men have a mean pupillary distance of 64.0, both with a standard deviation of ~3.5 mm. This renders a head distance to within ~+/−10% for ~95% of the human population in general. That is, in the embodiment, the system first preferentially looks for driver gender, then takes the corresponding inter-pupillary distance 1630 eye center 1620 to eye center 1622 (FIG. 16) and relates the image head eye spacing to distance from the camera. Since the system has the head pose angles, the system can get the inter-pupillary distance in pixels as if the driver were directly facing the camera. Then, using pixel size, the system determines the interpupillary distance in meters, apply the lens focal length. Via similar triangles, the system calculates the head to camera distance as:

Head to camera distance=(lens focal length*gender interpupillary distance)/(facing the camera in the image interpupillary distance).

For instance, if there are 20 pixels separating the pupils (or eye centers 1620, 1622, taken as proxies for the pupils), and pixels are 4 microns in size, then there are 80 micrometers between the pupils. If, furthermore, the lens focal length is 2 millimeters, and driver gender is determined as male, then the camera to driver head distance is (2 mm*64 mm/80 micrometers) or 1.6 meters. Given the variability in eye spacing, one may allow for this uncertainty in the final head location, and 'soften' the criteria for out of position warnings.

With the distance, the system is able to locate the driver's head in 3-D space, and then use the facial normal vector direction to relate to the vehicle cabin, mirrors, gauges, road, etc. As the facial normal vector 522 typically originates at the nose tip 611, the camera to head distance is known, and the angle to the head via the nose tip location in the image is also known, the system of the example embodiment calculates the facial normal vector location in space, and verifies that the facial normal vector "points" or is otherwise directed at or to the desired regions around the driver, such as mirrors, road, next lane when passing, etc.

Overall, the driver behavior monitoring system of the embodiment monitors the facial normal vector over time and compares the monitored facial normal vector with predetermined statistical properly-directed facial normal vectors. The facial normal vector information is stored local in the memory of the system together with the results of the comparison over time. These data and result may be transmitted to the central fleet management system as may be necessary or desired.

Figure 13:
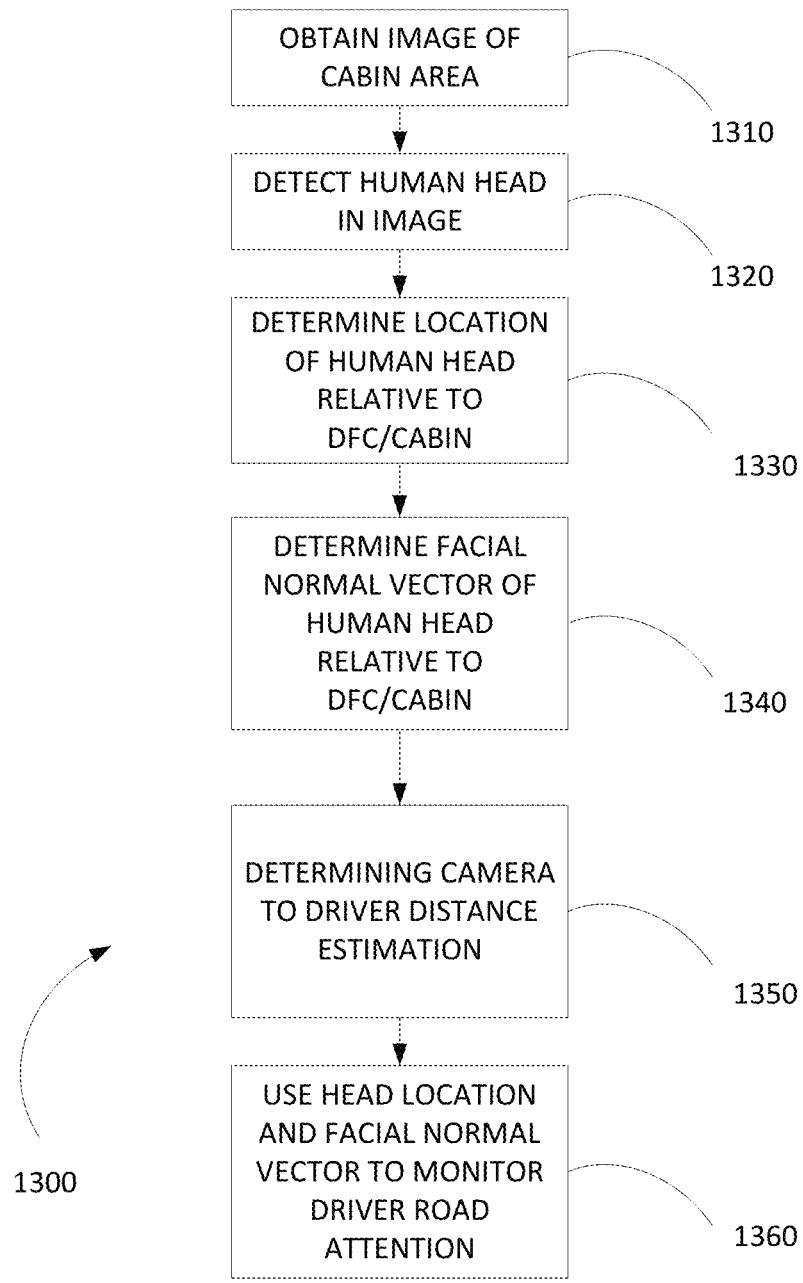
FIG. 13 is a flow diagram showing a method of operating a driver behavior monitoring system having a driver facing camera for implementing a driver road attention detection, monitoring, and reporting strategy in accordance with an example embodiment.

FIG. 13 is a flow diagram showing a method 1300 of monitoring the driver's road attention in accordance with a combination of a location of the driver's head and a facial normal vector of the driver's head. An image of the cabin area of the vehicle is obtained at step 1310. A human head is detected in the image at step 1320. In step 1330, the location of the human head relative to the driver-facing camera 345 and/or relative to the various components of the cabin of the vehicle is determined. The facial normal vector of the detected human head is determined at step 1340. An estimated distance between the camera and the driver's head is determined at step 1350. Then, at step 1360, the driver's road attention is monitored over time using the determined facial normal vector of the head in combination with the determined head location, wherein the determined head location is used as the base point of the facial normal vector for the monitoring.

In a further embodiment, an auto-calibration function may be realized by collecting statistics of where the driver is looking when at highway speeds over time. It may be assumed that the driver is facing predominantly forward when the vehicle is traveling over some speed, that is, the driver is very likely paying attention when moving quickly, and the most frequent or average normal vector direction will correspond to the road straight ahead. Therefore, the system of the embodiment collects normal vector statistics by either a histogram method, a recursive average the pose angle method or a combination of the histogram and the recursive average the pose angle methods. In the histogram method, a histogram is created and populated for each of the set of driver's "head pose" normal vector angles describing the orientation of the driver's head, that is, a pitch histogram (driver looking down or up), a yaw histogram (driver looking left or right), and a roll histogram (driver tilting his/her head to the left or right). The normal vector statistics are collected for a predetermined time, such as, for example, 1 minute, after which the system takes the fullest histogram bin as corresponding to a straight ahead driver's head pose direction. Alternatively, the system recursively averages the head pose angles, and determines the average value as representing straight ahead driver's head pose direction, again letting the averages run for long enough and only when the vehicle is travelling fast enough.

Detection of Impeded Driver-Facing Camera

Knowing that the driver-facing camera 345 in accordance with the embodiments herein vigilantly watches the drivers at all times during operation of the vehicle, some operators may choose to attempt to defeat the camera for various reasons including for example, to hide fleet policy violations or mistakes, or the like. However, the driver facing camera functionalities depend in large part on a clear view of the driver. Detecting a clear view of the driver is therefore highly desirable for the proper operation of the detection and reporting embodiments herein.

It is therefore desirable to detect whether or not a driver is attempting to defeat the driver facing camera. In this regard, impeded driver-facing camera detection systems, methods, and apparatus are provided as described below. One benefit of these embodiments is that proper driver facing camera operation is ensured, thereby fully supporting the many functionalities of the several example embodiments described herein.

In accordance with an embodiment, overall, the driver facing camera 345 of the driver behavior monitoring system is used to detect the driver's head in the cabin of the vehicle during operation thereof. In the embodiment, the driver facing camera is supplemented with face detection logic for determining the face of the vehicle operator. The logic of the example embodiment is executed to monitor for the continued availability of a visible face, of approximately unvarying appearance, when the vehicle is in motion. The logic of the example embodiment is executed to generate a signal of a detected loss of operator verification if no face is visible and/or determinable when the vehicle is moving.

In a further embodiment, the logic of the example embodiment includes driver face finding functionality that executes to use foreground-background methods of object identification. The relatively static nature of the driver-facing camera 345 being fixedly mounted to the vehicle headliner support member 512 (FIG. 5a) enables the foreground-background methods of object identification for monitoring for the continued availability of a visible driver's face, of approximately unvarying appearance, when the vehicle is in motion. Initially, background pixels; that is, those pixels deemed to be unchanging due to only small changes in their value, persistently cover a sufficiently high percentage of the region, or even image, where are driver's face is not expected to be seen. However, when the background pixels begin to persistently cover a sufficiently high percentage of the region, or even the image, where are driver's face may be expected to be seen, the logic of the system then determines that the image does not have a live image of the driver and that the camera may therefore be deemed to be impeded or otherwise blocked. If no face is visible when the vehicle is moving, a loss of operator verification signal is generated and selectively transmitted to the central fleet management system or stored locally in the system memory.

In accordance with an embodiment, driver face detection logic stored in a non-transient memory device of the subject driver behavior monitoring and reporting system is executable by a processor of the system to process driver's head location data and a facial normal vector determined as described above to selectively determine, from the image data, a face of the driver of the associated vehicle, and generate a one of: driver's facial characteristic data representative of the selectively determined face of the associated driver, or impeded image data representative of an inability of the driver face detection location logic to selectively determine the face of the driver of the associated vehicle from the image data.

The subject driver behavior monitoring and reporting system of the embodiment includes an input operatively coupled with the processor, the input selectively receiving from the associated vehicle a vehicle moving signal and/or a human control active signal representative of motion of the associated vehicle.

The control logic is executable by the processor to selectively generate, responsive to the input receiving the vehicle moving signal and to the impeded image data being generated, a obstructed view data representative of an obstruction between the imaging device and the associated driver disposed in the associated vehicle.

The subject driver behavior monitoring and reporting system of the embodiment further includes driver face detection logic stored in the non-transient memory device. The driver face detection logic is executable by the processor to process the image data together with the vehicle geometry data and the imaging device position data to determine one or more foreground objects in the image data and one or more background objects in the image data, the determined one or more foreground objects in the image data being disposed in the associated vehicle between the imaging device and the one or more background objects in the image data.

The driver face detection logic is further executable by the processor to process the a portion of the image data corresponding to the determined one or more foreground objects in the image data to selectively determine, from the image data, a face of the driver of the associated vehicle, and generate a one of: driver's facial characteristic data representative of the selectively determined face of the associated driver, or impeded image data representative of an inability of the driver face detection location logic to selectively determine the face of the driver of the associated vehicle from the image data.

The subject driver behavior monitoring and reporting system of the embodiment further includes an input operatively coupled with the processor, the input selectively receiving from the associated vehicle a vehicle moving signal representative of motion of the associated vehicle. In the embodiment, the control logic is executable by the processor to selectively generate, responsive to the input receiving the vehicle moving signal and to the impeded image data being generated, a obstructed view data representative of an obstruction between the imaging device and the associated driver disposed in the associated vehicle.

Figure 14:
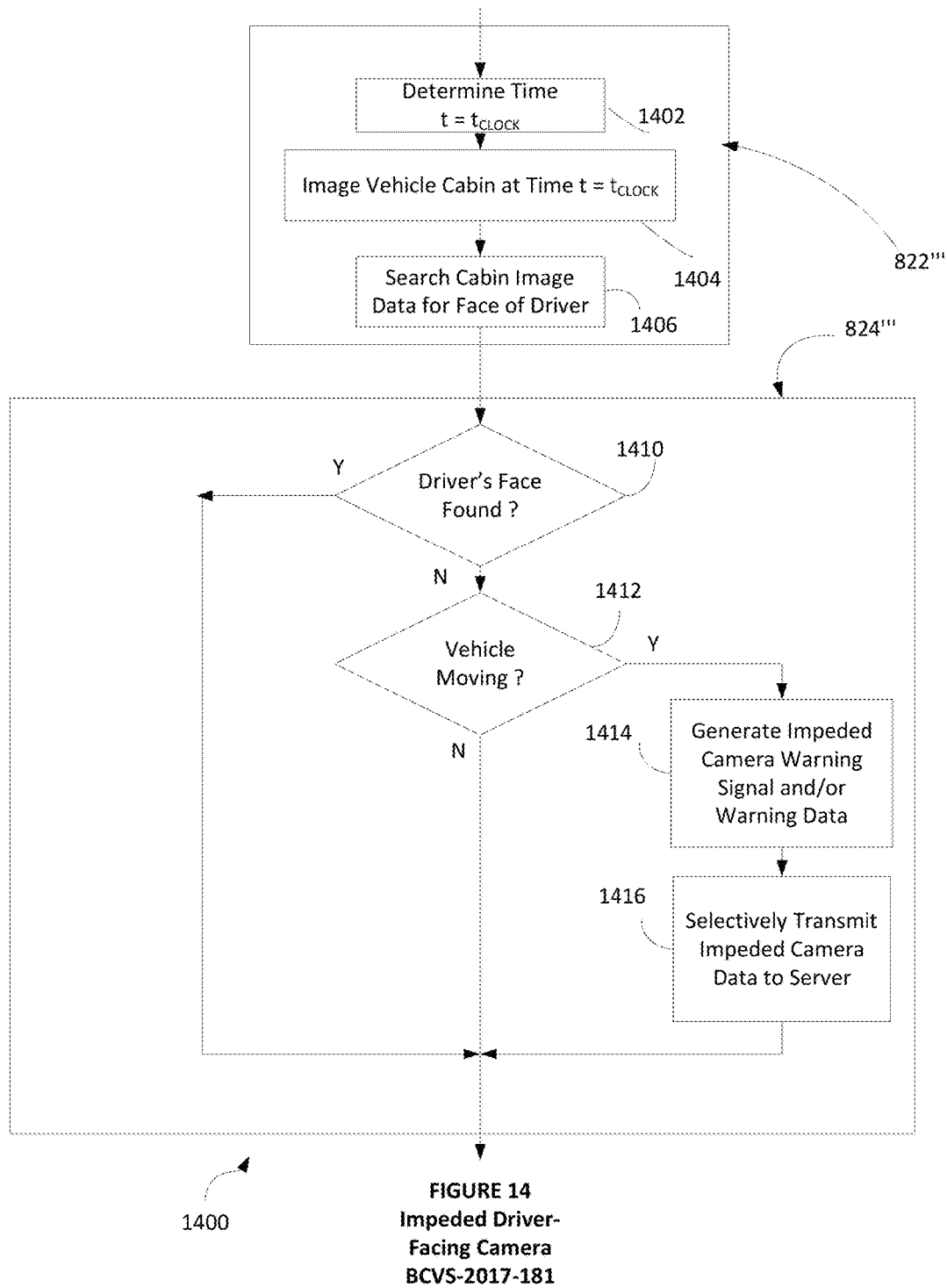
FIG. 14 is a flow diagram showing a method of operating a driver behavior monitoring system having a driver facing camera for implementing an impeded view detection, monitoring, and reporting strategy in accordance with an example embodiment.

FIG. 14 is a flow diagram showing a method 1400 of monitoring the presence of a driver's face in accordance with an example embodiment. The time is determined at step 1402 and an image of the vehicle cabin is obtained in step 1404. The time may be associated with the cabin image data as necessary or desired. The cabin image data is searched at step 1406 to find a human face, in the approximate location where the driver's face may be expected to be.

A determination is made at step 1410 whether a driver's face is found in the cabin image in step 1406. If no face is found a further determination is made at step 1412 whether the vehicle is moving. If no face is found and the vehicle is moving, a warning signal is generated at step 1414, and the warning signal is selectively transmitted at step 1416 to the central fleet management system. Alternatively, the warning signal may be stored locally in the memory of the driver behavior monitoring system of the embodiment.

Driver's Head Out of Position

Many vehicle operators reach for items while driving such as, for example, control knobs on the dashboard, cups stowed in nearby cup holders, maps or other items stowed in a center console or door pocket next to the driver's seat, or the like. This is of course normal behavior. However, it has been found that reaching to gain access to faraway objects while driving increases the chances of an accident by a factor of about eight (8).

It is therefore desirable to measure and warn for an out of normal position head, as this correlates to excessively reaching. The driver's head position is used in the example embodiment as a proxy for the driver's reach and, in particular, the driver's head position is used in the example embodiment as a proxy for the driver's excessive reaching thereby generating a signal representative of this monitored driver behavior.

The example embodiment to be described herein provides a verification of the driver not excessively reaching for items beyond his considered to be safe grasp space, preferably an extent of a reach maneuver capable of being performed by the driver without excessive body movement. Understanding of typical driver head position and warning when the driver over-reaches in accordance with the example embodiments is beneficial to help prevent accidents caused by driver inattention.

The driver behavior monitoring system of the example embodiment uses the driver facing camera 345 to locate and measure the driver's head position. Logic executing in the driver behavior monitoring system uses recursive measurement equations to determine the mean and variance of the set of determined driver's head positions. The logic executing generates a warning or notice signal when a driver's head position deviates from the mean position by more than a predetermined number of standard deviations in any axis (x-y- or z-) and when this deviation occurs for a predetermined minimum time period. The predetermined number of standard deviations and the predetermined minimum time to be out of position are parameters that are settable or otherwise selectable by the operator or fleet system manager. Typical values of these settable parameters may be two (2) standard deviations, essentially covering about 95% of a normally distributed variable, and for approximately 1-2 seconds. The driver's head out of position events are determined and recorded into the local memory device of the driver behavior monitoring system of the example embodiment. The driver's out of position behavior is recorded by the camera 345 and may be stored together with other data relating to the operation of the vehicle at the time the driver's head was out of position such as, for example, vehicle speed data or the like. An out of head position indication combined with a high vehicle speed indication from the vehicle speed sensors may be used by the system to grade or otherwise score the head out of position occurrence more negatively than for example an out of head position indication combined with a very low vehicle speed indication from the vehicle speed sensors. Stopping the vehicle to reach for items beyond the driver's considered to be safe grasp space is graded or otherwise scored by the driver behavior monitoring system of example embodiment to be good driver behavior. Conversely, continued operation of the vehicle at highway speeds for example while reaching for items beyond the driver's considered to be safe grasp space is graded or otherwise scored by the driver behavior monitoring system of example embodiment to be bad driver behavior. Other one or more vehicle conditions may be monitored and combined with the driver's head position used in the example embodiments as a proxy for the driver's reach for determining a level of driver behavior on a good to bad scale.

Figure 15:
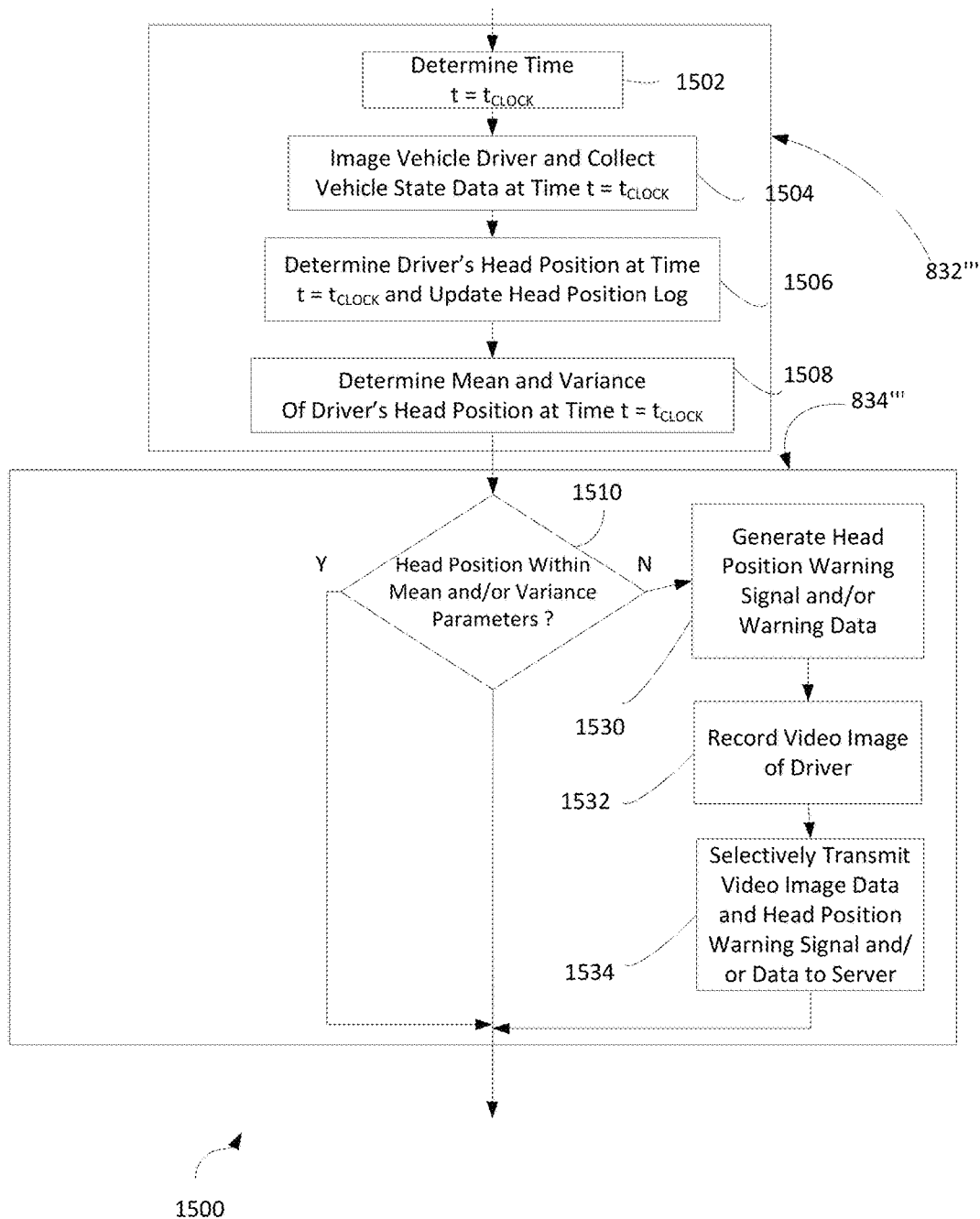
FIG. 15 is a flow diagram showing a method of operating a driver behavior monitoring system having a driver facing camera for implementing a driver's head is out of position detection, monitoring, and reporting strategy in accordance with an example embodiment.

FIG. 15 is a flow diagram showing a method 1500 of monitoring the position of the driver's head used as a proxy for the driver's reach and, in particular, used in as a proxy for the driver's excessive reaching, in accordance with an example embodiment. The time is determined at step 1502 and an image of the vehicle cabin is obtained in step 1504. The time may be associated with the cabin image data as necessary or desired. The cabin image data is searched at step 1506 to find a human head, preferably the driver's head. The location of the driver's head is stored into a local memory in order that, in step 1508, the mean and variance of the driver's head position may be determined over a predetermined time interval.

A determination is made at step 1510 whether the driver's head position is outside of the mean and/or variance values determined in step 1508. In an embodiment, the determination made at step 1510 of whether the driver's head position is outside of the mean and/or variance values determined in step 1508 includes determining whether the driver's head position is outside of the mean and/or variance values for a predetermined time period, which may be selectable by the operator or fleet manager. A head position warning signal is generated at step 1530 indicating that the driver's head position is outside of the mean and/or variance values for a predetermined time period. A video image of the driver is recorded at step 1532, and the head position warning signal and the video image of the driver are selectively transmitted to the central fleet manager in step 1534.

Alternatively, the head position warning signal and the video image of the driver may be stored locally in the memory of the driver behavior monitoring system of the embodiment.

Figure 15A:
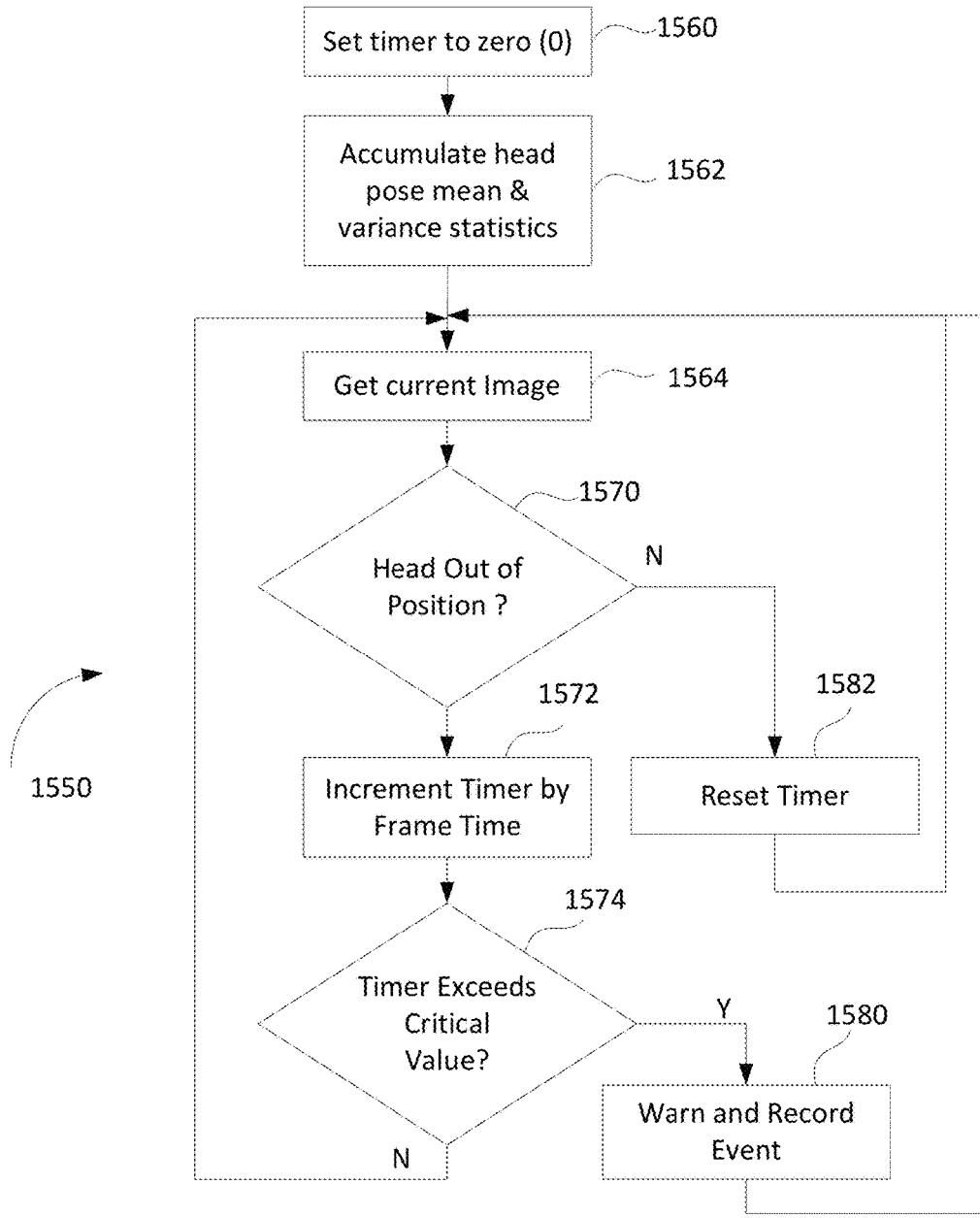
FIG. 15a is a flow diagram showing a further method of operating a driver behavior monitoring system having a driver facing camera for implementing a driver's head is out of position detection, monitoring, and reporting strategy in accordance with an example embodiment.

FIG. 15a is a flow diagram showing a method 1550 of determining whether the driver's head is out of position in accordance with an example embodiment, with a particular focus on collecting statistics of a "normal" driver's head position such as, for example while the vehicle is moving sufficiently fast enough and for a sufficiently long enough period, prior to assessing the driver's head out of position in accordance with the collected statistics. A timer is initialized in step 1560, and the driver's head pose statistics are collected at step 1562. Preferably, the driver's head pose statistics are collected when the vehicle is moving quickly enough, and for long enough. The driver's head pose mean and variance values need in the example embodiment, some time to develop before they have any practical value such as, for example, on the scale of about one (1) minute at speed. Only after driver's head pose mean and variance values are collected and developed at step 1562 does the system of the embodiment know what is 'regular' driving for this driver, and only then does the system perform driver's head out of position testing. This test first consists of imaging the driver to obtain at step 1564 a current driver's image. A comparison is performed at step 1570 between the current measured head pose values (yaw, pitch, roll, location) and the mean values of these driver head pose angles including for example a driver's head pitch (driver looking down or up), a driver's head yaw (driver looking left or right), and a driver's head roll (driver tilting his/her head to the left or right) developed at step 1562. If any of these deviates by more than a selectable amount of standard deviations, preferably about two (2) standard deviations from the corresponding mean, the system deems the driver's head to be out of position. A timer is started in step 1572 when the head is out of position. Should the value of the timer exceed a threshold as determined at step 1574, a warning is issued at step 1580. When the head is not out of position, the timer is reset to zero at step 1582.

In accordance with the example embodiment, control logic of the driver behavior monitoring and reporting system is executable by a processor of the system to determine, over a predetermined detection time, a central value of a facial normal vector of the driver of a vehicle, and to determine, over the predetermined detection time, a dispersion of the central value of the facial normal vector. The mean of the head position value of the facial normal vector may be determined and a variance of the facial normal vector may be determined to render a standard deviation of the driver's head position as the square root of the variance.

A memory device of the stores, as the driver road attention parameter of the safe attention model data, a recommended value range of a driver head out of position parameter of the monitored driver attention condition as a selectable multiple of the determined standard deviation of the facial normal vector.

The control logic stored in the non-transient memory device is executable by the processor of the driver behavior monitoring and reporting system to process the facial normal vector to determine an operational value of the driver road attention parameter of the monitored driver attention condition of the associated vehicle, and to perform a comparison between the recommended value range of the driver head out of position parameter of the monitored driver attention condition of the associated vehicle and the determined operational value of the driver head out of position parameter of the monitored driver attention condition of the associated vehicle.

The control logic stored in the non-transient memory device is further executable by the processor of the driver behavior monitoring and reporting system to determine a driver inattention value as a driver inattention value.

The control logic may further determine the state of vehicle operation compliance in a binary sense as a one of a driver inattention state in accordance with a first result of the comparison between the recommended value range and the determined operational value of the driver head out of position parameter of the monitored driver attention condition of the associated vehicle, wherein the processor generates the driver inattention data in accordance with the first result, or a driver attention state in accordance with a second result of the comparison between the recommended value range and the determined operational value of the driver head out of position parameter of the monitored driver attention condition of the associated vehicle.

Driver's Head Pose Distribution Metric

One aspect of good driving behavior may be characterized as the driver being in their proper, individual, driving position, i.e. able to hold the steering wheel, able to see forward to the roadway, able to see the mirrors, positioned within reach of the pedals, and the like. Essentially, good body position within the vehicle will usually lead to an optimized driver performance. Deviations from these operational positions are associated with a greater risk of accidents, by up to a factor of about eight (8) as noted above. Another aspect of good driving behavior may be characterized as the driver actually looking where they should when they drive. For instance, mirrors shall be utilized when backing, so eyes off the forward road under these conditions is acceptable, and eyes on one of the vehicle mirrors is desired. Light traffic while moving forward might require the driver to scan the forward road often with periodic mirror scans, but with most attention being paid to the forward road. However, dense traffic situations probably require more scanning of the side mirrors than with little traffic. Lane changes are beneficially prefaced by looking at the lane into which one is going.

It is desired therefore to detect improper or deviant head direction behavior, particularly against the background of the current driving maneuver, and to use this as a monitored behavior event. The driver may be warned by the system when an improper or deviant behavior occurs. A signal may be generated when the improper or deviant behavior occurs and data representative of the signal may be stored locally in the vehicle mounted monitoring system or transmitted to the central fleet management system. Still images or video images of the cabin of the vehicle may be recorded when the improper or deviant behavior occurs and data representative of the cabin images taken during the improper or deviant behavior may be stored locally in the vehicle mounted monitoring system or transmitted to the central fleet management system. In an embodiment, the resolution/compression quality of the driver behavior recorded by the driver facing camera may be adjusted during the improper or deviant behavior to improve or otherwise enhance the video quality to reflect that this is a head pose driver behavior event.

The driver behavior monitoring system of the embodiment determines a driver's head pose using the driver-facing camera, logic and a processor executing the logic, determines a distribution of the head pose over time, and monitors the distribution of the head pose, for warning the driver when this deviates from a desired or usual distribution. A warning signal may be generated and/or a warning event may be triggered for storing data related to the warning signal indicating the head pose deviating from the desired or usual distribution. The warning signal and/or the data related to the warning signal may be transmitted to the central fleet management system.

Overall, the system observes the driver's head pose (facing direction) using the driver facing camera 345. The spatial distribution of the driver's head pose is collected over time, and generate a 3-D histogram of head roll, pitch and yaw is generated. The driver behavior monitoring system is then able to verify that there is a (desired and proper) change in the histogram when the driver is engaged in a vehicle backing activity, when engaged in a turning (look left when turning left, for instance) activity, and when performing other actions with the vehicle. By means of change detection methods, significant deviations from the driver's normal pose distribution may be detected from the head pose data collected, and the detected deviations may be flagged such as for example by generating a driver head pose deviation signal.

In an embodiment, the histogram is operable on two time scales. That is, the histogram is operable on a long time scale, for learning or otherwise developing the driver's 'average' behavior, and the histogram is operable on a short time scale, for learning or otherwise developing the driver's 'what is happening now' driver behavior. The two histograms are compared in the embodiment.

Figure 16:
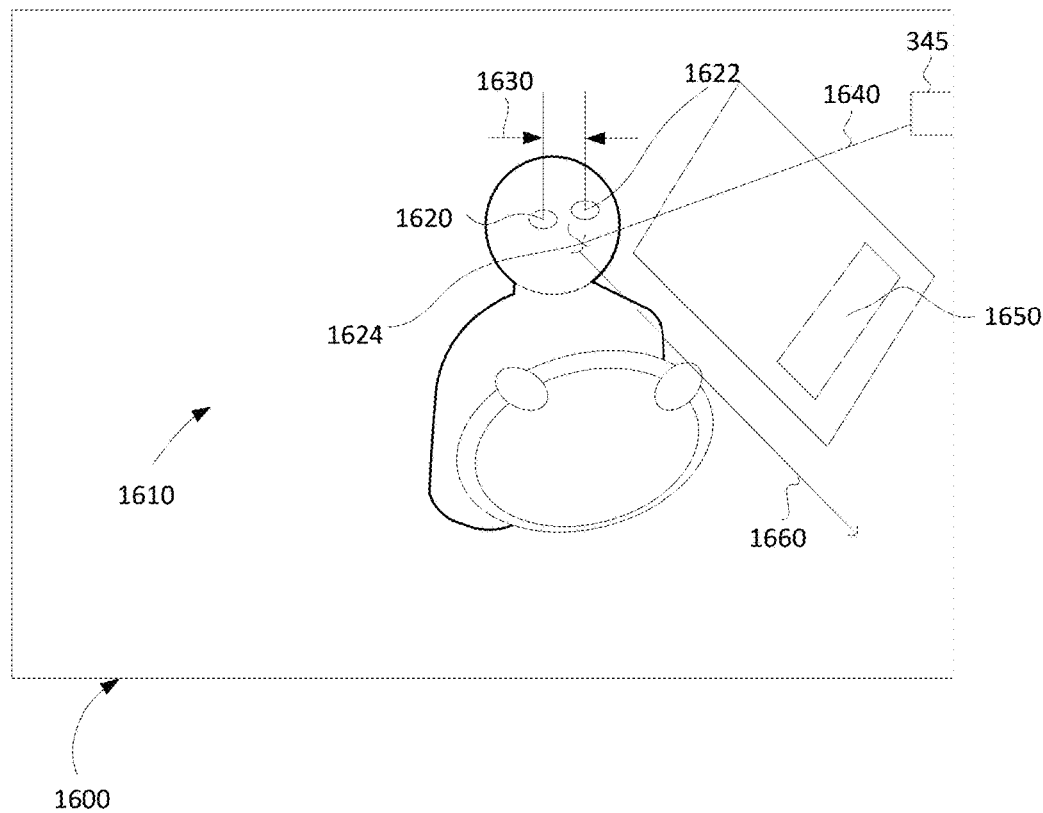
FIG. 16 is a schematic diagram showing characteristics of a driver's head for purposes of determining a driver's head pose vector in accordance with an example embodiment.

FIG. 16 is a diagrammatic showing an image 1600 (not taken by the driver facing camera of the embodiments) of a cabin 1610 of an associated vehicle illustrating the driver facing camera 345 in accordance with the embodiment imaging a properly seated driver 1612 appropriately looking at the vehicle mirror 1650. The driver behavior monitoring system and fits a head pose model shown in the drawing Figure as a driver's head pose vector 1660 originating at the driver's nose 1624. This vector 1660 may be visualized as a rigidly affixed handle connected to a generic 3-D face model. The face model is tilted, turned, and adjusted angularly and scale-wise until it fits the observed face as closely as possible. The 3-D angles corresponding to the handle are the head pose. It is to be appreciated that the head pose model embraces and otherwise includes driver head location information, driver head roll information, and driver head pitch and yaw information.

As described above, for the subject driver facing camera 345, the system fits a head model to the driver's appearance, thereby obtaining a facial normal vector 1660. The head model, which is generic, is rotated and scaled in 3-D space until it fits the undistorted image of the driver's head as well as possible. The system thereby has the three angles characterizing the head pose, to within generic head model limits, and a scale factor. The driver head pose angles include, for example, a driver's head pitch angle (driver looking down or up), a driver's head yaw angle (driver looking left or right), and a driver's head roll angle (driver tilting his/her head to the left or right).

The system does not, however, have or otherwise know the absolute distance 1640 (FIG. 16) from the camera 345 to the driver 1612, that is, the system does not have or otherwise know 3-D driver head location information (just the angles). The typical pupillary distance 1630 limits can give the system a bound, wherein women have a mean pupillary distance of 61.7 mm, and men have a mean pupillary distance of 64.0, both with a standard deviation of ~3.5 mm. This renders a head distance to within ~+/−10% for ~95% of the human population in general. That is, in the embodiment, the system first preferentially looks for driver gender, then takes the corresponding inter-pupillary distance 1630 eye center 1620 to eye center 1622 and relates the image head eye spacing to distance from the camera. Since the system has the head pose angles, the system can determine or otherwise calculate the inter-pupillary distance 1630 in pixels as if the driver 1612 were directly facing the camera 345. Then, using pixel size, the system determines the interpupillary distance 1630 in meters, apply the lens focal length. Via similar triangles, the system calculates the distance between the camera 345 and the driver's 1612 head as:

Head to camera distance=(lens focal length*gender interpupillary distance)/(facing the camera in the image interpupillary distance).

For instance, if there are 20 pixels separating the pupils (or eye centers 1620, 1622, taken as proxies for the pupils), and pixels are 4 microns in size, then there are 80 micrometers between the pupils. If, furthermore, the lens focal length is 2 millimeters, and driver gender is determined as male, then the camera to driver head distance is (2 mm*64 mm/80 micrometers) or 1.6 meters.

With the distance, the system is able to locate the driver's head in 3-D space, and then use the facial normal vector 1660 direction to relate to the vehicle cabin, mirrors, gauges, road, etc. As the facial normal vector 1660 typically originates at the nose tip 1624, the camera to head distance is known, and the angle to the head via the nose tip location in the image is also known, the system of the example embodiment calculates the facial normal vector location in space, and verifies that the facial normal vector "points" or is otherwise directed at or to the desired regions around the driver, such as mirrors, road, next lane when passing, etc.

The system may collect data over a selectable period of time such as, for example, over the last 120 seconds of the driver's head pose, entering this collected data into a multi-dimensional histogram stored in the local memory of the system. It is preferred that a circular list supplemented with a pointer to the oldest entry computational structure may form the data storage backbone feeding this histogram.

The histogram may then be compared with an observed safe condition. The observed safe condition may possibly be derived from the statistics of one or more accident-free time histories, or from one or more predetermined set of statistics of accident-free time history models. Still further, the histogram may be compared with a desired histogram of the fleet associated with the vehicle. Examples of comparing histograms are disclosed, for example, in Serratosa F., Sanromà G., Sanfeliu A. (2007) "A New Algorithm to Compute the Distance Between Multi-dimensional Histograms" In: Rueda L., Mery D., Kittler J. (eds) *Progress in Pattern Recognition, Image Analysis and Applications*. CIARP 2007. Lecture Notes in Computer Science, vol 4756. Springer, Berlin, Heidelberg, the teachings of which are incorporated herein by reference.

Figure 17:
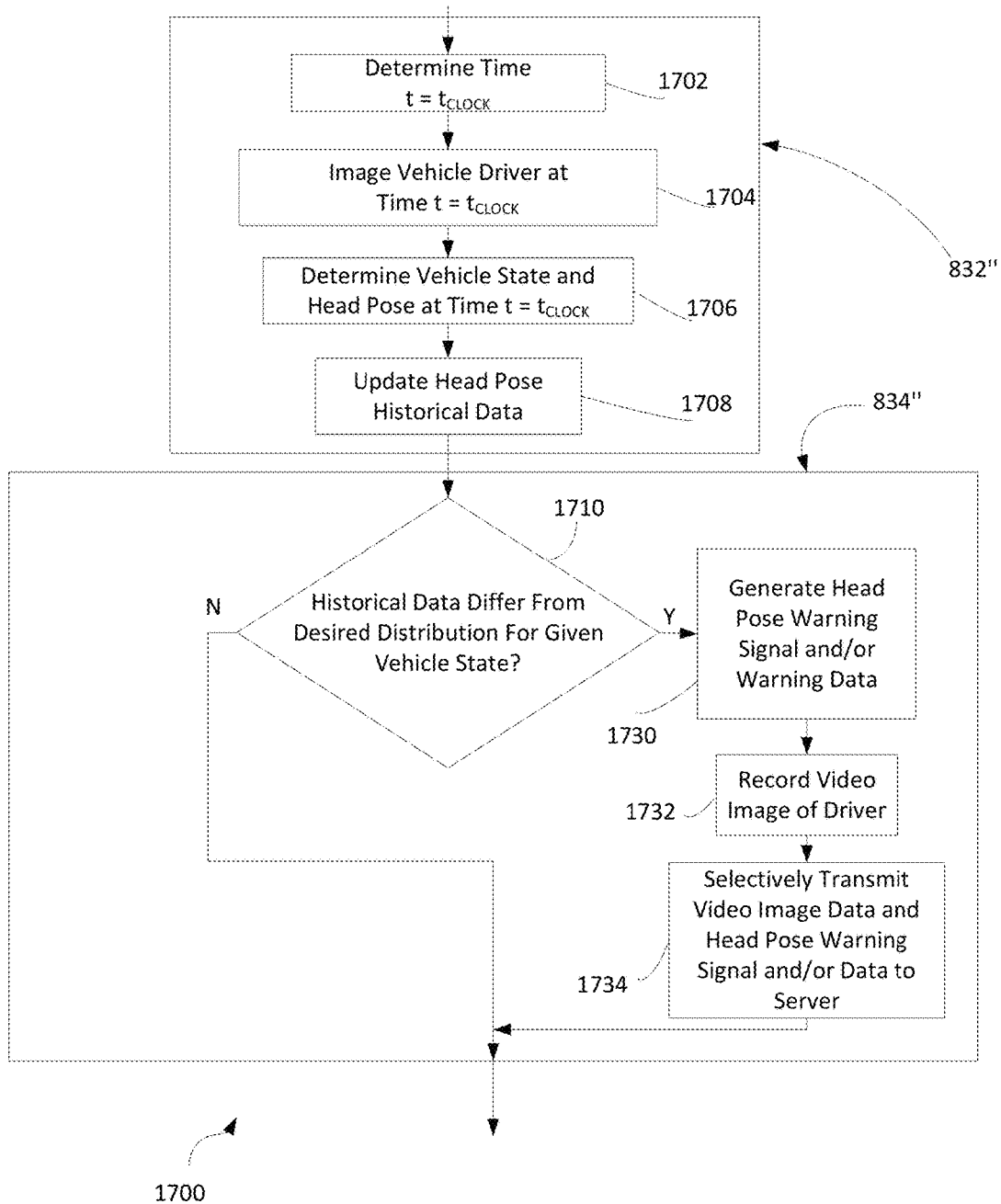
FIG. 17 is a flow diagram showing a method of operating a driver behavior monitoring system having a driver facing camera for detecting, monitoring, and reporting whether the driver's head pose distribution is significantly changing or unacceptable implementing a driver road attention strategy in accordance with an example embodiment.

FIG. 17 is a flow diagram showing a method of operating a driver behavior monitoring system having a driver facing camera for detecting, monitoring, and reporting whether the driver's head pose distribution is significantly changing or unacceptable implementing a driver road attention strategy in accordance with an example embodiment. With reference now to that Figure, in the method 1700 of the embodiment, the driver image data collection portion 832' includes a step 1702 determining a time of the image of the driver, and a step 1704 collecting the image of the driver. In step 1106 the logic of the system determines information relating to the operation of the vehicle such as, for example, vehicle speed data or the like, and the logic also determines the head pose of the driver. The historical driver's head pose data is updated in step 1708 with the newly acquired driver's head pose.

A determination is made in step 1710 whether the collected historical data differs from a predetermined desired distribution for a given vehicle state. If the collected historical data does not differ from the predetermined desired distribution for the given vehicle state, no action is taken. However, if the collected historical data does differ from the predetermined desired distribution for the given vehicle state, then the method 1700 generates at step 1730 a head pose warning signal and/or generates head pose warning data. A video image of the driver is recorded or otherwise collected at step 1732, and the head pose warning signal and/or the head pose warning data is selectively transmitted in step 1734 together with the video image of the driver to a central fleet management system or the like. Alternatively, the video image of the driver and the head pose warning signal and/or the head pose warning data may be selectively stored in a memory device of the driver monitoring system local to the vehicle.

Figure 18:
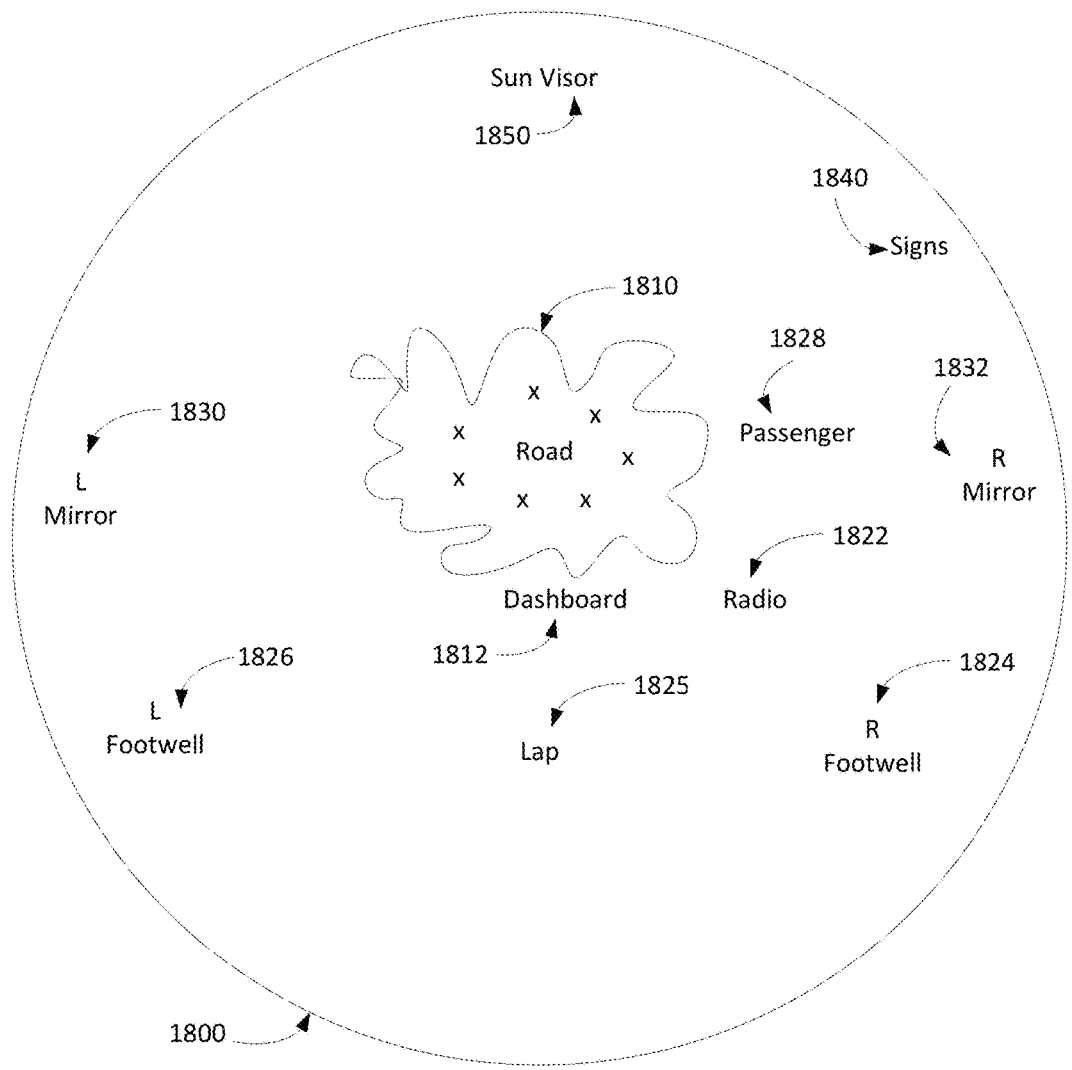
FIG. 18 is an example of a head pose distribution map in accordance with an example embodiment.

FIG. 18 is an example of a head pose distribution map 1800 in accordance with an example embodiment. As illustrated in that Figure, a visualization and analysis framework of the head pose distribution may be performed in spherical coordinates, mapping to named locations. The mapped locations may include, for example, a location of the vehicle radio 1822, a location of the right and left footwells of the vehicle 1824 and 1826, a location of the driver's lap 1825, a location of a passenger in the vehicle 1828, a location of the left and right mirrors of the vehicle 1830 and 1832, a location of the sunvisor of the vehicle 1850, or a location of the roadway straight ahead 1850. A color tinted "heat" map (i.e. histogram) may indicate the frequency with which each location is faced is illustrated in that Figure wherein the heat map having the highest driver focus intensity is sketched with "x" markers for the presumably often viewed forward roadway ahead of the vehicle. Portions of the map may be associated to labels—for instance, when the radio station is being changed and the driver is not facing forward in the normal pose, and somewhat to the right, then the map area being faced may be labeled radio (or the likelihood of it being the radio increases). Similar labeling schemes may be used for the mirrors, this time triggered by a set blinker turn signal, and the driver turning left or right, in the sense of the turn signal.

It should be observed that the safe driving position may vary, temporarily or longer term. For instance, the user may need to adjust a control that is further away (e.g. a fan, perhaps) or the user may change the seat position (e.g. to relieve a sore back). We may therefore need to perform a histogram restart or mask out measurement values when these, perhaps temporary, perhaps persistent, changes occur.

Figure 19:
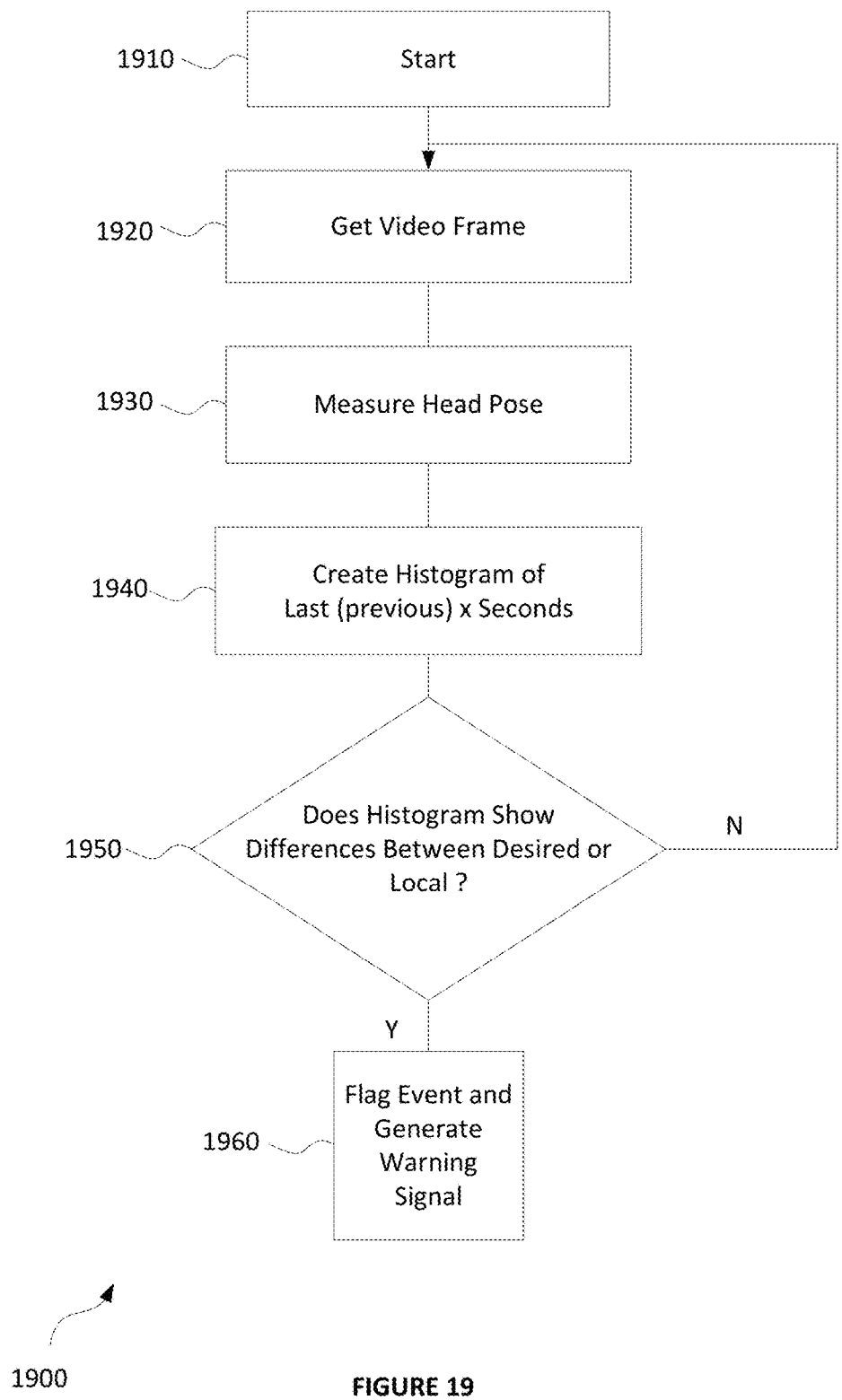
FIG. 19 is a flow diagram showing a method of comparing driver head pose histograms, and determining and reporting deviations and/or changes between the driver head pose histograms.

FIG. 19 is a basic flow diagram showing a method 1900 of comparing driver head pose histograms, and determining and reporting deviations and/or changes between the driver head pose histograms in accordance with an embodiment. Turning now to that Figure, the method 1900 determines improper or deviant driver head direction behavior based on a driver's head pose distribution metric. The method 1900 includes a start step 1910 which, thereafter, initiates a step 1912 of the system imaging the driver and cabin of the associated vehicle and obtaining driver image data. The driver's head pose is measured in step 1914, and a driver's head pose histogram of the last n seconds of driver head image capturing is created in step 1916.

Next, in step 1920 the system determines whether the histogram shows a difference between the desired driver behavior and the actual driver behavior. If there is no difference between the desired driver behavior and the actual driver behavior, or if the difference is within a predetermined bounds, the system repeats step 1912 whereupon the system again images the driver and cabin of the associated vehicle and obtains new driver image data. On the other hand, if there is a difference between the desired driver behavior and the actual driver behavior, or if the difference is outside of the predetermined bounds, the system initiates step 1922 whereupon the system generates the driver inattention signal as determined based on the driver's head pose distribution metric.

Figure 19A:
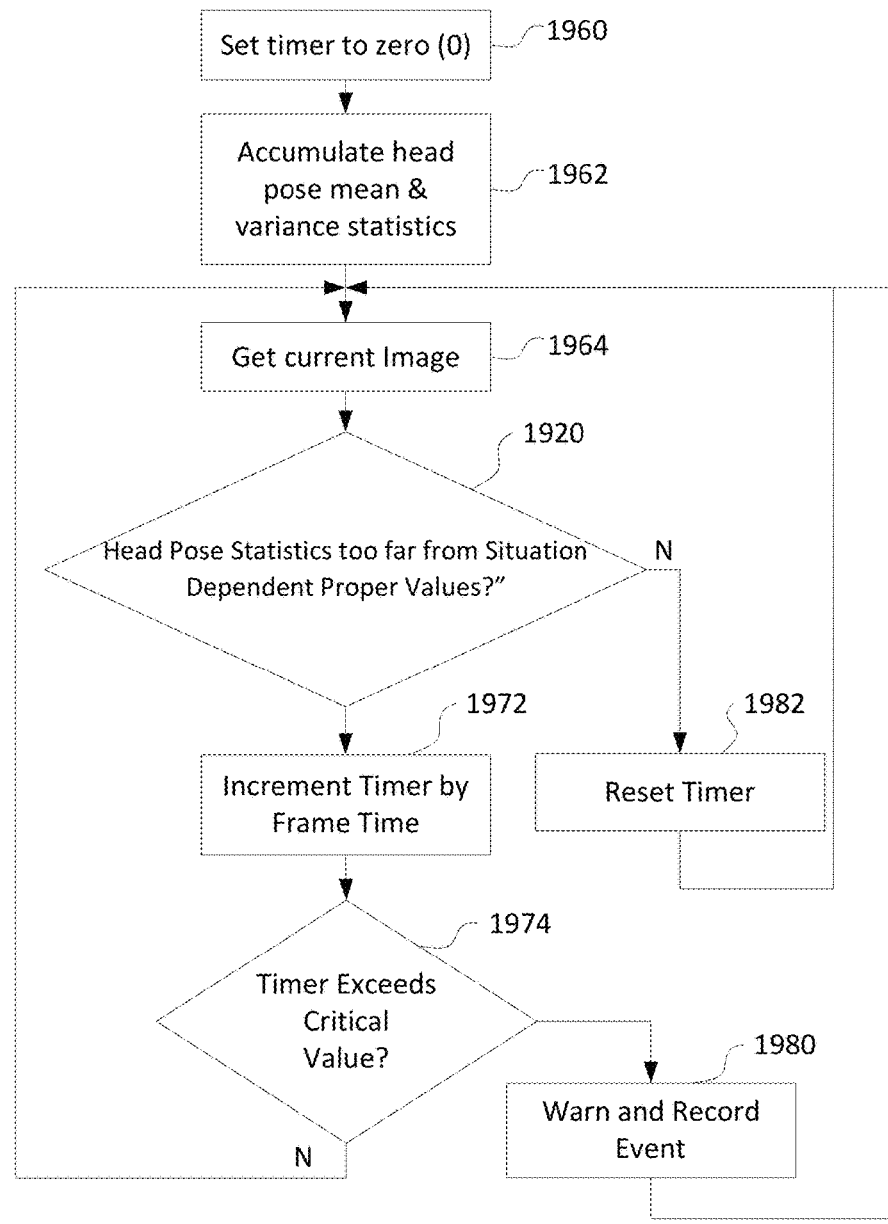
FIG. 19a is a flow diagram showing a method of comparing head pose statistics, and determining and reporting deviations between a driver's head pose and desired, situation appropriate, statistics in accordance with an example embodiment.

FIG. 19a is a flow diagram showing a method 1950 of determining whether the driver's head is out of position in accordance with an example embodiment, with a particular focus on collecting statistics of a "normal" driver's head pose such as, for example while the vehicle is moving sufficiently fast enough and for a sufficiently long enough period, prior to assessing the driver's head pose in accordance with the collected statistics. A timer is initialized in step 1960, and the driver's head pose statistics are collected at step 1962. Preferably, the driver's head pose statistics are collected when the vehicle is moving quickly enough, and for long enough. The driver's head pose mean and variance values need in the example embodiment, some time to develop before they have any practical value such as, for example, on the scale of about one (1) minute at speed. Only after driver's head pose mean and variance values are collected and developed at step 1962 does the system of the embodiment know what is 'regular' driving for this driver, and only then does the system perform driver's head pose testing. This test consists of imaging the driver to obtain at step 1964 a current driver's image. A comparison is performed at step 1970 between the current measured head pose values (yaw, pitch, roll, location) and the mean values of these driver head pose angles including for example a driver's head pitch (driver looking down or up), a driver's head yaw (driver looking left or right), and a driver's head roll (driver tilting his/her head to the left or right) developed at step 1962. If any of these deviates by more than a selectable amount of standard deviations, preferably about two (2) standard deviations from the corresponding mean, the system deems the driver's head to be out of position. A timer is started in step 1972 when the head is out of position. Should the value of the timer exceed a threshold as determined at step 1974, a warning is issued at step 1980. When the head is not out of position, the timer is reset to zero at step 1982.

Figure 20:
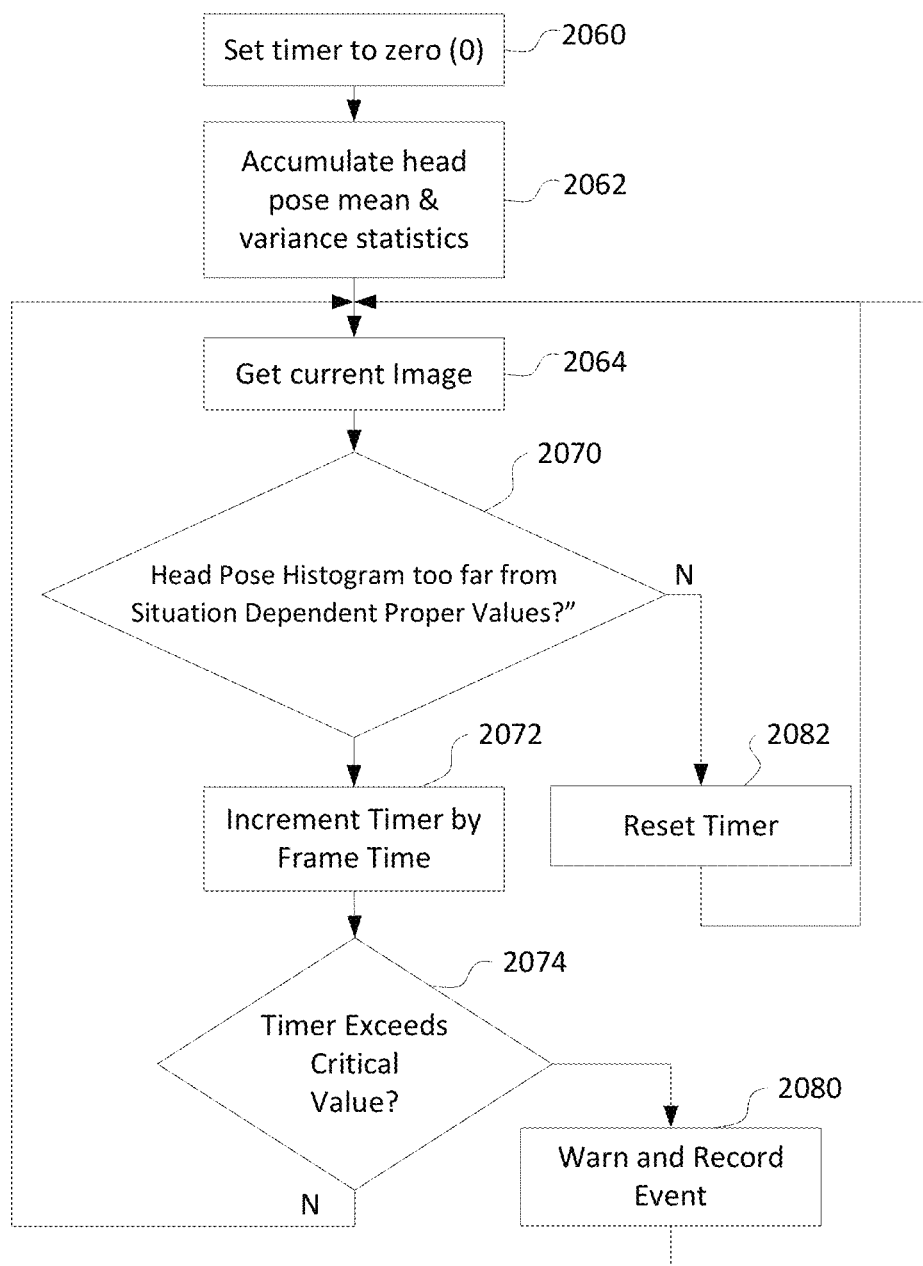
FIG. 20 is a flow diagram showing a method of comparing head pose histograms, and determining and reporting deviations between a driver's head pose and desired, situation appropriate, histograms in accordance with an example embodiment.

FIG. 20 is a flow diagram showing a method 2000 of comparing head pose distribution maps, and determining and reporting deviations between the actual map and a desired, situation appropriate, map in accordance with an example embodiment. The embodiment has a particular focus on collecting statistics of a "normal" driver's head position such as, for example while the vehicle is moving sufficiently fast enough and for a sufficiently long enough period, prior to assessing the driver's head out of position in accordance with the collected statistics. A timer is initialized in step 2060, and the driver's head pose statistics are collected at step 2062. Preferably, the driver's head pose statistics are collected when the vehicle is moving quickly enough, and for long enough. The driver's head pose mean and variance values need in the example embodiment, some time to stabilize before they have any practical value such as, for example, on the scale of about one (1) minute at speed. Only after driver's head pose mean and variance values are collected and developed at step 2062 does the system of the embodiment know what is 'regular' driving for this driver, and only then does the system perform driver's head out of position testing. This test first consists of imaging the driver to obtain at step 2064 a current driver's image. A comparison is performed at step 2070 between the current measured head pose values (yaw, pitch, roll, location) and a histogram of driver head pose angles including for example a driver's head pitch (driver looking down or up), a driver's head yaw (driver looking left or right), and a driver's head roll (driver tilting his/her head to the left or right) developed at step 2062. If any of these deviates by more than a selectable amount of standard deviations, preferably about two (2) standard deviations from the corresponding mean, the system deems the driver's head to be out of position. A timer is incremented in step 2072 when the head is out of position. Should the value of the timer exceed a threshold as determined at step 2074, a warning is issued at step 2080. When the head is not out of position, the timer is reset to zero at step 2082.

Driver's Eyes on Road with Adaptive LDW Warning Margin

Drivers not properly looking at the road when driving forward will likely need a longer time to react to a dangerous situation. It is therefore desirable to adjust the warning parameters for a danger detection system, such as a lane departure warning device or a radar-based distance keeping aid, such that the driver is warned in a more timely fashion.

The system of the example embodiment therefore couples the time the driver is not looking at the road ahead with an increased warning margin parameter. A linear relationship may be used for instance, such as:

Warning parameter=base warning parameter value+
(factor*(elapsed time since driver has last
looked at road)).

In the example embodiment, the resulting warning parameter value is then capped at some maximum value and/or number, which may be selectable by the driver, a fleet manager, or the like. The elapsed time since the driver has last looked at the road may have, in accordance with a further embodiment, a 'grace period' value subtracted before it is used in the above equation. This beneficially allows the driver to briefly glance away, during which time the vehicle warning systems do not change their parametrization. It is understood that an equivalent negative value version or an adjustment in a decreasing magnitude sense for the above equation may also apply, as required by the application using the parameter.

The factor in the above equation may be adjusted within limits so that a desired driver behavior is maintained, e.g. so that the headway time stays greater than some minimum value for at least 95% of the time. This adjustment may be made by the driver or from a fleet command center, which can observe the driver's safety relevant behavioral statistics.

Driver's Mirror Usage Verification

Commercial vehicle drivers have many tasks to coordinate during vehicle operation. One of these tasks is scanning the vehicle mirrors. When the vehicle mirror scanning is not done properly or is not done with sufficient frequently, collision risk increases.

It is desirable, therefore to provide a system, method and apparatus for verifying the sufficiency and adequacy of the drover's mirror usage. In accordance with an embodiment, the driver facing camera 345 is used to verify the driver's proper use of the mirrors of the vehicle.

The embodiments advantageously provide improvements in vehicle operation by helping to increase driving safety, both for commercial and other vehicles as well as for other vehicles around the vehicle having the driver behavior monitoring systems, methods and apparatus of the embodiments herein including in particular the embodiment providing mirror usage verification. The embodiment further provide characterization of the driver such as, for example, biometric ID information, and warn the driver and remote fleet management if any unsafe behavior occurs or is detected.

Algorithms for finding faces in images use a model of the human face. This model typically looks for facial 'landmarks', that is, contrasting, distinct, areas, such as the corners of the mouth, eyes, etc. When a configuration of such landmarks is found that is within the geometric expectations for human facial appearance, the face is located.

The configuration of the landmarks relates to the direction in which the face points (its 'pose') relative to the camera. The pose may be summarized by a 3-dimensional vector originating at the person's nose as shown in FIGS. 5*a* and 17 as a 3-D head pose vector 522.

It may also be seen that the face has been located (chin, mouth, eyes, etc), placing it within a certain volume in the passenger cabin. The tip of the nose is located on a ray emanating from the camera, and on average approximately centered on the seat and pointing straight forward.

Figure 21:
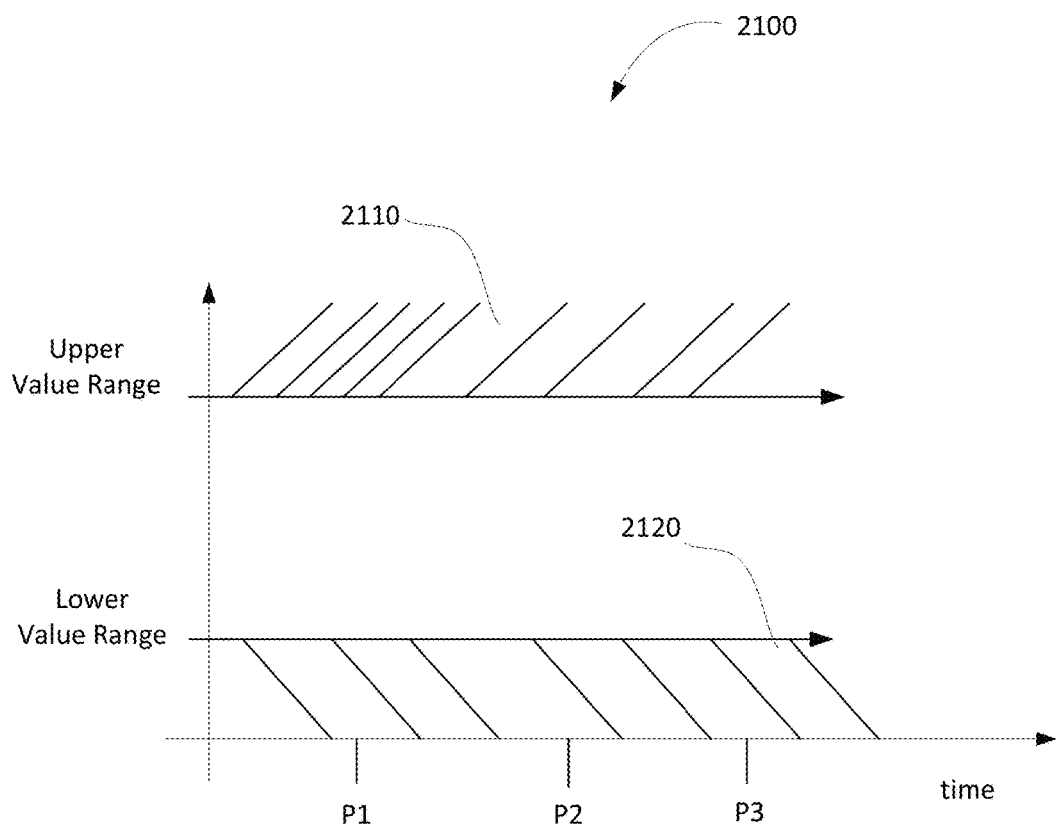
FIG. 21 is an illustration of the bounds applying to mirror usage in accordance with an example embodiment.

FIG. 21 is an illustration of the bounds applying to mirror usage in accordance with an example embodiment. The system of the embodiment relates the facial pose vector 522, together with the head position, to see in what direction the driver is facing (not necessarily the same as looking, or gazing). Though glancing by eye motion only at the mirrors is possible, the system examines the facial pose vector 522 over time to determine whether the driver is moving their head to look—as they should—at the mirrors. When the driver is not looking at the mirrors often enough 2120—or perhaps for too long 2110 (after all, one should mostly look forward when driving forward, for example), a warning is issued, and a Safety Event Recording may be triggered, and statistics regarding driver behavior may be collected.

The system of the embodiment can thus use the driver facing camera 345 (whose position and geometry is known, together with the driver's head location and pose, to increase safety, enforce policy, look for hints of fatigue, and collect safety and driver behavior statistics.

A particular case of mirror usage verification is that of changing lanes. Good driving practice states that the mirror associated with the lane that one is changing into shall be used before the lane change is made. Therefore, when the turn signal is set, for example, the system of the example embodiment executes a test for using the mirror before the lane change. The test may be, for example, to determine whether the driver looked at the appropriate mirror for long enough (between the upper 2110 and lower 2120 bands) before the lane change. Equivalently, if the turn signal is not set, but the lane is changed (an event detectable by a lane departure warning system), and the mirror is not looked at, then this 'not using the mirror before a lane change is detected' event is also triggered.

A similar test for mirror usage may be performed when a driver is standing still and blinking to the right. This is a classic, dangerous, situation for any cyclists located on a commercial vehicle's right side, where they may be crushed by the turning truck. One may therefore enforce proper mirror usage by verifying that the driver has looked to the right before the vehicle moves again, that is, create a visual interlock on vehicle movement. It is understood that the left side version of this may also be similarly implemented in regions where left-side traffic is the norm.

In accordance with an embodiment, a system monitoring a driver attention condition of an associated vehicle during operation of the associated vehicle by an associated driver is provided. The system includes an imaging device disposed in the associated vehicle, a control device including a processor, and an output operatively coupled with the processor. The imaging device captures an image of the associated driver disposed in the associated vehicle and of an interior of the associated vehicle, and generates image data representative of the captured image of the associated driver disposed in the associated vehicle and of the interior of the associated vehicle, The control device includes an image data input operatively coupled with the processor, a non-transient memory device operatively coupled with the processor, driver head detection logic stored in the non-transient memory device, driver head direction logic stored in the non-transient memory device, and control logic stored in the non-transient memory device.

The image data input receives the image data from the imaging device. The non-transient memory device stores vehicle geometry data representative of relative positions between one or more structures of the associated vehicle, imaging device position data representative of a position of the imaging relative to the one or more structures of the associated vehicle, and safe attention model data comprising a recommended value range of a driver road attention parameter of the monitored driver attention condition of the associated vehicle.

The driver head detection logic is executable by the processor to process the image data to locate/determine a head candidate area of the image captured by the imaging device likely above a predetermined threshold stored in the non-transient memory device to be representative of the head of the associated driver disposed in the associated vehicle, and tag a portion of the image data corresponding to the head candidate area located/determined by the driver head detection logic as driver head image data.

The driver head direction logic is executable by the processor to process the driver head image data to determine a facing direction of the head of the associated driver, and generate driver head facing direction data, the driver head facing direction data being representative of the determined facing direction of the head of the associated driver.

The control logic is executable by the processor to process the driver head facing direction data together with the vehicle geometry data and the imaging device position data to determine an operational value of the driver road attention parameter of the monitored driver attention condition of the associated vehicle, and perform a comparison between the recommended value range of the driver road attention parameter of the monitored driver attention condition of the associated vehicle and the determined operational value of the driver road attention parameter of the monitored driver attention condition of the associated vehicle.

The control logic is further executable by the processor to determine a state of vehicle operation compliance in accordance with a result of the comparison between the recommended value range and the determined operational value of the driver road attention parameter of the monitored driver attention condition of the associated vehicle.

The control logic may in accordance with an example determine the state of the vehicle operation compliance as a one of a driver inattention state in accordance with a first result of the comparison between the recommended value range and the determined operational value of the driver road attention parameter of the monitored driver attention condition of the associated vehicle, wherein the processor generates driver inattention data in accordance with the first result, or a driver attention state in accordance with a second result of the comparison between the recommended value range and the determined operational value of the driver road attention parameter of the monitored driver attention condition of the associated vehicle.

The an output selectively receives the driver inattention data from the processor and generates a driver inattention signal representative of the determined operational value of the driver road attention parameter of the monitored driver attention condition being outside of the recommended value range of the safe model data.

In accordance with a further example embodiment, the control logic is executable by the processor to process driver head facing direction data together with vehicle geometry data and imaging device position data to determine an operational value of the driver road attention parameter of the monitored driver attention condition of the associated vehicle, correlate the driver road attention parameter of the monitored driver attention condition of the associated vehicle with an operational value of a parameter of a lane departure warning (LDW) monitored condition of the associated vehicle, and determine an adjustment value for modifying setting a LDW system of the associated vehicle in accordance with the driver road attention parameter of the monitored driver attention condition of the associated vehicle correlated with the operational value of the parameter of the LDW monitored condition of the associated vehicle. The output is operatively coupled with an input of the LDW system of the associated vehicle, and selectively receives the adjustment value for modifying the LDW setting, and delivers the adjustment value to the associated vehicle.

It is now claimed:

1. A safety system monitoring a condition of an associated driver of an associated vehicle during operation of the associated vehicle by the associated driver, the system comprising:

an imaging device disposed in the associated vehicle, the imaging device capturing an image of the associated driver disposed in the associated vehicle and generating image data representative of the captured image of the associated driver disposed in the associated vehicle; and a control device comprising: a processor;

an image data input operatively coupled with the processor, the image data input receiving the image data from the imaging device;

a non-transient memory device operatively coupled with the processor, the non-transient memory device storing preferential safety model data comprising first and second recommended value ranges of a parameter of the monitored condition of the associated driver, the first recommended value range corresponding to an operational condition of the associated vehicle moving forward and the second recommended value range corresponding to an operational condition of the associated vehicle moving backwards; and control logic stored in the non-transient memory device, the control logic being executable by the processor to:

process the image data to determine an operational value of the parameter of the monitored condition of the associated driver;

selectively for the operational condition of the associated vehicle moving forward, perform a comparison between the first recommended value range of the parameter of the monitored condition of the associated driver and the operational value of the monitored condition of the associated driver:

selectively for the operational condition of the associated vehicle moving backwards, perform a comparison between the second recommended value range of the parameter of the monitored condition of the associated driver and the operational value of the monitored condition of the associated driver; and determine a state of vehicle operation compliance in accordance with a result of the comparison between the first or second recommended value ranges and the operational value of the parameter of the monitored condition of the associated driver, wherein the processor generates result data in accordance with the result;

an output operatively coupled with the processor, the output selectively receiving the result data from the processor and generating a compliance result signal representative of the operational value of the parameter of the monitored condition.

2. The safety system according to claim 1, wherein:

the control logic is executable by the processor to determine the state of vehicle operation compliance as a one of:

a non-compliance state in accordance with a first result of the comparison between the first or second recommended value ranges and the operational value of the parameter of the monitored condition of the associated driver, wherein the processor generates non-compliance data in accordance with the first result, or a compliance state in accordance with a second result of the comparison between the first or second recommended value ranges and the operational value of the parameter of the monitored condition of the associated driver; and the output selectively receives the non-compliance data from the processor and generates a non-compliance signal representative of the operational value of the parameter of the monitored condition being outside of the first or second recommended ranges of the safe model data.

3. The safety system according to claim 1, wherein:

the preferential safety model data comprises a plurality of recommended value ranges, each of the plurality of recommended value ranges corresponding to an operational condition of the associated vehicle.

4. A system monitoring a driver attention condition of an associated vehicle during operation of the associated vehicle by an associated driver, the system comprising:

an imaging device disposed in the associated vehicle, the imaging device capturing an image of the associated driver disposed in the associated vehicle and of an interior of the associated vehicle, and generating image data representative of the captured image of the associated driver disposed in the associated vehicle and of the interior of the associated vehicle; and a control device comprising:

a processor;

an image data input operatively coupled with the processor, the image data input receiving the image data from the imaging device;

a non-transient memory device operatively coupled with the processor, the non-transient memory device storing vehicle geometry data representative of relative positions between one or more structures of the associated vehicle, imaging device position data representative of a position of the imaging relative to the one or more structures of the associated vehicle, and safe attention model data comprising first and second recommended value ranges of a driver road attention parameter of the monitored driver attention condition of the associated vehicle, the first recommended value range corresponding to an operational condition of the associated vehicle moving forward and the second recommended value range corresponding to an operational condition of the associated vehicle moving backwards;

driver head detection logic stored in the non-transient memory device, the driver head detection logic being executable by the processor to:

process the image data to locate/determine a head candidate area of the image captured by the imaging device likely above a predetermined threshold stored in the non-transient memory device to be representative of the head of the associated driver disposed in the associated vehicle; and tag a portion of the image data corresponding to the head candidate area located/determined by the driver head detection logic as driver head image data;

driver head direction logic stored in the non-transient memory device, the driver head direction logic being executable by the processor to:

process the driver head image data to determine a head pose vector as a facing direction of the head of the associated driver; and generate driver head facing direction data, the driver head facing direction data being representative of the determined facing direction of the head of the associated driver;

control logic stored in the non-transient memory device, the control logic being executable by the processor to:

process the driver head facing direction data together with the vehicle geometry data and the imaging device position data to determine an operational value of the driver road attention parameter of the monitored driver attention condition of the associated vehicle;

selectively for the operational condition of the associated vehicle moving forward, perform a comparison between the first recommended value range of the driver road attention parameter of the monitored driver attention condition of the associated vehicle and the determined operational value of the driver road attention parameter of the monitored driver attention condition of the associated vehicle;

selectively for the operational condition of the associated vehicle moving backwards, perform a comparison between the second recommended value range of the driver road attention parameter of the monitored driver attention condition of the associated vehicle and the determined operational value of the driver road attention parameter of the monitored driver attention condition of the associated vehicle; and determine a state of vehicle operation compliance as a one of:

a driver inattention state in accordance with a first result of the comparison between the first or second recommended value ranges and the determined operational value of the driver road attention parameter of the monitored driver attention condition of the associated vehicle, wherein the processor generates driver inattention data in accordance with the first result, or a driver attention state in accordance with a second result of the comparison between the first or second recommended value ranges and the determined operational value of the driver road attention parameter of the monitored driver attention condition of the associated vehicle; and an output operatively coupled with the processor, the output selectively receiving the driver inattention data from the processor and generating a driver inattention signal representative of the determined operational value of the driver road attention parameter of the monitored driver attention condition being outside of the first or second recommended value ranges of the safe model data.

5. The system according to claim 4, further comprising:
driver head location logic stored in the non-transient memory device, the driver head location logic being executable by the processor to:
process the driver head image data together with the vehicle geometry data and the imaging device position data to determine a location of the driver's head relative to the one or more controls structures of the associated vehicle; and
generate driver's head location data, the driver's head location data being representative of the determined location of the head of the associated driver relative to the one or more controls structures of the associated vehicle,
wherein the control logic is executable by the processor to process the generated driver's head location data together with the driver head facing direction data, the vehicle geometry data, and the imaging device position data to determine the operational value of the driver road attention parameter of the monitored driver attention condition of the associated vehicle.

6. The system according to claim 5, wherein:
the driver head direction logic is executable by the processor to:
process the driver's head location data to locate facial landmarks fitted against a head model to determine a facial normal vector as the head pose vector of the head of the associated driver, the facial normal vector having an origin at the determined location of the head of the associated driver relative to the one or more controls structures of the associated vehicle; and
generate the driver head facing direction data comprising the facial normal vector.

7. The system according to claim 6, wherein:
the vehicle geometry data stored in the non-transient memory device comprises vehicle windshield data representative of a relative position between a windshield of the associated vehicle and the one or more structures of the associated vehicle;
the safe attention model data in the non-transient memory device comprises a recommended value range of a driver looking at the windshield parameter as a proxy for the driver road attention parameter of the monitored driver attention condition of the associated vehicle;
the control logic is executable by the processor to:
process the driver head location data and the facial normal vector to determine an operational value of the driver looking at the windshield parameter of the monitored driver attention condition of the associated vehicle;
perform a comparison between the recommended value range of the driver looking at the windshield parameter of the monitored driver attention condition of the associated vehicle and the determined operational value of the driver looking at the windshield parameter of the monitored driver attention condition of the associated vehicle; and
determine the state of vehicle operation compliance as a one of:
the driver inattention state in accordance with a first result of the comparison between the recommended value range and the determined operational value of the driver looking at the windshield parameter of the monitored driver attention condition of the associated vehicle, wherein the processor generates driver inattention data in accordance with the first result, or the driver attention state in accordance with a second result of the comparison between the recommended value range and the determined operational value of the driver looking at the windshield parameter of the monitored driver attention condition of the associated vehicle.

8. The system according to claim 5, wherein:
the driver head location logic is executable by the processor to determine the location of the driver's head relative to the one or more controls structures of the associated vehicle by one or more of:
inferring an approximate location of the driver's head relative to the one or more controls structures by locating in the image data a landmark on a driver's seat of the associated vehicle, measuring one or more of a distance to and/or a height of the landmark, and inferring the approximate location of the driver's head relative to the
one or more controls structures in accordance with the landmark located in the image data;
using driver's head location calibration data representative of a calibrated position of the driver's head relative to the one or more controls structures of the associated vehicle as the determined location of the driver's head relative to the one or more controls structures of the associated vehicle; or
inferring an approximate location of the driver's head relative to the one or more controls structures by locating in the image data a vertical half-seat plane of the driver's seat of the associated vehicle and inferring the approximate location of the driver's head relative to the one or more controls structures in accordance with the vertical half-seat plane of the driver's seat located in the image data.

9. The system according to claim 4, wherein:
the control logic is executable by the processor to:
- sample, over a predetermined time period, the driver head facing direction data, and store the sampled driver head facing direction data into the non-transient memory device as a sequence of driver head facing direction data;
- process the stored sequence of driver head facing direction to determine a typical driver head facing direction range of the sampled driver head facing direction data; and
- store to the non-transient memory device the determined typical driver head facing direction range of the sampled driver head facing direction data as a one of the recommended first or second value ranges of the driver road attention parameter of the monitored driver attention condition of the associated vehicle.

10. The system according to claim 6, wherein:
the vehicle geometry data stored in the non-transient memory device comprises vehicle side mirror data representative of a relative position between a side mirror of the associated vehicle and the one or more structures of the associated vehicle;
the safe attention model data in the non-transient memory device comprises a recommended value range of a driver looking at the side mirror parameter as a proxy for the driver road attention parameter of the monitored driver attention condition of the associated vehicle;
the control logic is executable by the processor to:
process the driver head location data, the facial normal vector, and the vehicle side mirror data to determine an operational value of the driver looking at the mirror windshield parameter of the monitored driver attention condition of the associated vehicle;
perform a comparison between the recommended value range of the driver looking at the mirror parameter of the monitored driver attention condition of the associated vehicle and the determined operational value of the driver looking at the mirror parameter of the monitored driver attention condition of the associated vehicle; and determine the state of vehicle operation compliance as a one of:
the driver inattention state in accordance with a first result of the comparison between the recommended value range and the determined operational value of the driver looking at the mirror parameter of the monitored driver attention condition of the associated vehicle, wherein the processor generates driver inattention data in accordance with the first result, or
the driver attention state in accordance with a second result of the comparison between the recommended value range and the determined operational value of the driver looking at the mirror parameter of the monitored driver attention condition of the associated vehicle.

11. The system according to claim 10, wherein: the safe attention model data comprises:
a recommended upper value range of the driver looking at the side mirror parameter of the monitored driver attention condition of the associated vehicle; and
a recommended lower value range of the driver looking at the side mirror parameter of the monitored driver attention condition of the associated vehicle; the control logic is executable by the processor to:
sample, over a predetermined time period, the driver head facing direction data, and store the sampled driver head facing direction data into the nontransient memory device as a sequence of driver head facing direction data;
process the stored sequence of driver head facing direction data to determine, during a predetermined monitored period, a driver mirror usage ratio as a ratio between an amount of time during the predetermined monitored period that the driver head facing direction data is representative of the head of the associated driver facing the side mirror and an amount of time during the predetermined monitored period that the driver head facing direction data is representative of the head of the associated driver not facing the side mirror;
compare the driver mirror usage ratio with the recommended upper and lower value ranges of the driver looking at the side mirror parameters of the monitored driver attention condition of the associated vehicle;
selectively generate the driver inattention data in accordance with the driver mirror usage ratio being:
greater than the recommended upper value range of the driver looking at the side mirror parameter of the monitored driver attention condition of the associated vehicle or less than the recommended lower value range of the driver looking at the side mirror parameter of the monitored driver attention condition of the associated vehicle.

12. The system according to claim 6, wherein:
the control logic is executable by the processor to:
determine, over a predetermined detection time, a mean head position value of the facial normal vector;
determine, over the predetermined detection time, a variance of the mean head position value of the facial normal vector; and
determine, over the predetermined detection time, a standard deviation of the variance of the facial normal vector.

13. The system according to claim 12, wherein:
the non-transient memory device stores, as the driver road attention parameter of the safe attention model data, a recommended value range of a driver head out of position parameter of the monitored driver attention condition as a selectable multiple of the determined standard deviation of the variance of the facial normal vector, the control logic stored in the non-transient memory device is executable by the processor to:
process the facial normal vector to determine an operational value of the driver road attention parameter of the monitored driver attention condition of the associated vehicle;
perform a comparison between the recommended value range of the driver head out of position parameter of the monitored driver attention condition of the associated vehicle and the determined operational value of the driver head out of position parameter of the monitored driver attention condition of the associated vehicle; and
determine the state of vehicle operation compliance as a one of:
the driver inattention state in accordance with a first result of the comparison between the recommended value range and the determined operational value of the driver head out of position parameter of the monitored driver attention condition of the associated vehicle, wherein the processor generates the driver inattention data in accordance with the first result, or
the driver attention state in accordance with a second result of the comparison between the recommended value range and the determined operational value of the driver head out of position parameter of the monitored driver attention condition of the associated vehicle.

14. The system according to claim 12, wherein:
the control logic is executable by the processor to:
determine, over a predetermined detection time, a mean head position value of the facial normal vector in first, second, and third axes;
determine, over the predetermined detection time, a variance of the mean head position value of the facial normal vector in the first, second, and third axes; and
determine, over the predetermined detection time, a standard deviation of the variance of the facial normal vector in the first, second, and third axes.

15. The system according to claim 14, wherein:
the non-transient memory device stores, as the driver road attention parameter of the safe attention model data, recommended value ranges of a driver head out of position parameter in the first, second, and third axes of the monitored driver attention condition as a selectable multiple of the determined standard deviation of the variance of the facial normal vector in the first, second, and third axes;
the control logic stored in the non-transient memory device is executable by the processor to:
process the facial normal vector to determine operational values of the driver road attention parameter in the first, second, and third axes of the monitored driver attention condition of the associated vehicle;
perform a comparison between the recommended value ranges of the driver head out of position parameter in the first, second, and third axes of the monitored driver attention condition of the associated vehicle and the determined operational values of the driver head out of position parameter in the first, second, and third axes of the monitored driver attention condition of the associated vehicle; and
determine the state of vehicle operation compliance as a one of:
the driver inattention state in accordance with a first result of the comparison between the recommended value ranges and the determined operational values of the driver head out of position parameter of the monitored driver attention condition of the associated vehicle, wherein the processor generates the driver inattention data in accordance with the first result, or
the driver attention state in accordance with a second result of the comparison between the recommended value ranges and the determined operational values of the driver head out of position parameter of the monitored driver attention condition of the associated vehicle.

16. The system according to claim 6, further comprising:
driver face detection logic stored in the non-transient memory device, the driver face detection logic being executable by the processor to:
process the driver's head location data and the facial normal vector to selectively determine, from the image data, a face of the driver of the associated vehicle; and
generate a one of: driver's facial characteristic data representative of the selectively determined face of the associated driver, or impeded image data representative of an inability of the driver face detection location logic to selectively determine the face of the driver of the associated vehicle from the image data; and an input operatively coupled with the processor, the input selectively receiving from the associated vehicle a vehicle moving signal representative of motion of the associated vehicle,
wherein the control logic is executable by the processor to selectively generate, responsive to the input receiving the vehicle moving signal and to the impeded image data being generated, a obstructed view data representative of an obstruction between the imaging device and the associated driver disposed in the associated vehicle.

17. A system monitoring a driver attention condition of a driver of an associated vehicle during operation of the associated vehicle by an associated driver, the system comprising:
an imaging device disposed in the associated vehicle, the imaging device capturing an image of the associated driver disposed in the associated vehicle and of an interior of the associated vehicle, and generating image data representative of the captured image of the associated driver disposed in the associated vehicle and of the interior of the associated vehicle;
an input operatively coupled with the processor, the input selectively receiving from the associated vehicle a vehicle moving signal representative of an operational condition of the associated vehicle moving forward or of an operational condition of the associated vehicle moving backwards; and
a control device comprising:
a processor;
an image data input operatively coupled with the processor, the image data input receiving the image data from the imaging device;
a non-transient memory device operatively coupled with the processor, the non-transient memory device storing vehicle geometry data representative of relative positions between one or more structures of the associated vehicle, imaging device position data representative of a position of the imaging relative to the one or more structures of the associated vehicle, and safe attention model data comprising first and second recommended value ranges of a driver road attention parameter of the monitored driver attention condition of the associated vehicle, the first recommended value range of the driver road attention parameter corresponding to the operational condition of the associated vehicle moving forward and the second recommended value range of the driver road attention parameter corresponding to the operational condition of the associated vehicle moving backwards;
driver head detection logic stored in the non-transient memory device, the driver head detection logic being executable by the processor to:
process the image data to determine a head candidate area of the image captured by the imaging device likely above a predetermined threshold stored in the non-transient memory device to be representative of the head of the associated driver disposed in the associated vehicle;
driver face detection logic stored in the non-transient memory device, the driver face detection logic being executable by the processor to:
process the image data together with the vehicle geometry data and the imaging device position data to determine one or more foreground objects in the image data and one or more background objects in the image data, the determined one or more foreground objects in the image data being disposed in the associated vehicle between the imaging device and the one or more background objects in the image data;

process the head candidate area of the image data corresponding to the determined one or more foreground objects in the image data to selectively determine, from the image data, a face of the driver of the associated vehicle; and generate impeded image data representative of a relative ability of the driver face detection location logic to determine the face of the driver of the associated vehicle in the head candidate area of the image data; and control logic stored in the non-transient memory device, the control logic being executable by the processor to, responsive to the input receiving the vehicle moving signal:

selectively for the operational condition of the associated vehicle moving forward, perform a comparison between the first recommended value range of the driver road attention condition of the associated driver and the impeded image data representative of the relative ability of the driver face detection location logic to determine the face of the driver of the associated vehicle in the head candidate area of the image data;

selectively for the operational condition of the associated vehicle moving backwards, perform a comparison between the second recommended value range of the driver road attention condition of the associated driver and the impeded image data representative of the relative ability of the driver face detection location logic to determine the face of the driver of the associated vehicle in the head candidate area of the image data; and determine driver attention compliance of the monitored driver attention condition in accordance with a result of the comparison between the first or second recommended value ranges of the driver road attention condition and the impeded image data representative of the relative ability of the driver face detection location logic to determine the face of the driver of the associated vehicle from the head candidate area of the image data, wherein the processor generates driver attention compliance result data in accordance with the determined driver attention compliance.

18. A safety system comprising:

an imaging device disposed in the associated vehicle, the imaging device capturing an image of the associated driver disposed in the associated vehicle and of an interior of the associated vehicle, and generating driver head image data representative of the captured image of the associated driver disposed in the associated vehicle and of the interior of the associated vehicle;

a control device comprising:
  a processor;
  an image data input operatively coupled with the processor, the image data input receiving the driver head image data from the imaging device;
  a non-transient memory device operatively coupled with the processor, the non-transient memory device storing vehicle geometry data representative of relative positions between one or more structures of the associated vehicle, imaging device position data representative of a position of the imaging relative to the one or more structures of the associated vehicle, and safe attention model data comprising a first and second recommended value ranges of a driver road attention parameter of a monitored driver attention condition of the associated vehicle, the first recommended value range of the driver road attention parameter corresponding to an operational condition of the associated vehicle moving forward and the second recommended value range of the driver road attention parameter corresponding to an operational condition of the associated vehicle moving backwards;

driver head direction logic stored in the non-transient memory device, the driver head direction logic being executable by the processor to:
  process the driver head image data to determine a facing direction of the head of the associated driver; and
  generate driver head facing direction data, the driver head facing direction data being representative of the determined facing direction of the head of the associated driver;

control logic stored in in the non-transient memory device, the control logic being executable by the processor to:
  process the driver head facing direction data together with the vehicle geometry data and the imaging device position data to determine an operational value of the driver road attention parameter of the monitored driver attention condition of the associated vehicle;
  selectively for the operational condition of the associated vehicle moving forward, perform a comparison between the first recommended value range of the driver road attention parameter and the determined operational value of the driver road attention parameter of the monitored driver attention condition of the associated vehicle;
  selectively for the operational condition of the associated vehicle moving backwards, perform a comparison between the second recommended value range of the driver road attention parameter and the determined operational value of the driver road attention parameter of the monitored driver attention condition of the associated vehicle;
  determine driver road attention compliance in accordance with a result of the comparison between the first or second recommended value ranges and the determined operational value of the driver road attention parameter of the monitored driver attention condition of the associated vehicle;
  correlate the determined driver road attention compliance with an operational value of a parameter of a lane departure warning (LDW) monitored condition of the associated vehicle; and
  determine an adjustment value for modifying a setting of a LDW system of the associated vehicle in accordance with the determined driver road attention compliance correlated with the operational value of the parameter of the LDW monitored condition of the associated vehicle; and an output operatively coupled with the processor and with an input of the LDW system of the associated vehicle, the output selectively receiving the adjustment value for modifying the LDW setting, and delivering the adjustment value to the associated vehicle for effecting a modification of the setting of the LDW system of the associated vehicle.

* * * * *